(12) United States Patent
Buchanan

(10) Patent No.: US 8,105,843 B2
(45) Date of Patent: Jan. 31, 2012

(54) METHODS AND DEVICES TO ENHANCE SENSITIVITY AND EVALUATE SAMPLE ADEQUACY AND REAGENT REACTIVITY IN RAPID LATERAL FLOW IMMUNOASSAYS

(76) Inventor: Thomas M. Buchanan, Sumner, WA (US)

( * ) Notice: Subject to any disclaimer, the term of this patent is extended or adjusted under 35 U.S.C. 154(b) by 0 days.

(21) Appl. No.: 12/939,982

(22) Filed: Nov. 4, 2010

(65) Prior Publication Data

US 2011/0143365 A1 Jun. 16, 2011

Related U.S. Application Data

(60) Provisional application No. 61/258,074, filed on Nov. 4, 2009.

(51) Int. Cl.
*G01N 33/558* (2006.01)
(52) U.S. Cl. ........ 436/514; 422/401; 422/420; 422/425; 422/430; 435/5; 435/287.2; 435/287.7; 435/287.9; 435/288.2; 435/810; 435/970; 436/525; 436/526; 436/530; 436/531; 436/805; 436/807; 436/810
(58) Field of Classification Search ........................ None
See application file for complete search history.

(56) References Cited

U.S. PATENT DOCUMENTS

| | | | |
|---|---|---|---|
| 4,797,260 A | 1/1989 | Parker | |
| 4,868,131 A | 9/1989 | Hiratsuka | |
| 4,963,325 A * | 10/1990 | Lennon et al. ................ | 422/408 |
| 5,147,609 A | 9/1992 | Grenner | |
| 5,240,862 A | 8/1993 | Koenhen | |
| 5,260,221 A | 11/1993 | Ramel | |
| 5,266,219 A | 11/1993 | Pall | |
| 5,415,994 A * | 5/1995 | Imrich et al. ...................... | 435/5 |
| 5,419,870 A | 5/1995 | Parker | |
| 5,436,129 A | 7/1995 | Stapleton | |
| 5,589,399 A | 12/1996 | Allen | |
| 5,599,715 A | 2/1997 | Warren, III | |
| 5,607,863 A | 3/1997 | Chandler | |
| 5,652,148 A | 7/1997 | Doshi | |
| 5,698,395 A | 12/1997 | Ritterband | |

(Continued)

FOREIGN PATENT DOCUMENTS

WO 02/33380 A1 4/2002

OTHER PUBLICATIONS

Hodinka, R., et al., "Detection of Human Immunodeficiency Virus Antibodies in Oral Fluids," Clinical and Diagnostic Laboratory Immunology 5(4):419-426, Jul. 1998.

(Continued)

*Primary Examiner* — Chris L Chin
(74) *Attorney, Agent, or Firm* — Christensen O'Connor Johnson Kindness PLLC

(57) ABSTRACT

Methods and devices for rapid lateral flow immunoassays to detect specific antibodies within a liquid sample while also validating the adequacy of the liquid sample for the presence of immunoglobulin and the integrity and immunoreactivity of the test reagents that detect the antibodies of interest, without requiring instrumentation. The methods and devices provide for delivery of a diluted liquid sample to a single location that simultaneously directs the liquid flow along two or more separate flow paths, one that serves as a positive control to confirm that all critical reagents of the test are immunoreactive, and that the sample being tested is adequate, and the other to detect specific antibodies if present.

30 Claims, 22 Drawing Sheets

U.S. PATENT DOCUMENTS

| | | |
|---|---|---|
| 5,744,098 A | 4/1998 | Kratzer |
| 5,792,425 A | 8/1998 | Clark |
| 5,849,249 A | 12/1998 | Jones, Jr. |
| 5,869,003 A * | 2/1999 | Nason .......................... 422/411 |
| 5,879,951 A | 3/1999 | Sy |
| 5,882,940 A | 3/1999 | Ronn |
| 5,905,038 A | 5/1999 | Parton |
| 5,916,521 A | 6/1999 | Bunce |
| 5,939,252 A * | 8/1999 | Lennon et al. .................... 435/4 |
| 5,972,294 A | 10/1999 | Smith |
| 6,010,912 A | 1/2000 | Davies |
| 6,013,460 A | 1/2000 | Levin |
| 6,036,659 A | 3/2000 | Ray |
| 6,057,165 A | 5/2000 | Mansour |
| 6,083,760 A | 7/2000 | Ditlow |
| 6,117,398 A | 9/2000 | Bienhaus |
| 6,126,900 A | 10/2000 | Hildenbrand |
| 6,146,902 A | 11/2000 | McMaster |
| 6,242,261 B1 | 6/2001 | Schoenau |
| 6,271,045 B1 | 8/2001 | Douglas |
| 6,284,194 B1 | 9/2001 | Chu |
| 6,352,862 B1 | 3/2002 | Davis |
| 6,358,730 B1 | 3/2002 | Kane |
| 6,375,896 B1 * | 4/2002 | Wuske et al. ................. 422/411 |
| 6,464,939 B1 * | 10/2002 | Bachand et al. .............. 422/411 |
| 6,489,132 B1 | 12/2002 | Gordon |
| 6,489,172 B1 * | 12/2002 | Bachand et al. .............. 436/180 |
| 6,565,808 B2 * | 5/2003 | Hudak et al. ................. 422/411 |
| 6,632,399 B1 | 10/2003 | Kellogg |
| 6,656,741 B1 | 12/2003 | Nelson |
| 6,756,230 B2 | 6/2004 | Noda |
| 6,863,866 B2 | 3/2005 | Kelly |
| 6,913,152 B2 | 7/2005 | Zuk, Jr. |
| 7,037,425 B2 | 5/2006 | Lee |
| 7,364,914 B2 | 4/2008 | Buchanan |
| 2003/0049857 A1 | 3/2003 | Chan |
| 2006/0234209 A1 | 10/2006 | Walker |
| 2006/0234210 A1 | 10/2006 | Kenan |

OTHER PUBLICATIONS

Pesce, M.A., et al., "Rapid HIV Antibody Testing: Methods and Clinical Utilization," American Journal of Clinical Pathology: Pathology Patterns Reviews 126(Suppl 1):S61-S70, Dec. 2006.

International Search Report and Written Opinion mailed Jul. 28, 2011, issued in corresponding International Application No. PCT/US2010/055523, filed Nov. 4, 2010, 11 pages.

* cited by examiner

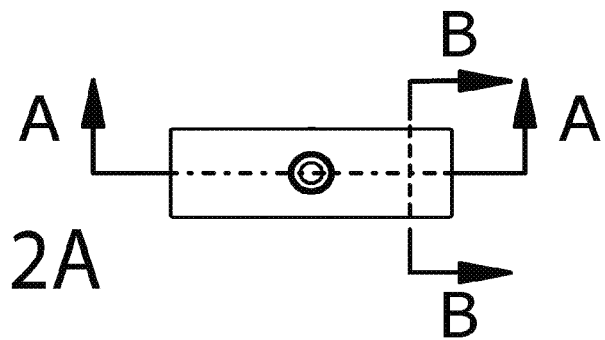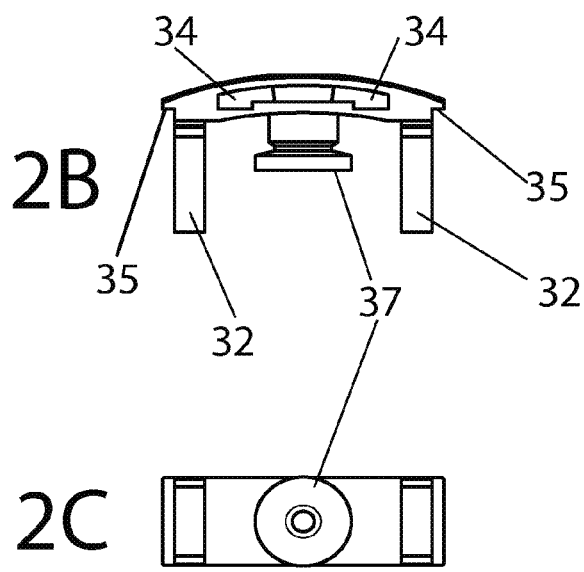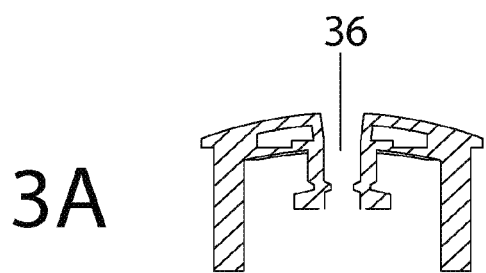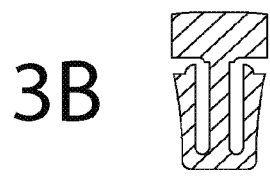
FIGS. 2 & 3

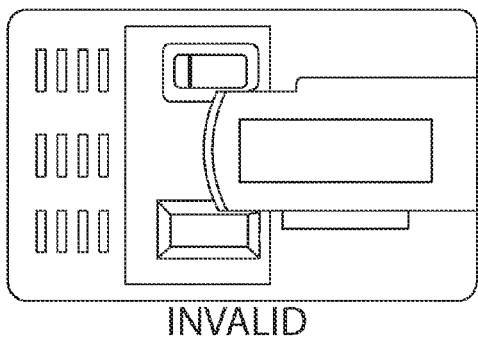
15B
INVALID
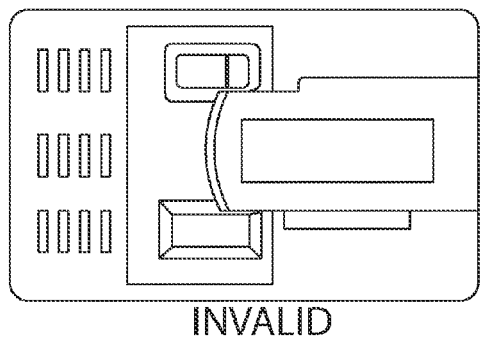
15C
INVALID
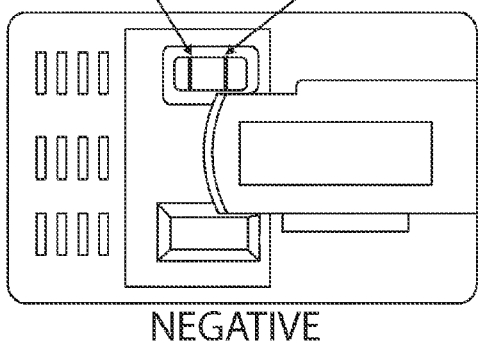
15D
NEGATIVE
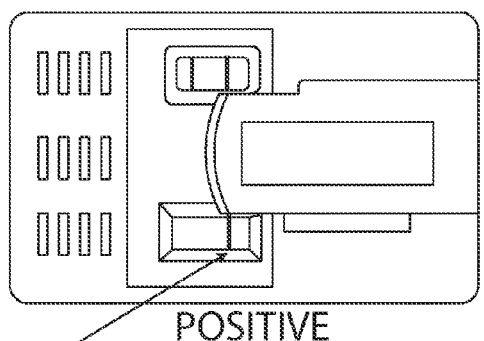
15E
POSITIVE
FIG. 15B-E

METHODS AND DEVICES TO ENHANCE SENSITIVITY AND EVALUATE SAMPLE ADEQUACY AND REAGENT REACTIVITY IN RAPID LATERAL FLOW IMMUNOASSAYS

CROSS-REFERENCE TO RELATED APPLICATION

This application claims the benefit of U.S. Patent Application No. 61/258,074, filed Nov. 4, 2009, expressly incorporated herein by reference in its entirety.

FIELD OF THE INVENTION

The invention relates generally to immunoassay devices and the methods for their use. More specifically, the invention relates to rapid immunoassays that utilize capillary lateral flow for rapid detection of ligands within biologic fluids. The invention relates to methods and devices that permit evaluation of sample adequacy and confirmation of critical reagent immunoreactivity during performance of rapid lateral flow immunoassays, and to methods and devices that provide increased sensitivity within such immunoassays.

The methods and devices specifically pertain to confirmation of adequate levels of immunoglobulin in the liquid sample being evaluated in the rapid lateral flow immunoassay, and to confirmation of immunoreactivity of antigens, particulate markers, and any control monoclonal antibodies, polyclonal antibodies or other ligands that are present on the membranes of the assay. The methods and devices also specifically provide simple device designs and procedures that allow ligands to interact with their specific binding partners more favorably than in conventional lateral flow rapid diagnostic tests with respect to interference from or detection by particulate markers. The present invention provides rapid tests with higher sensitivity than conventional lateral flow immunoassays.

The invention methods and devices are illustrated using HIV antibodies and antigens, and human C-Reactive Protein and its ligands. These methods and devices of the invention provide a platform strategy and device procedures applicable to rapid detection of antibodies specific to other antigens, or for detecting other ligand binding pairs and other medical conditions.

BACKGROUND OF THE INVENTION

Many rapid lateral flow diagnostic tests are in use throughout the world today. Rosenstein was the first to describe the methodology (U.S. Pat. No. 5,591,645) in 1987, and many others have contributed improvements since then (U.S. Pat. No. 4,855,240, Rosenstein et al.; U.S. Pat. No. 5,602,040, May et al.; U.S. Pat. No. 5,714,389, Charlton et al.; U.S. Pat. No. 5,824,268, Bernstein et al.; and U.S. Pat. No. 7,189,522, Esfandiari). However, none of these tests that detect antibodies to specific antigens provide a means within each test to simultaneously detect whether the sample being evaluated actually contains a sufficient amount of immunoglobulin to allow detection of specific antibodies, if present. Also, none of these tests currently available have built-in controls to simultaneously report immunoreactivity of the critical reagents required for the test to provide accurate results. These two important omissions mean that some tests may provide falsely negative results due to inadequate sample or failed reagents. When a person has HIV antibodies, and they provide an inadequate sample to the rapid test for evaluation, or when the critical reagents of the test have deteriorated, no lines will develop that would normally indicate a positive result, such as antibodies in the test sample to HIV antigen on the test membranes. The test user is likely to incorrectly conclude that the test is negative because no lines have appeared. However, had controls for sample adequacy and reagent reactivity been included in the test, this mistake would not occur. The user would observe that either the sample was inadequate for testing, or that critical reagents required for accurate test performance were not working, and make the correct conclusion that the test result was INVALID and could not be interpreted, rather than falsely concluding that the test was negative.

Specific examples of this type of failure of rapid tests for HIV have been reported in Kenya and Uganda (Mar. 28, 2009—Uganda Monitor Online, Dr. Z. Akol, the STD/AIDS Control Programme manager at the Health Ministry, Kampala, Uganda) and noted failures of tests given to 6,255 people due to exposure to harsh storage conditions and using tests beyond their expiration dates, failures that would be detected with controls for antigen and critical reagent reactivity, but not without, and also failures due to errors the tests short reading windows of 20 minutes or less, reading beyond which may give false positives. In India, more than one hundred thousand persons were tested in five states with faulty tests that lacked controls to detect reagent failure or sample inadequacy—76,464 persons were tested in Mumbai alone, in the period 2-07 through 5-07, and S Kudalkar, chief of the Mumbai District AIDS Control Society (MDACS) stated "It is those who tested negative in those three months who are a cause for worry. Since they aren't tested again, if their result is wrong, they could have missed appropriate treatment." Dr. A. Deshpande also pointed out that pregnant mothers with HIV infection may have been missed. The Delhi High Court ruled on May 25, 2009 that all those tested between February-07 and May-07 must be retested due to the poor quality of the HIV rapid tests used (M. Rajadhyaksha, TNN 29 Jul. 2009).

Many current rapid lateral flow tests contain a so-called positive control, which is nothing more than a incomplete procedural control that simply reports that fluid introduced into the rapid test has migrated to the end of the test results window (see U.S. Pat. No. 5,989,921, Charlton et al., claim 1, line 26, "said control site comprising an immobilized binder that binds said conjugate," regardless of whether antibody is present or absent in the sample. Also see U.S. Pat. No. 5,656, 503, May et al., claim 42 (d), line 63 "a control zone downstream from said test result zone in said dry porous carrier for binding labeled reagent to indicate that said applied liquid biological sample has been conveyed by capillarity beyond said test result zone." Again, the binding is independent of the presence or absence of the analyte of interest in the liquid biological sample. Also see OraSureOraquick ADVANCE Rapid HIV-1/2 test PMA, that refers to "a goat anti-human IgG procedural control immobilized onto a nitrocellulose membrane in the . . . . Control (C) zone" . . . "This built-in procedural control serves to demonstrate that a specimen was added to the vial and that the fluid has migrated adequately through the test device". These controls do not catch false negative results that may result from testing an inadequate sample or failure of critical test reagents.

Current advanced instrument based tests for detection of antibodies to HIV typically will detect the presence of antibodies to HIV a few days sooner during seroconversion following infection than can be detected with rapid lateral flow diagnostic tests, and well before Western Blot confirmatory tests become positive. It would be desirable for rapid lateral flow diagnostic tests to have increased sensitivity that allowed them to more closely approximate the sensitivity of instrument based tests.

Current rapid lateral flow diagnostic tests for HIV are approved by the US FDA for use with only very short reading windows, beyond which the test must not be interpreted due to an increased risk of false positive results. For example, the Trinity Biotech UniGold Rapid HIV-1 antibody test must be read over a 2 minute window, precisely 10-12 minutes after test initiation. The Inverness Determine HIV-1/2 antibody test must be read over a 5 minute window between 15 and 20 minutes, and the OraSureOraQuick ADVANCE HIV-1/2 test must be read over a 20 minute window between 20 and 40 minutes. In busy emergency room or urgent care clinics, this limited reading period for the rapid tests can be difficult to achieve, resulting in either failure to read the test appropriately, or failure of widespread use of the test due to its limitations. It would be desirable to have a test with a reading window of at least several hours, and preferably several days to months.

Currently existent rapid lateral flow diagnostic test devices occasionally permit backflow of test reagents from the downstream absorbent pad, upstream into the reading window. When this occurs, the test results are obscured and accurate reading of the results becomes impossible. It would be desirable to have a method and device that utilized the method that prevents such backflow of reagents.

SUMMARY OF THE INVENTION

An important object of this invention provides methods, and rapid lateral flow immunoassay devices that utilize the methods, that decrease the chances that an erroneous result will occur when untrained users utilize the improved methods and devices of this invention as compared to conventional lateral flow rapid immunoassays.

It is therefore an object of this invention to provide a method, and rapid lateral flow immunoassay device that utilizes the method, to evaluate sample adequacy in terms of whether the sample contains sufficient immunoglobulin to allow detection of immunoglobulin molecules within the sample that are specifically directed at antigens or analytes of interest.

It is a further object of the invention to provide a method, and rapid lateral flow immunoassay device that utilizes the method, to confirm reactivity of all critical reagents of the rapid test. This includes confirmation of reactivity of immobilized antigens or analytes, of any positive control mobilizable immunoglobulins utilized within the immunoassay format, and reactivity of the particulate marker that detects immunoglobulin molecules within the biological liquid sample that specifically recognize the immobilized antigens or analytes of interest, and that also recognizes positive control immunoglobulins within the test format.

An additional particularly desirable object of the invention is to provide a method, and a rapid lateral flow immunoassay device that utilizes the method, that allows oral fluid to be collected from the tooth-gingival crevice line by a custom swab that fits directly into the device and permits direct dilution of that gingival crevice fluid from the swab and analysis of that diluted sample for specific antibodies. Since many patients prefer tests that do not require a blood sample, the ability to test oral fluid in a simple to perform test should provide wider acceptability for its use.

It is also an object of the invention to provide a method, and a rapid lateral flow immunoassay device that utilizes the method, that provides increased the sensitivity of the immunoassay as compared to conventional lateral flow immunoassays, by providing more favorable interactions between specific binding pairs included within the assay format.

It is an additional object of the invention to provide a method, and a rapid lateral flow immunoassay device that utilizes the method, that maintains the simplicity of performance and interpretation inherent in rapid lateral flow immunoassays, that has permitted worldwide use of such rapid tests by untrained users.

It is a further object of the invention to provide a method, and a rapid lateral flow immunoassay device that utilizes the method, that increases the reading window over which the test result can be accurately interpreted from between 10 to 15 minutes at the earliest, to up to 24 hours or more.

It is also an object of the invention to provide a method, and a rapid lateral flow immunoassay device that utilizes the method, that prevents backflow of reagents from the downstream absorbent pad of the rapid test device into the upstream reading window for the test.

An additional object of the invention is that any test devices that utilize the methods of this invention be designed as compatible with injection molding to produce the plastic housing parts for the device, and that the designs are suitable for automated assembly manufacturing.

As discussed in detail in the following Examples, Figures and Detailed Description, this invention has developed methods, and devices that achieve the above objectives.

This invention has discovered a combination of specific immunoglobulin binding reagents that allow detection of the presence of immunoglobulin in rapid lateral flow formats, while overcoming problems with the non-specific interactions that occur with many binding pairs which prevent accurate assessment of whether adequate immunoglobulin is present in test samples.

The invention further provides methods and devices that allow confirmation of immunoreactivity of the antigen being used to detect antibodies specific to it, while at the same time confirming the immunoreactivity of the particulate marker being used within the test, as well as immunoreactivity of any monoclonal antibodies or polyclonal antibodies being used to bind to critical epitope determinants of the antigen being used in the test to detect antibodies in the liquid sample being detected. This is accomplished by the test devices and membrane configurations provided in the invention that direct the liquid sample being tested along two or more separate flow paths.

One flow path, designated the positive control reagent pathway is specifically designed to evaluate sample adequacy and the immunoreactivity of the critical test reagents. It contains antigen or antigens immobilized on nitrocellulose in the downstream portion of this flow path that is (are) identical to the same antigen or antigens coated on the second flow path designed to detect antibodies specific to that antigen or those antigens. The upstream portion of the positive control reagent pathway contains dried mobilizable monoclonal or polyclonal antibodies or other ligands that bind specifically to the epitope or epitopes being recognized on the downstream test antigen or antigens, the same epitopes being recognized in the other flow path (or paths) over which liquid samples are evaluated for the presence of antibody specific to this antigen. The upstream portion of the positive control reagent flow path also contains mobilizable dried particulate marker, that when mobilized will recognize and bind to the mobilizable dried monoclonal or polyclonal antibodies or other ligands that specifically recognize the downstream test antigen or antigens When mobilized and migrated over the downstream immobilized test antigen or antigens the binding of the particulate marker to an immobilized antigen confirms three features: (1) immunoreactivity of the antigen, (2) immunoreactivity of the monoclonal or polyclonal antibodies directed at the specific antigen, and (3) immunoreactivity of the particulate marker. The positive control reagent pathway also contains further downstream an immunoglobulin recognizing reagent that specifically recognizes immunoglobulin in the test sample if it is present in sufficient amounts to allow accurate performance of the rapid test. This reagent is adjusted in concentration so that it does not bind sufficient positive control antibodies to allow visually recognizable binding by the mobilizable particulate marker of the positive control reagent pathway, but will show a visible line of binding of particulate marker if the diluted sample presented to the test device contains sufficient immunoglobulin to be an adequate sample.

The second flow path (and any additional flow paths) is (are) designated the specific antibody flow path(s) for the purpose of detecting specific antibodies to immobilized antigens (analytes) of interest.

One advantage of the methods and devices provided in this invention is that the positive control reagent pathway provides one or more observable lines indicating for each observable line that the antigen recognized is reactive and that a comparable line can be expected for that antigen in the specific antibody pathway if specific antibodies are present. The antigen used in each pathway is identical, and it is immobilized using identical conditions in each pathway. Also, particulate marker used in the positive control reagent pathway is identical to the particulate marker used in the pathway to detect antibodies to specific antigens. This provides assurance when no line is present in the specific antibody pathway that the negative result was not due to inactivity of the antigen or degradation of the particulate marker. This type of control is intuitively easier to understand and facilitates proper use and evaluation of the test results, as compared to previously described controls in which a positive control is the absence of a line. The positive control reagent pathway of the invention is also preferable to controls in which the antigen is detected by immobilized monoclonal antibody, because that type of control requires the antigen to be bound to particulate marker which means it is different from native antigen used in the test, or if native antigen is used, it must be bound upstream to a monoclonal antibody or other ligand that contains a particulate marker, and it has thus been modified and is not directly comparable to the antigen used in the pathway for detecting antibodies specific to the test antigen.

The devices of this invention provide for the fluid being tested to be directed into two or more separate pathways. Separating the positive control reagent pathway that confirms reactivity of critical reagents from a different pathway to detect antibodies specific to antigens of interest prevents interference of different control and test components that would occur if positive control monoclonal or polyclonal antibody reagents were combined into the pathway to detect test sample antibodies to a specific antigen. The flow direction, from the membrane that collects the diluted liquid sample within the device into the two or more separate pathways and ultimately into absorbent pads at the downstream end of each pathway, prevents backward flow contamination of the specific antibody detection pathway by reagents found in the positive control critical reagent pathway.

The invention includes the possibility of two or more separate ports, one allowing addition of buffer to the critical reagent positive control pathway, and one or more additional ports to accept liquid sample being tested for antibodies or ligands specific to immobilized antigens or analytes of interest. This also would provide a means within the contemplated invention to provide proof that the critical reagents of the test are intact, at the same time as evaluating the test results for the presence or absence of antibodies to specific antigens or analytes of interest. However, the preferred embodiment of this invention, for purposes of ease of use of the test, is to be able to add the liquid sample to a single location, and have the devices direct the liquid sample over two or more pathways from that single location, to provide observable results from each pathway, as provided for in this invention.

It should be noted that the two or more lateral flow paths described in this invention, are to be distinguished from the two paths or dual paths first described by Rosenstein et al. (U.S. Pat. No. 4,855,240) and subsequently by Bernstein et al. (U.S. Pat. No. 5,824,268) and Esfandiari (U.S. Pat. No. 7,189, 522 B2). In each of these U.S. patents, particulate tracer is run over one pathway and the sample runs over a separate pathway. In contrast, in this invention, both sample and particulate marker are run over each pathway. This invention contains controls to test for sample adequacy and for immunoreactivity of the critical reagents whereas these three previously cited patents do not contain these controls.

It should also be realized that U.S. Pat. No. 6,627,459 B1, entitled "Immunoassay Controls" by Tung et al is different from than the present invention. It contains a positive control that is non-cross reactive with the biological analyte to be detected, whereas this invention uses the identical antigen for the positive control which is used to detect specific analytes, and both are identically immobilized on nitrocellulose. This is accomplished by placing the antigen positive control in a separate pathway from the pathway to detect antibodies specific to that antigen, and simultaneously directing the sample being tested over each pathway. In this way, the antigen immobilized and used as the positive control does not interfere with the same antigen used in the separate pathway which detects antibodies specific to that antigen. Also because the positive control antigen is stored under identical conditions to the same antigen used in the pathway for detecting specific antibodies, it is a preferable measure of possible adverse effects on immunoreactivity of storage conditions, such as excess heat, excess humidity, exposure to oxygen, and storage beyond expiration dates, than a non-identical, non-cross reactive positive control as described by Tung et al.

The invention provides a custom swab design that when utilized with the rapid test device design, provides for isolation of a portion of swab membrane saturated with gingival crevice fluid, which is then removed and simultaneously diluted and delivered to the test device according to the method of Buchanan (U.S. Pat. No. 7,364,914 B2). The simplicity of this device design decreases the chance of user error. Further advantages regarding oral fluid processing, capillary flow and speed of test completion, and protection against spillage, are provided in this invention by collecting the diluted oral fluid sample into a membrane rather than a well, and providing fluid communication from the diluted sample membrane into the positive reagent control pathway as well as the specific antibody pathway.

The invention also provides a designed insert that fits into the rapid test device and allows separation of acellular components from two drops of whole blood. The whole blood from a fingerstick or venipuncture may easily be added directly to the insert. Migration by capillarity within the insert separates acellular components of the blood at the leading edge of the migration from trailing cellular components. A defined amount of this acellular portion is then isolated and diluted within the test device and the diluted sample is directed into the flow pathways of the device for detection of antibodies to specific antigens.

This invention provides for more favorable interactions between mobilizable particulate marker, specific antibodies, and the immobilized antigens to which those antibodies are directed as the result of two design changes. First, when the sample is diluted and removed from the saturated swab or whole blood membrane by applying test running buffer under pressure in the test device it is delivered to the center of the diluted sample membrane. The concentration of diluted sample along the membrane varies from most concentrated at the membrane periphery to more dilute as it approaches the center of the membrane, and finally no sample and only running buffer at the center of the diluted sample membrane. The rapid test designs of this invention connect the periphery of the diluted sample membrane with the upstream portion of the separate pathways; the reagent positive control pathway and the specific antibody pathway or pathways. Second, the test designs of this invention that provide increased sensitivity orient a strip containing particulate marker so that its ends overlap the space between the periphery of the diluted sample membrane and the upstream portion of each pathway, but one side of the diluted sample membrane partially overlaps one side of the remaining particulate marker membrane. This orientation results in the initial interaction of diluted sample and particulate marker being identical to conventional lateral flow tests. Diluted sample flowing down each pathway pushes particulate marker ahead of it, some of which does not interact with sample, and flows into the absorbent pad. The leading edge portion of marker-sample interaction involves an excess of immunoglobulin relative to marker, necessitating dilution of the test sample in many antibody tests in order to produce observable results. The ensuing interactions of conventional lateral flow immunoassays contain continued high levels of immunoglobulin relative to diminishing and then absent marker. In contrast, the new methods of utilizing new designs and orientation of particulate marker pads of this invention, provide continued supply of marker throughout test development. This innovation, together with a diluted sample membrane that provides a range of dilutions of immunoglobulin to marker produce more favorable marker-immunoglobulin complexes that produce observable results. Together, these more favorable characteristics result in higher sensitivity for detection of ligands of interest in the diluted sample.

The new generation design of this invention also increases the proportion of complexes that are capable of producing observable binding of particulate marker to immobilized antigens by providing continued delivery of particulate marker to the rapid immunoassay test over a much longer time course of the test. Antibodies that have flowed down each pathway and bound to antigens prior to complexing with marker that would have been missed with conventional lateral flow techniques may be recognized by this new generation design that provides subsequent marker flowing down the same pathways. Unfavorable ratios of marker to antibody binding that produced complexes too large to flow paths smoothly along the test device pathways also have an opportunity to reach more favorable size and flow conditions by continued flow past them of marker excess or antibody excess solutions during different periods of the rapid test design of this invention. Finally, the new generation test design provides running buffer that contains no antibody or particulate marker in the final stages of flow of fluid through the rapid test pathways. This final running buffer wash facilitates removal of any residual particulate marker from the reading window of the rapid test that has not specifically bound to immobilized antigens or ligands, providing a white background against which to easily read the test results.

The invention maintains the simplicity of lateral flow immunoassays that makes it easy to use and interpret. In the oral fluid version, the user simply swabs the gingival crevice margin with the provided custom swab and then places it into its precise location in the test device. The dilution port is then pushed down to lock in place and isolate a section of swab membrane saturated with oral fluid and the tip of the provided vial of running buffer is inserted into the opening in the top of the dilution port and squeezed to force out the liquid simultaneously removing and diluting the oral fluid from the isolated membrane and delivering it into the test device. The test result can then be read through the windows of the test device in approximately ten minutes. In the whole blood version, an insert to collect whole blood is placed into the opening of the test device cover in the precise location that receives the swab in the oral version. This insert contains a membrane that isolates acellular from cellular blood components when two drops of blood from a fingerstick or venipuncture are placed into the funnel receptacle of the insert, and allowed to migrate for 4 minutes from the receiving area to the opposite end of the sample receiving membrane. The dilution port is then pushed down into the locked position and running buffer is added from the provided vial as in the oral fluid test and the result may be observed in the reading windows of the test device after 6 additional minutes.

This invention includes design modifications that provide a large absorbent pad that absorbs all of the one ml of diluted sample fluid added to the test device. This large volume absorbent pad, plus design of the outflow wicks from the downstream ends of the reagent positive control pathway and specific antibody pathway connecting to the absorbent pad and the device design that includes overlying vent areas in the cover of the test device to facilitate evaporation of test liquid from the absorbent [pad and keep] pad, keep all flow within the test device from upstream to downstream portions of each pathway and into the absorbent pad, and prevent backflow into the reading window that might limit the reading time over which the test result may be accurately read.

The plastic components of the test device and the orientation of the membranes within the device are designed to be compatible with automated assembly manufacturing.

The following is a description of a representative method of the invention with reference to the flow paths and reference numerals set forth in FIG. 13. In one embodiment, the invention provides a method for detecting an analyte in a liquid sample, comprising:

(a) isolating a portion of the compressible membrane containing at least a portion of a liquid sample to be analyzed by applying compressive force on top and bottom surfaces of the membrane along the perimeter of an area to be isolated thereby defining a non-compressed area of the membrane centripetal to the compressed perimeter;

(b) delivering a liquid diluent under pressure to the isolated portion of the membrane to release at least a portion of the liquid sample from the isolated portion of the membrane to provide a diluted sample;

(c) contacting the diluted sample with a second porous membrane (8) having a first end and a second end, wherein the diluted sample flows toward the first and second ends (FD2);

(d) conducting the diluted sample from the first end of the second porous membrane to the first end of a third porous membrane (upper 7) having a first end and a second end, wherein the third porous membrane comprises a mobilizable marker that binds to the analyte and a mobilizable analyte binding partner (e.g., F240), and wherein the diluted sample further comprises the marker and analyte binding partner once the diluted sample flows to the second end of the third porous membrane;

(e) conducting the diluted sample from the second end of the second porous membrane (8) to the first end of a fourth porous membrane (lower 7) having a first end and a second end, wherein the fourth porous membrane comprises the mobilizable marker and wherein the diluted sample further comprises the marker once the diluted sample flows to the second end of the fourth porous membrane;

(f) conducting the diluted sample further comprising the marker from the second end of the third porous membrane to the first end of a fifth porous membrane (9) having a first end and a second end, wherein the fifth porous membrane comprises a first region comprising an immobilized analyte binding ligand (e.g., HIV antigen) wherein the immobilized analyte binding ligand is effective in binding the mobilizable analyte binding partner (and the analyte, e.g., HIV antibody), and the marker is effective in binding to the mobilizable analyte binding partner (and the analyte) (bound to the immobilized ligand), as the diluted sample comprising the marker and mobilizable analyte binding partner flows toward the second end of the fifth porous membrane, thereby providing an indication that the mobilized binding partner, immobilized analyte binding ligand, and marker are operating satisfactorily; and (g) conducting the diluted sample further comprising the marker from the second end of the fourth porous membrane to the first end of a sixth porous membrane (10) having a first end and a second end, wherein the sixth porous membrane comprises a first region comprising the immobilized analyte binding ligand wherein the immobilized analyte binding ligand is effective in binding the analyte and the marker is effective in binding to the analyte (bound to the immobilized ligand) as the diluted sample comprising the marker flows toward the second end of the fifth porous membrane, thereby providing an indication that the sample includes the analyte, when the analyte is present in the sample.

In one embodiment, the method further comprises conducting the remaining diluted sample from the second end of the fifth porous membrane to the first end of a seventh porous membrane (upper 11) having first and second ends, wherein the seventh porous membrane draws the diluted sample from the second porous membrane (FD3); and conducting the remaining diluted sample from the second end of the sixth porous membrane to the first end of an eighth porous membrane (lower 11) having first and second ends, wherein the eighth porous membrane draws the diluted sample from the second porous membrane.

In one embodiment, the fifth porous membrane (9) further comprises a second region comprising an immunoglobulin binding partner immobilized therein (for example, downstream from the immobilized ligand), wherein the immunoglobulin binding partner is effective in binding the immunoglobulin in the liquid sample, and wherein the mobilizable marker is effective for binding to the immunoglobulin, as the diluted sample flows toward the second end of the sixth porous membrane, thereby providing an indication that the sample has immunoglobulin sufficient to confirm sample adequacy.

In one embodiment, the sixth porous membrane (10) further comprises a second region comprising an immunoglobulin binding partner immobilized therein (for example, downstream from the immobilized ligand), wherein the immunoglobulin binding partner is effective in binding the immunoglobulin in the liquid sample, and wherein the mobilizable marker is effective for binding to the immunoglobulin, as the diluted sample flows toward the second end of the sixth porous membrane, thereby providing an indication that the sample has immunoglobulin sufficient to confirm sample adequacy.

In one embodiment, the liquid sample is added to the compressible porous membrane to provide a portion of the compressible membrane containing at least a portion of the liquid sample.

In one embodiment, the liquid sample is whole blood. In one embodiment, the liquid sample is gingival crevice oral fluid.

In one embodiment, the analyte binding partner is an antigen and the analyte is an antibody. In one embodiment, the analyte binding partner is an antibody and the analyte is an antigen. In one embodiment, the analyte binding partner is the HIV antigen and the analyte is the HIV antibody.

The following is a description of a representative device of the invention with reference to the flow paths and reference numerals set forth in FIG. 13. In one embodiment, the present invention provides a device for detecting an analyte in a liquid sample, comprising:

(a) a compressible porous membrane for receiving a liquid sample;

(b) first and second members adjacent opposing major surfaces of the compressible porous membrane, wherein the first and second members are engageable to apply compressive force on top and bottom surfaces of the membrane along the perimeter of the area to be isolated, thereby defining a non-compressed area of saturated membrane centripetal to the compressed perimeter;

(c) a port adapted to receive delivery of a second fluid, wherein the port is further adapted to deliver the second fluid under pressure to the isolated portion of the membrane to force the removal of at least a portion of the liquid sample from the isolated portion of the membrane to provided a diluted sample;

(d) a second porous membrane (8) for receiving diluted liquid sample from the compressible membrane, the second porous membrane having first and second ends;

(e) a third porous membrane (upper 7) comprising a mobilizable marker effective in binding to the analyte and a mobilizable antigen binding partner (e.g., F240), the third porous membrane having first and second ends, wherein the first end of the second porous membrane is in liquid communication with the first end of the third porous membrane;

(f) a fourth porous membrane (lower 7) comprising the mobilizable marker, the fourth porous membrane having a first end and a second end, wherein the second end of the second porous membrane is in liquid communication with the first end of the fourth membrane;

(g) a fifth porous membrane (9) comprising a first region comprising an immobilized analyte binding ligand (e.g., HIV antigen), wherein the immobilized analyte binding ligand is effective in binding the mobilizable antigen binding partner (and the analyte), the fifth porous membrane having a first end and a second end, wherein the second end of the third porous membrane is in liquid communication with the first end of the fifth membrane;

(h) a sixth porous membrane (10) comprising a first region comprising an immobilized analyte binding ligand (e.g., HIV antigen), wherein the immobilized analyte binding ligand is effective in binding the analyte, the sixth porous membrane having a first end and a second end, wherein the second end of the fourth porous membrane is in liquid communication with the first end of the sixth membrane.

In one embodiment, the device further comprises a seventh porous membrane (upper 11) for drawing the diluted sample from the second porous membrane (FD3), the seventh porous membrane having a first end and a second end, wherein the second end of the fifth porous membrane is in liquid communication with the first end of the seventh membrane; and an eighth porous membrane (lower 11) for drawing the diluted sample from the second porous membrane (FD3), the eighth porous membrane having a first end and a second end, wherein the second end of the sixth porous membrane is in liquid communication with the first end of the eighth membrane.

In one embodiment, the fifth porous membrane further comprises a second region comprising an immunoglobulin binding partner immobilized therein (for example, downstream from the immobilized ligand), wherein the immunoglobulin binding partner is effective in binding the immunoglobulin in the liquid sample, and wherein the mobilizable marker is effective for binding to the immunoglobulin, as the diluted sample flows toward the second end of the fifth porous membrane, thereby providing an indication that the sample has immunoglobulin sufficient to confirm sample adequacy.

In another embodiment the sixth porous membrane further comprises a second region comprising an immunoglobulin binding partner immobilized therein (for example, downstream from the immobilized ligand), wherein the immunoglobulin binding partner is effective in binding the immunoglobulin in the liquid sample, and wherein the mobilizable marker is effective for binding to the immunoglobulin, as the diluted sample flows toward the second end of the fifth porous membrane, thereby providing an indication that the sample has immunoglobulin sufficient to confirm sample adequacy.

In one embodiment, the first end of the second porous membrane overlaps the first end of the third porous membrane. In one embodiment, the second end of the third porous membrane overlaps the first end of the fifth porous membrane. In one embodiment, the second end of the fifth porous membrane overlaps the first end of the seventh porous membrane. In one embodiment, the second end of the second porous membrane overlaps the first end of the fourth porous membrane. In one embodiment, the second end of the fourth porous membrane overlaps the first end of the sixth porous membrane. In one embodiment, the second end of the sixth porous membrane overlaps the first end of the eighth porous membrane.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 2A is a top plan view, FIG. 2B is a front elevation view, FIG. 2C is a bottom plan view of sample dilution port (2).

FIG. 3A is a cross section view of dilution port (2, FIG. 1) through its central channel (36, FIGS. 3A and 10C) and its hook arms (32, FIG. 2B) and FIG. 3B is a cross section view of dilution port (2) through one of its hook arms (32). The plane of the cross section and the direction of sight for FIG. 3A are indicated by the dotted line and arrows which are labeled A in FIG. 2A. The plane of the cross section and the direction of sight for FIG. 3B is indicated by the dotted line and arrows labeled B in FIG. 2A.

FIG. 7A contains ridges (24) that position the midpiece on base (FIG. 1, 12), a depression (23) to hold an o-ring, and a central channel (25) that permits flow of diluted sample from the top side to bottom side of the midpiece. FIGS. 7B and 7C show o-ring (26, also FIG. 1, 5) in place within its channel in the midpiece and the protruding exit area (27) for channel (25) on the bottom surface of midpiece.

FIG. 8A illustrates placement of the diluted sample membrane (8), test nitrocellulose membrane (9), control nitrocellulose membrane (10) and absorbent pads (11) within the base. FIG. 8B illustrates the receptacles (29) within the base receive the hook arms (FIG. 9C, 32) of the dilution port which enter the receptacle through opening 28 (FIG. 8A) of the receptacles. FIG. 8C shows windows 30 in the receptacles through which the hook arms of the dilution port protrude once the dilution port is pushed down into the receptacles until the hook arms (32, FIG. 2; 32S, FIGS. 9D and 9E) lock beneath ridge 33 (FIGS. 8B and 9E). This protrusion into window 30 of the receptacle by the hook arms locks the dilution port in place in four separate areas, one protruding hook arm into each window 30 of each receptacle.

FIG. 9A is a top plan view of the cover (3) with dilution port (2) and yoke (1) in place. The dotted line in FIG. 9A is the plane of a cross-sectional view through the middle of one of the hook arms 32 (FIG. 9C) to produce FIGS. 9D and 9E, and the line of sight for these figures is illustrated by the arrows. FIG. 9D shows cross sections of the hook arms relative to the base receptacles in the up-unlocked position and FIG. 9E shows the hook arms in the down-locked position within the base receptacles. FIG. 9B illustrates how the yoke (1) prevents the dilution port (2) from being depressed down into the cover opening by passing through openings (34, FIGS. 2B and 10B). It may be removed by pushing the yoke arms (13, FIGS. 4B and 13, FIG. 9B) toward each other while simultaneously pulling on finger tabs (14, FIG. 4A). Once the yoke is removed the dilution port may be depressed to the locked position within the base receptacles, and its top surface is then flush with the top surface of the opening for the dilution port in the cover (FIG. 9C, 2). Once flush with the cover the ridges (35, FIG. 2B) on the undersurface of the periphery of the long dimension of the dilution port cover abut ridges (18, FIG. 5A) of the cover. These prevent the cover from being removed once the dilution port is locked into the base. FIG. 9D is a cross-sectional left view of a hook arm in its base receptacle in the up position. Hook arms (32S) sit above the upper ridges (33S) of the base receptacle. FIG. 9E is a cross-sectional left view of a hook arm in its base receptacle in the down and locked position. The locking of dilution port into the receptacle is accomplished by four points, two for each hook arm, as illustrated by hook arms 32S now being located beneath ridges 33S which prevent the dilution port from moving back upward once locked into position.

FIG. 10A is a top plan view of the cover with dilution port in place. The dotted line indicates the plane of the cross-sectional view of the dilution port through the top opening of the central channel (31, FIG. 9A) and the line of site for viewing cross sections in this plane for FIGS. 10B and 10C is indicated by the arrows and the letters B and C. FIG. 10B is the cross section with the dilution port in the up and unlocked position, and FIG. 10C is the cross section with the dilution port in the down and locked position. FIG. 10B shows openings (34) in the dilution port (3S) from which the yoke was removed to allow the dilution port to be depressed into the device. Other components of the dilution port in the FIG. 10B cross section include the central stem of each hook arm (35S), the central channel (36) of the dilution port through which diluent passes after being introduced through the opening in the top of the dilution port (31, FIGS. 10B and 9A), and receptacles (29S) in the base (12S) that accept the hook arms of the dilution port. FIG. 10B illustrates cross sections of the inferior surfaces (37S) of the walls of the dilution port surrounding its central channel which together with an o-ring (5S) located within a channel in the midpiece (FIG. 7A, channel 23, and FIG. 7B, o-ring 5) provide compressive force on top and bottom surfaces, respectively, of the swab fabric (FIG. 10B, 21S) saturated with oral gingival crevice fluid in order to isolate an area of non-compressed saturated membrane.

FIG. 11 shows the isolated area of non-compressed swab fabric (26) which is located centripetal to the perimeter of compression formed by o-ring (FIG. 10B, 5S) and inferior surfaces of the dilution port (FIG. 10B, 37S). When diluent fluid is applied under pressure in the direction of the arrow through channel 36, FIG. 10C, it removes the isolated sample of gingival crevice fluid from the isolated area of non-compressed membrane (26, FIGS. 10C and 11) and dilutes it. The diluted sample exits from beneath the midpiece through a channel formed by inferior projections (27S, FIG. 11) on its undersurface and into the diluted sample membrane (FIG. 11, 8S and FIG. 1, 8) and from there wicks onto the other membranes of the test device. FIG. 11 also demonstrates a cross section of the frame (38S) of the oral swab. It occupies the periphery of the portion of the oral swab that collects oral fluid, leaving a central area into which the dilution port may be depressed (FIGS. 10C and 11) to isolate the portion of saturated swab fabric to be used in the test.

FIG. 12A is a bottom plan view showing the placement of particulate marker pads 7 in relation to the exit of central channel 25 (FIG. 7A) from the bottom of midpiece through exit region 27 of the midpiece (FIG. 7C). FIG. 12B is a bottom plan view showing the overlap region (dotted line) between the particulate marker pads 7 and the diluted sample membrane 8. FIG. 12C is a 2× right view of midpiece 6 showing the orientation of the diluted sample membrane 8 to the particulate marker pads. When diluent fluid is introduced under pressure in flow direction 1 (FD1, FIG. 12C) through the isolated membrane 26 centripetal to o-ring 5, it removes sample from the isolated membrane and the diluted sample passes through the midpiece and exits from the bottom of the midpiece where it comes into contact with diluted sample membrane 8. From a central location on diluted sample membrane 8, it flows outward in flow direction 2 (FD2, 12C) to come into contact with particulate marker pads 7 for each flowpath. FIG. 12D is a 2× front view of the device that demonstrates the overlap between diluted sample membrane 8 and particulate marker pad 7, between particulate marker pad 7 and nitrocellulose membranes 9 or 10, and between nitrocellulose membranes 9 or 10 and absorbent pads 11. Flow direction 3 (FD3, FIG. 12D) for the diluted sample is from diluted sample membrane 8 up and across particulate marker membrane 7, downward from particulate marker 7 into nitrocellulose membrane 9 or 10, across these nitrocellulose membranes and finally upwards again into absorbent pads 11 at the downstream end of each nitrocellulose membrane.

Figure 8:
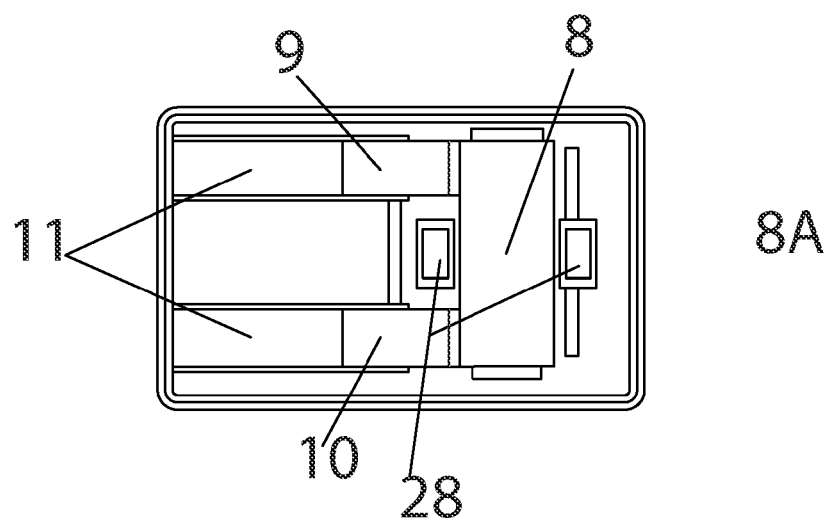
FIGS. 8A, 8B, and 8C are top plan, perspective and front views of the base (FIG. 1, 12).
Figure 8:
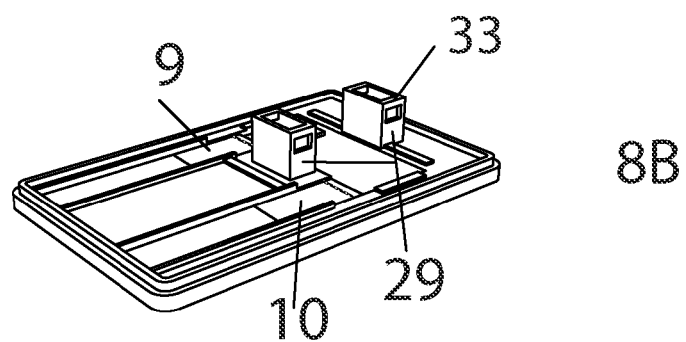
Figure 8:
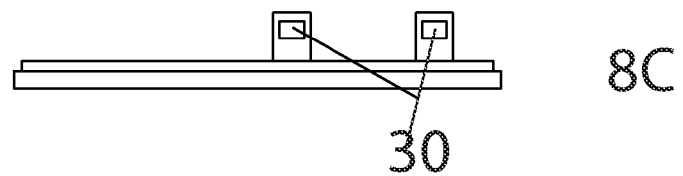
Figure 9:
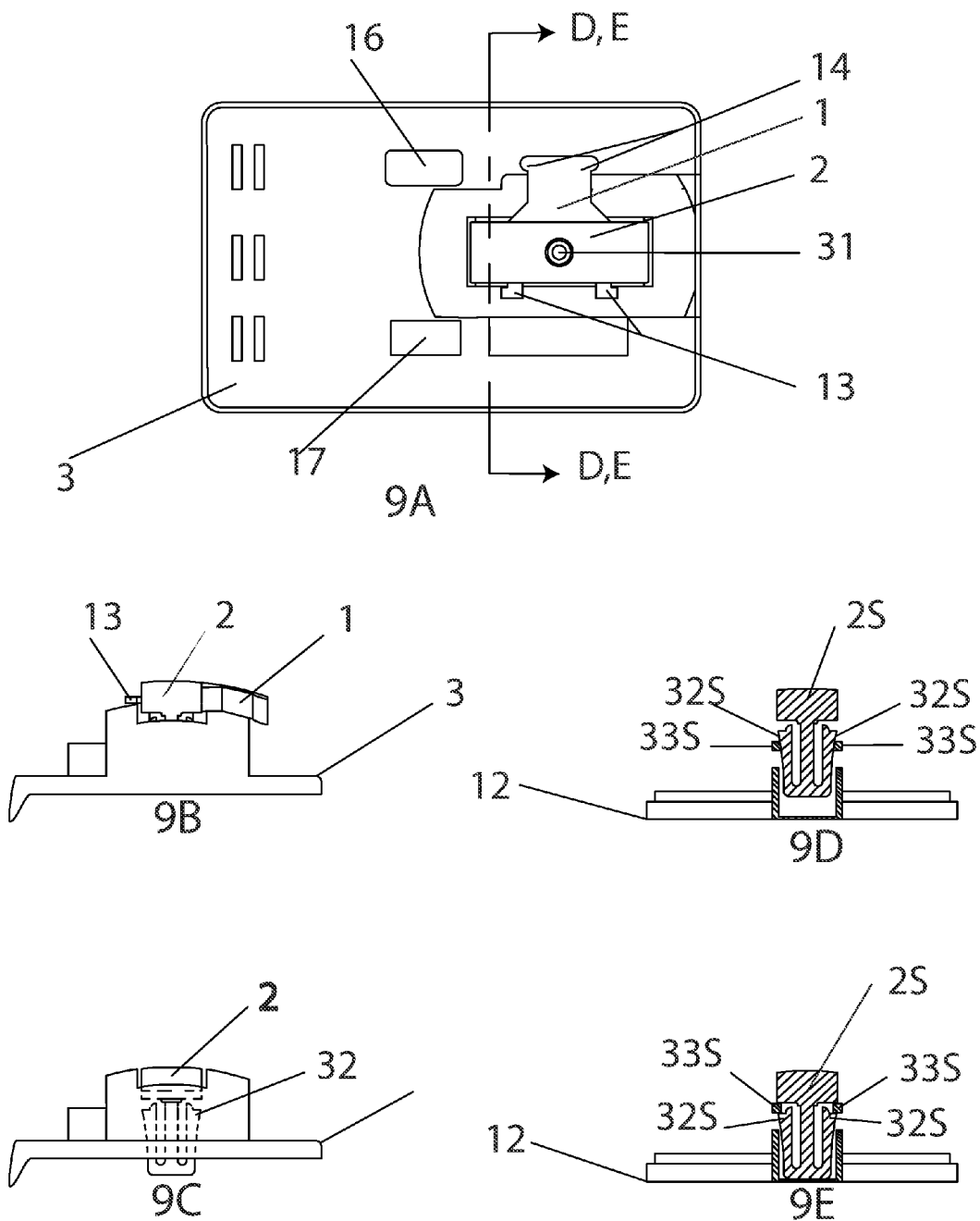
FIG. 9 further illustrates how the dilution port (2) inserts into the base (12).
Figure 12:
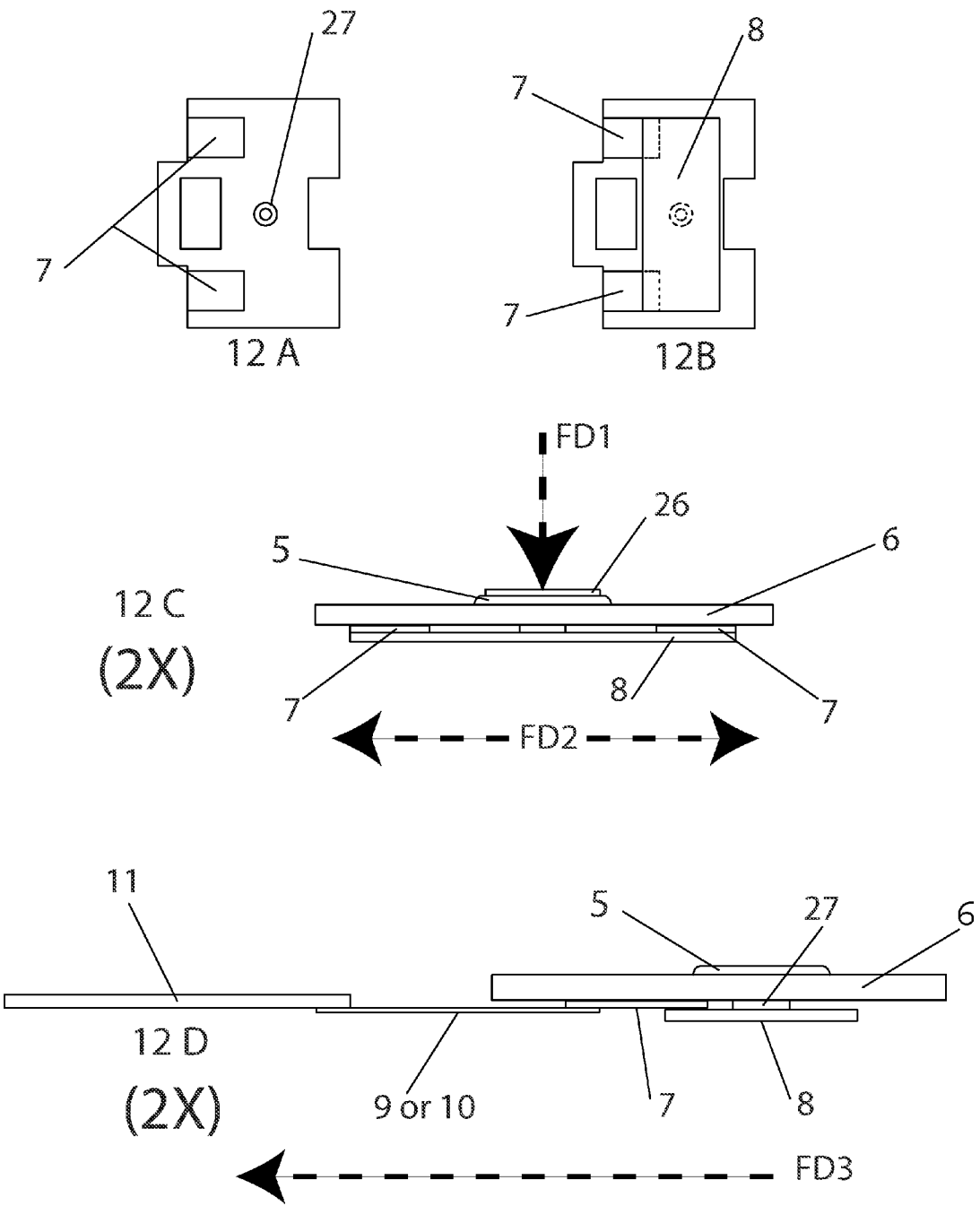
FIG. 12 illustrates the position of membranes of the test devices in relation to the midpiece.
Figure 13:
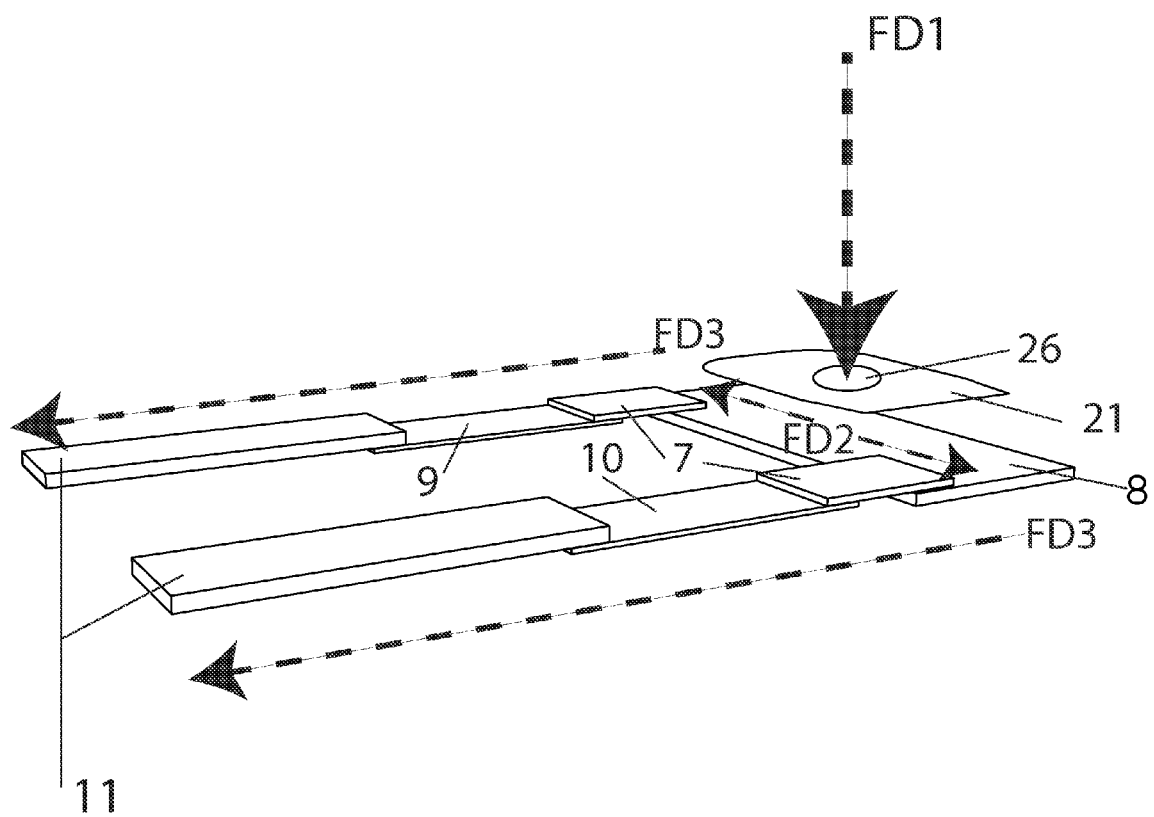
FIG. 13 further illustrates the flow directions of running buffer and diluted liquid sample during use of the device to detect specific antibodies or analytes in oral fluid. In this figure, the midpiece and base are removed and only membranes of the test are displayed, each in its correct orientation as it exists within the medical devices of this application. The sample membrane (21) sits on top of the midpiece (not shown in this figure, see 6, FIG. 12) and once the sample membrane has been saturated with the liquid to be tested, a defined area of that saturated sample membrane (26) is isolated according to U.S. Pat. No. 7,364,914, B2, Buchanan. The isolated area of saturated membrane is centripetal to a perimeter of compression of the membrane formed by an o-ring within the midpiece (5, FIG. 12) pressing on the undersurface of the membrane, and opposing matching inferior surfaces of the dilution port (37, FIGS. 2B and 2C, and 37S, FIG. 10B) compressing the top surface of the membrane. Flow Direction 1 (FD1, FIGS. 11, 12, and 13) occurs when test running buffer is delivered under pressure through the central channel of the dilution port (36, FIG. 10C), through the isolated portion of the saturated membrane containing the sample (26S, FIG. 11), through channel 25 within the midpiece (FIG. 7A) and out the inferior opening of the midpiece located beneath the isolated membrane (27S, FIGS. 10C and 27, FIGS. 12A, 12D). The sample is removed from the membrane and diluted and dropped onto the diluted sample membrane (8, FIGS. 1, 8A, 12B-D, 13, and 8S, FIG. 11). Entry of the diluted sample in the diluted sample membrane initiates flow direction 2

(FD2, FIGS. 12C and 13) which transfers the fluid from the central portion of this membrane to its periphery which allows contact with the particulate marker pads located on the undersurface of the midpiece (7, FIGS. 1, 12A-D, 13) to initiate flow direction 3. Flow direction 3 (FD3, FIGS. 12D and 13) occurs in two or more flow paths, one to confirm immunoreactivity of all critical test reagents (results displayed on membrane 10 (FIGS. 1,8& 13) through cover window 17 (FIGS. 5A and 9A) and an additional one or more paths to detect specific antibodies if present and also confirm sample adequacy (results displayed on membrane 9 (FIGS. 1, 8, and 13) through cover window 16 (FIGS. 5A and 9A). Flow direction 3 transfers the diluted liquid sample by capillary flow fluid communication and membrane wicking from the upstream portion of each flow path which includes mobilizable dried reagents on the particulate marker pads (7, FIGS. 1, 12A-D and 13) into the downstream portion of each flow path that consists of a nitrocellulose membrane containing immobilized antigen and an additional reagent to evaluate sample adequacy in the sample adequacy and specific antibody detection flow path. The final downstream portion of each flow path is an absorbent pad that collects all the excess running buffer and any unbound components of the diluted sample and mobilized reagents used in the test. The absorptive capacity of this pad dictates that fluid added to the diluted sample membrane (8, FIGS. 1,8A, 12B-D, 13) will end up in the absorbent pad and that the overall test flow directions will be upstream to downstream along a path of diluted sample membrane leading to particulate marker pad to nitrocellulose membrane and finally to the absorbent pad.

Figure 14:
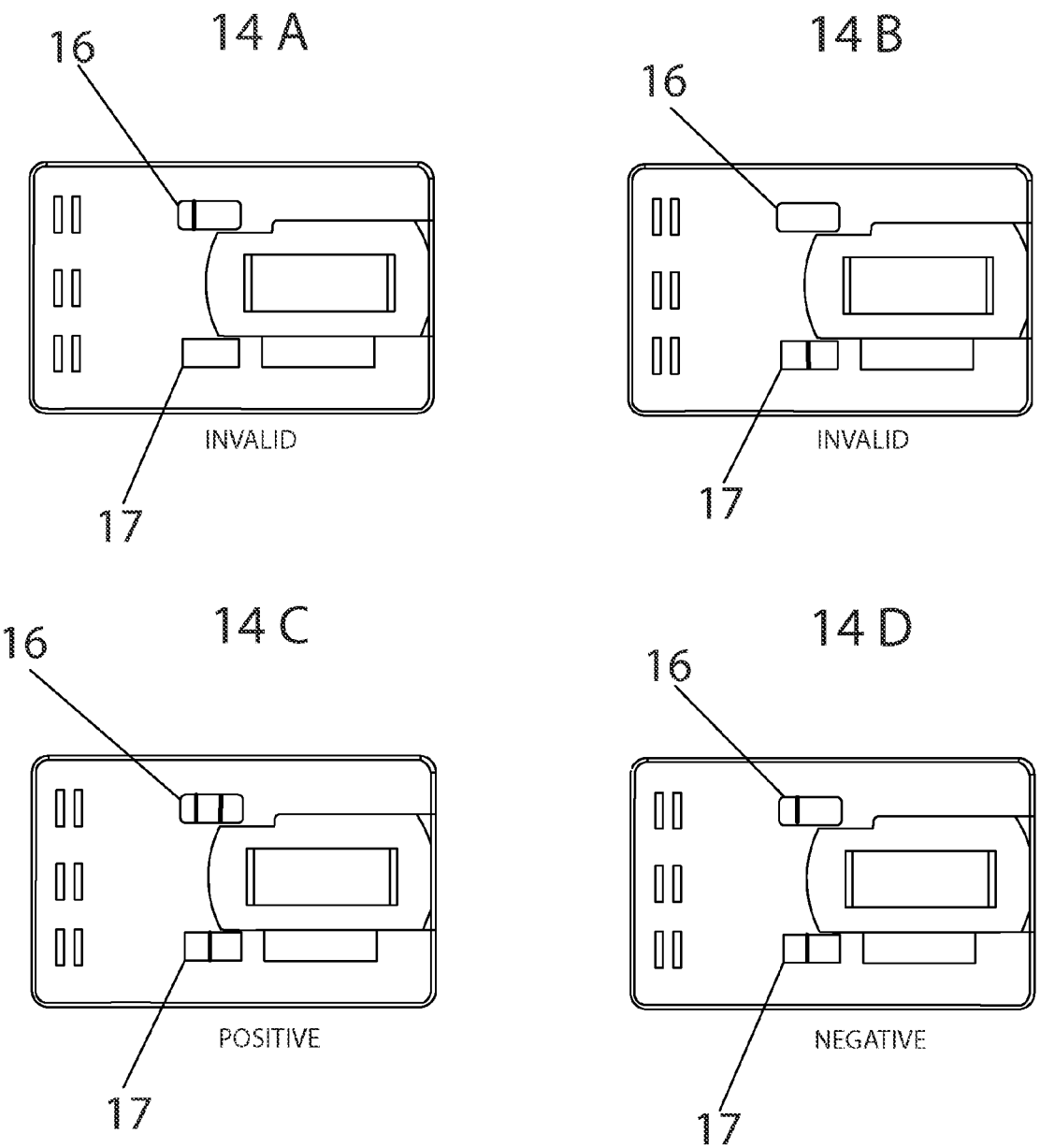

FIG. 14 shows top plan views of the test device cover. Results that may occur with the rapid lateral flow test methods and devices of this invention are shown in FIGS. 14A-14D. The detailed description and interpretation of these results is found in Example 7.

FIG. 14A shows absence of a line demonstrating binding of particulate marker to immobilized antigen in window 17 of the cover, over the reagent control pathway. This indicates failure of critical test reagents. There is no line of binding to antigen in the specific antibody and sample adequacy pathway viewed through window 16 of the cover, and a line exists further downstream to indicate that the sample tested contained adequate immunoglobulin for evaluation.

FIG. 14B shows a line demonstrating binding of particulate marker to immobilized antigen in window 17 of the cover, over the reagent control pathway. This indicates that the critical test reagents are working. Window 16 over the pathway to test sample adequacy and to test for antibody to specific antigens shows no line of binding to specific antigen and also fails to show binding of particulate marker the Ig binder rPA immobilized further downstream in the same path. The lack of binding to immobilized rPA indicates that the sample tested contained insufficient immunoglobulin for evaluation.

FIG. 14C shows a line of particulate marker binding to immobilized antigen in window 17 of the cover, over the reagent control pathway, and also shows in window 16 of the cover a line of particulate marker binding to the Ig binding reagent rPA immobilized downstream in the sample adequacy pathway. These lines indicate that sample is adequate for testing and that all critical reagents are working. There is no line of binding of particulate marker to antigen in the specific antibody and sample adequacy pathway viewed through window 16 of the cover.

FIG. 14D shows a line of particulate marker binding to immobilized antigen in window 17 of the cover, over the reagent control pathway, and also shows in window 16 of the cover a line of particulate marker binding to the Ig binding reagent rPA immobilized downstream in the sample adequacy pathway. These lines indicate that sample is adequate for testing and that all critical reagents are working. There is a line of binding of particulate marker to antigen in the specific antibody and sample adequacy pathway viewed through window 16 of the cover.

Figure 15A:
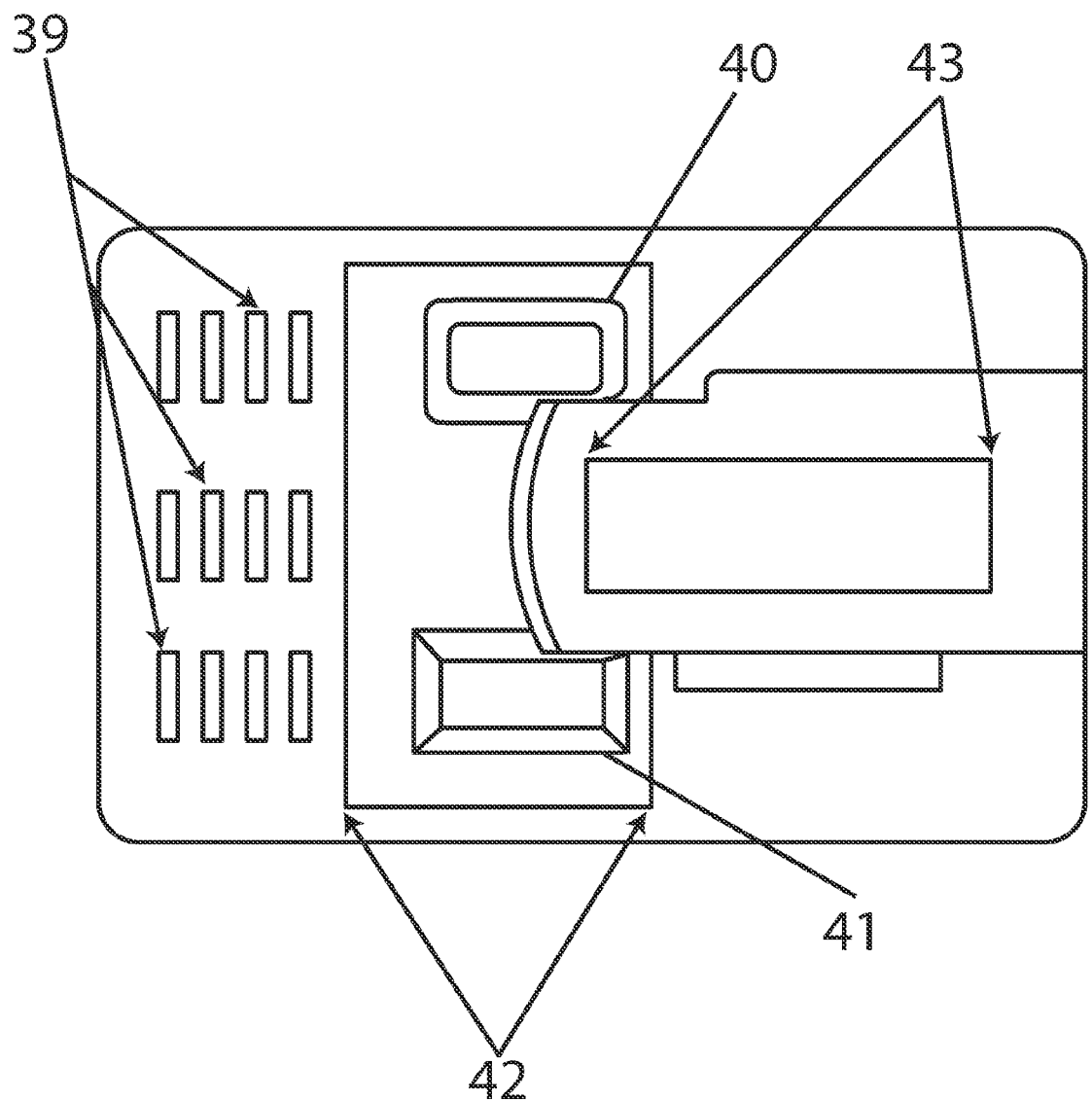

FIG. 15A is a top plan view of a revised cover device design for use with modifications that provide improved test sensitivity, longer reading windows and lack of backflow of test reagents. It contains a larger opening (43) for the dilution port (2, FIG. 1), increased ventilation areas (39) to speed evaporation of test running buffer and diluted sample, tapered windows (40 and 41) to assist reading and interpreting results for the positive reagent and sample adequacy pathway (window 40) and the specific antibody detection pathway (window 41), and an indented area (42) into which may be placed a protective polyester cover for the test device strips upon which may be printed desired labeling to assist identification and interpretation of test results.

FIGS. 15B-15E illustrate representative results that may be obtained using the device designs of this invention. In these figures, the reagent reactivity and sample adequacy pathway results are shown in window 40 with rounded edges, and the specific antibody detection results are shown in rectangular window 41.

FIG. 15B shows a line to indicate sufficient immunoglobulin in the reagent positive control and sample adequacy pathway, but no line of particulate marker over the immobilized antigen. This indicates failure of the immobilized antigen, the particulate marker or the upstream mobilizable monoclonal antibody to the immobilized antigen of interest and the test result must be interpreted as INVALID.

FIG. 15C shows a line of particulate marker over the immobilized antigen in the reagent positive control and sample adequacy pathway, which indicates that antigen, particulate marker, and monoclonal antibody to the immobilized antigen are immunoreactive. However, there is no line of particulate marker over the immobilized recombinant protein A. This indicates failure that the sample being tested contained insufficient amounts of immunoglobulin to allow detection of antibodies specific to the immobilized antigen to be detected if present, and the test result must be interpreted as INVALID.

FIG. 15D shows lines of particulate marker binding over the immobilized recombinant protein A (44) and over the immobilized antigen (45) as read through the window overlying the reagent positive control and sample adequacy pathway. This indicates that the test is functioning properly and the absence of any line of particulate marker binding to immobilized antigen in the rectangular window over the specific antibody pathway indicates that the diluted sample contains no antibodies specific to the immobilized antigen and the test result may be correctly interpreted as NEGATIVE.

FIG. 15E shows lines of particulate marker binding over the immobilized recombinant protein A and over the immobilized antigen in the reagent positive control and sample adequacy pathway. This indicates that the test is functioning properly and the presence of a line of particulate marker binding to immobilized antigen in the rectangular window over the specific antibody pathway indicates that the diluted sample contains antibodies specific to the immobilized antigen and the test result may be correctly interpreted as POSITIVE.

Figures 16A, 16B:
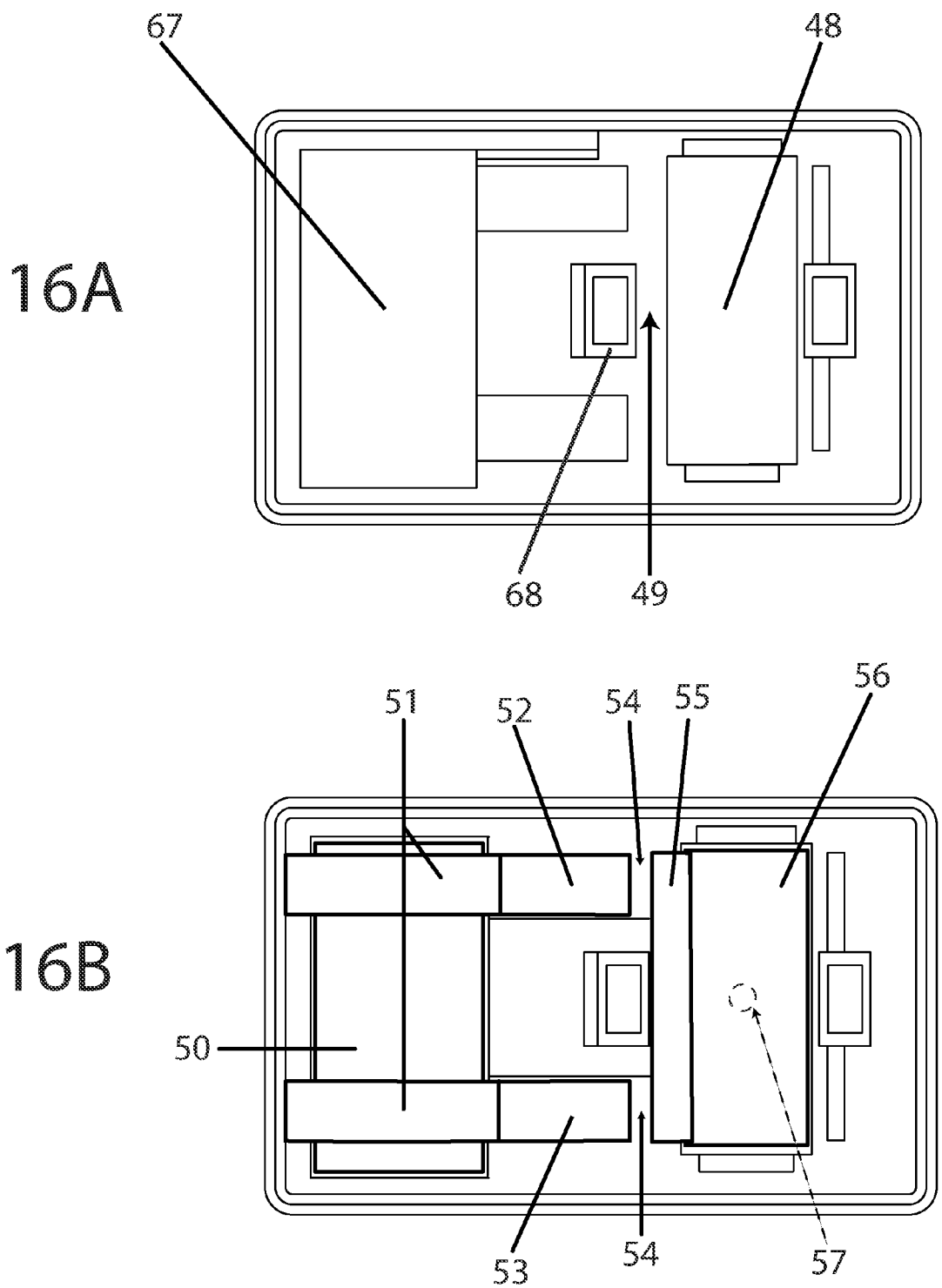

FIG. 16A is a top plan view of a revised base design that provides a large well (67) capable of holding an absorbent pad that can hold 1.1 ml of liquid (50, FIG. 16B). This large absorbent pad reservoir ensures that fluid flow direction is from the upstream point of entry into each flow path, flowing downstream over each flow path and terminating in this pad, and that backflow of pad contents into the viewing windows of the test device is prevented as described in Example 9. The spacing of the most central base receptacle (68) for the dilution port that has been moved in the revised base 3 mm closer to the absorbent pad well (67). This provides 3 mm of extra space (49) on the downstream side of diluted sample well (48) that is outside of and adjacent to the diluted sample well and allows use of a modified particulate marker pad (55, FIG. 16B) with resulting increased test sensitivity as described in Examples 10 and 11.

FIG. 16B is a top plan view of the revised base design with membranes of the rapid test in place, except for bridging membranes that connect the nitrocellulose strip of control (52) and test (53) membranes across gap (54) between them and a particulate marker pad (55) that has been modified to perform tests with increased sensitivity as described in Examples 10 and 11. The particulate marker pad (55) sits predominantly on a plastic shelf adjacent the diluted sample membrane (56) and its upstream edge overlaps the diluted sample membrane by 1-2 mm. The diluted sample membrane is held within a well designed for it in the base (48, FIG. 16A). Nitrocellulose membranes of the reagent positive control and sample adequacy pathway (52) and specific antibody pathway (53) overlap on their downstream with outflow wicks (51) connecting the nitrocellulose strips to the absorbent pad (50).

Figure 16C:
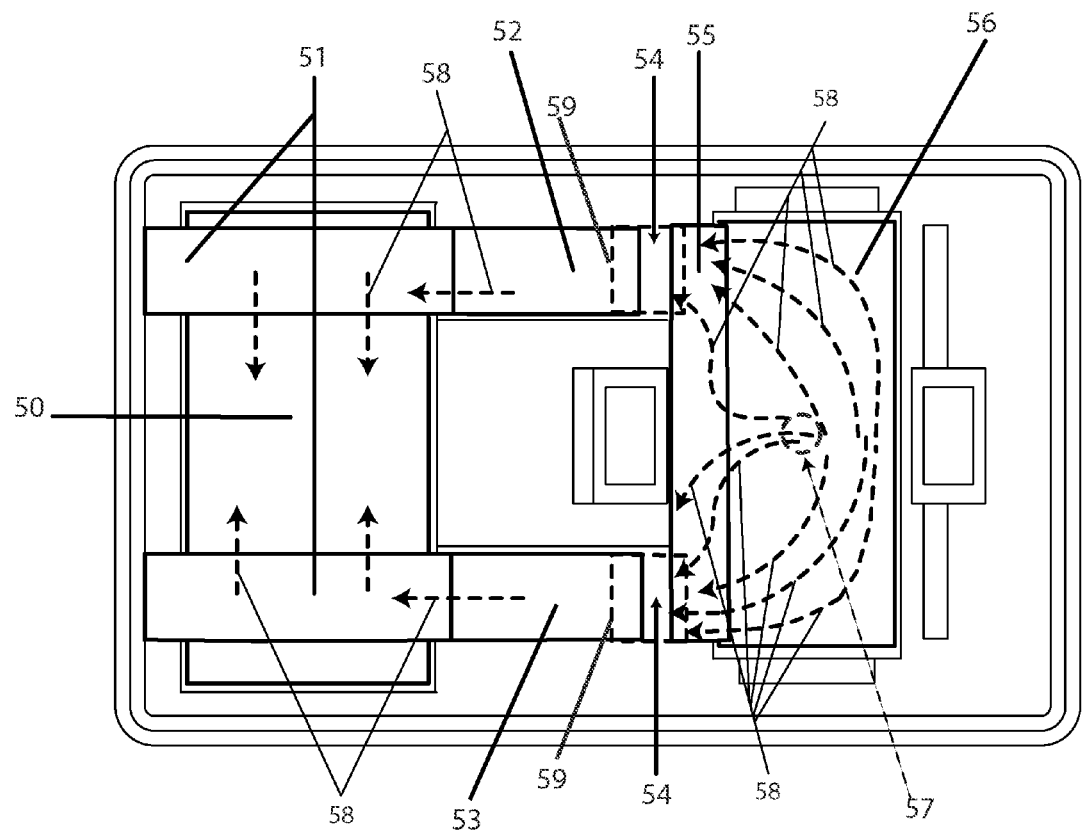
Figure 16D:
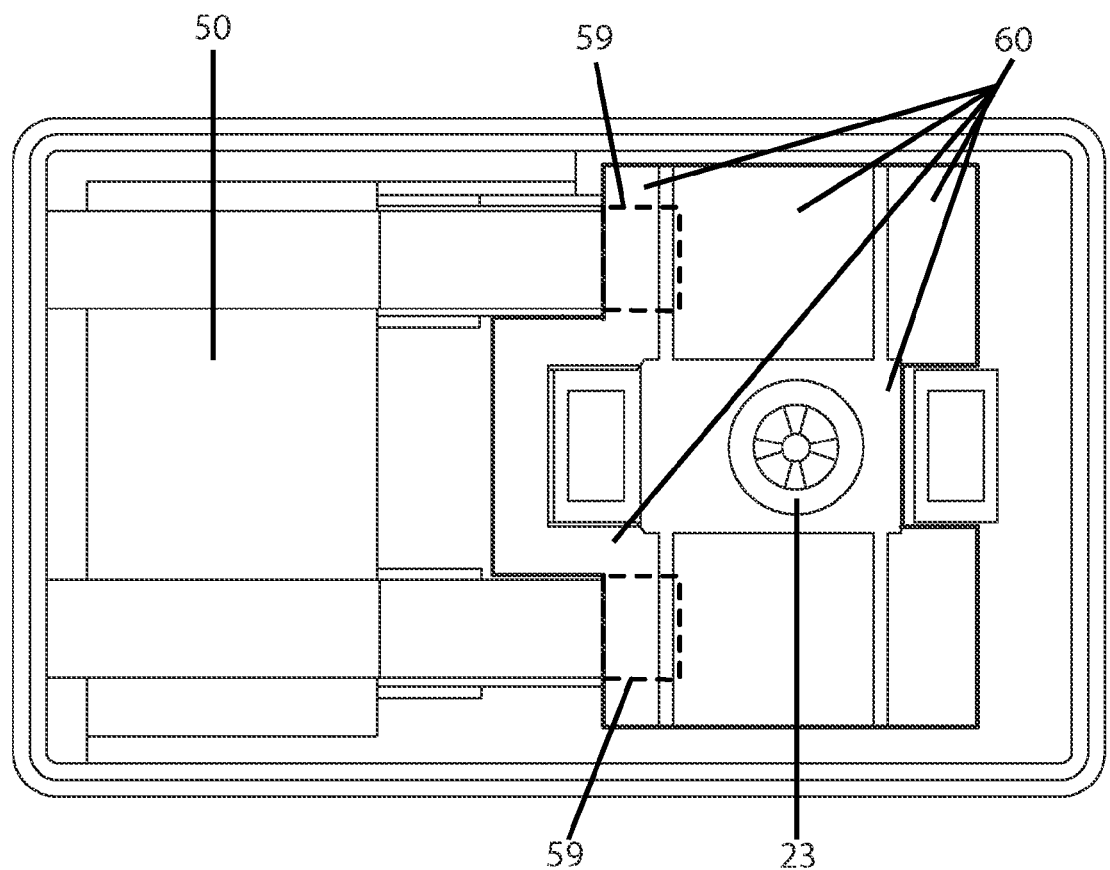

FIG. 16C is similar to FIG. 16B except that bridging membranes (7, FIG. 12) represented by dashed lines 59 in FIGS. 16C and 16D cross gap 54 (FIG. 16C) between upstream diluted sample membrane 56 and downstream nitrocellulose membranes when the midpiece (60, FIG. 16D) is placed into the device so that bridging membranes (59, FIG. 16D) are positioned as shown. These bridging membranes allow fluid communication between particulate marker pad 55 (FIG. 16C) and nitrocellulose membrane of control pathway 52 (FIG. 16B) and specific antibody pathway 53 (FIG. 16B) when wet by diluted sample during test performance.

FIG. 16D shows the revised base of FIG. 16A with the membranes of FIG. 16B in place along with midpiece 60 of FIG. 16C with bridging membranes (dashed lines 59, FIGS. 16C and 16D) attached to the undersurface of the midpiece. FIG. 16D also shows o-ring 23 located within its groove in the upper surface of midpiece 60. This o-ring facilitates isolation of an area of saturated sample membrane centripetal to the o-ring when the membrane is compressed on its undersurface by the o-ring and on its top surface by the bottom of the dilution port as described in U.S. Pat. No. 7,364,914 B2, Buchanan.

Once diluted sample is created within the test device during test performance as described in Examples 5 and 6, the fluid migrates by capillarity through the membranes from upstream diluted sample membrane 56 to downstream absorbent pad 50 as shown by dashed lines 58 of FIG. 16C. The dashed circle 57 of FIGS. 16B, C, E, and F shows the area on the undersurface of the midpiece from which the diluted sample enters the diluted sample membrane.

Figure 16E:
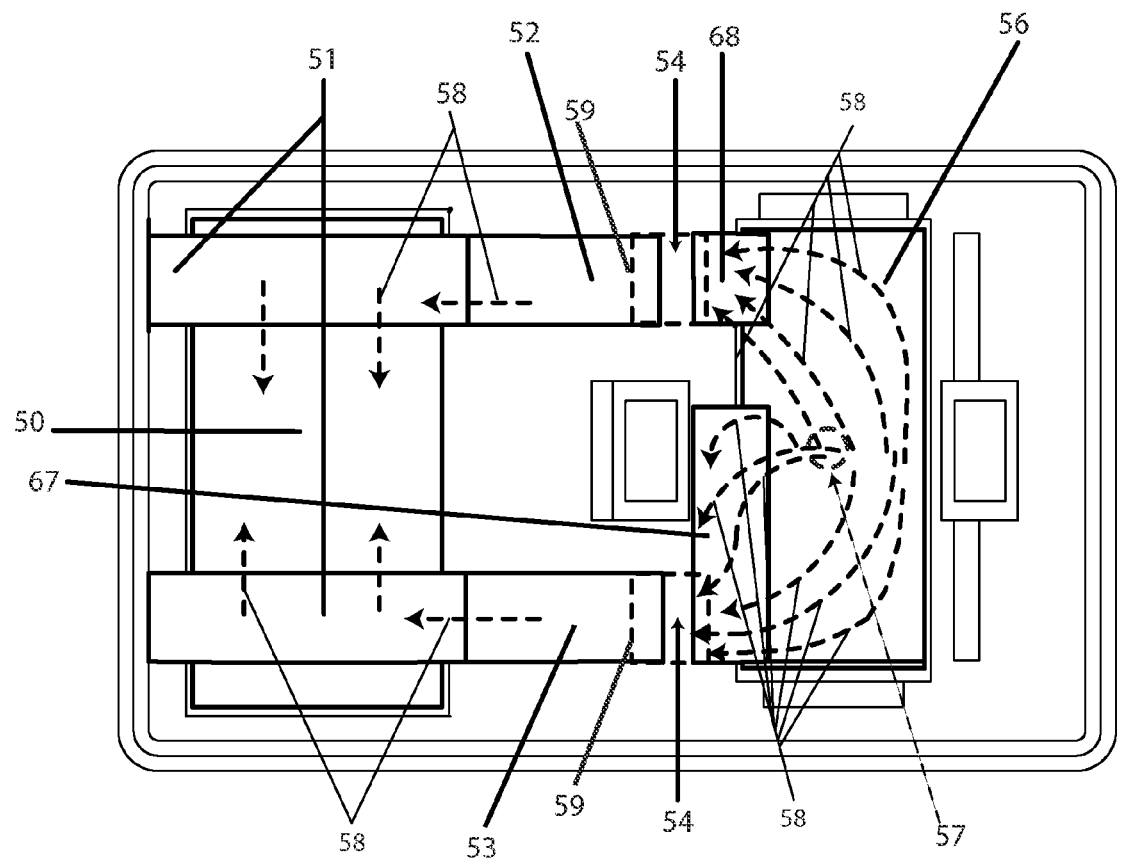

FIG. 16E illustrates the flow patterns (dashed lines 58) for movement of diluted sample into two flow paths, each with a different size and orientation of the particulate marker membrane. Flow path 52 is the sample adequacy and positive reagent reactivity control pathway and in this illustration the particulate marker pad (68, FIG. 16E) is of conventional size and orientation design. The conventional particulate marker pad for this pathway is the same width as the width of the downstream pathway membranes. The flow path 53 (FIG. 16E) for detection of specific antibody contains a new generation particulate marker pad (67, FIG. 16E) that overlaps the diluted sample membrane along one edge and allows a greater range of concentrations of sample to interact with particulate marker as explained in Example 10 and FIG. 16F, and also provides particulate marker to the developing lateral flow immunoassay over a longer time period during test result development (Example 10). Together, these changes result in higher sensitivity of the rapid immunoassay as compared to conventional lateral flow rapid test designs (Example 11).

Figure 16F:
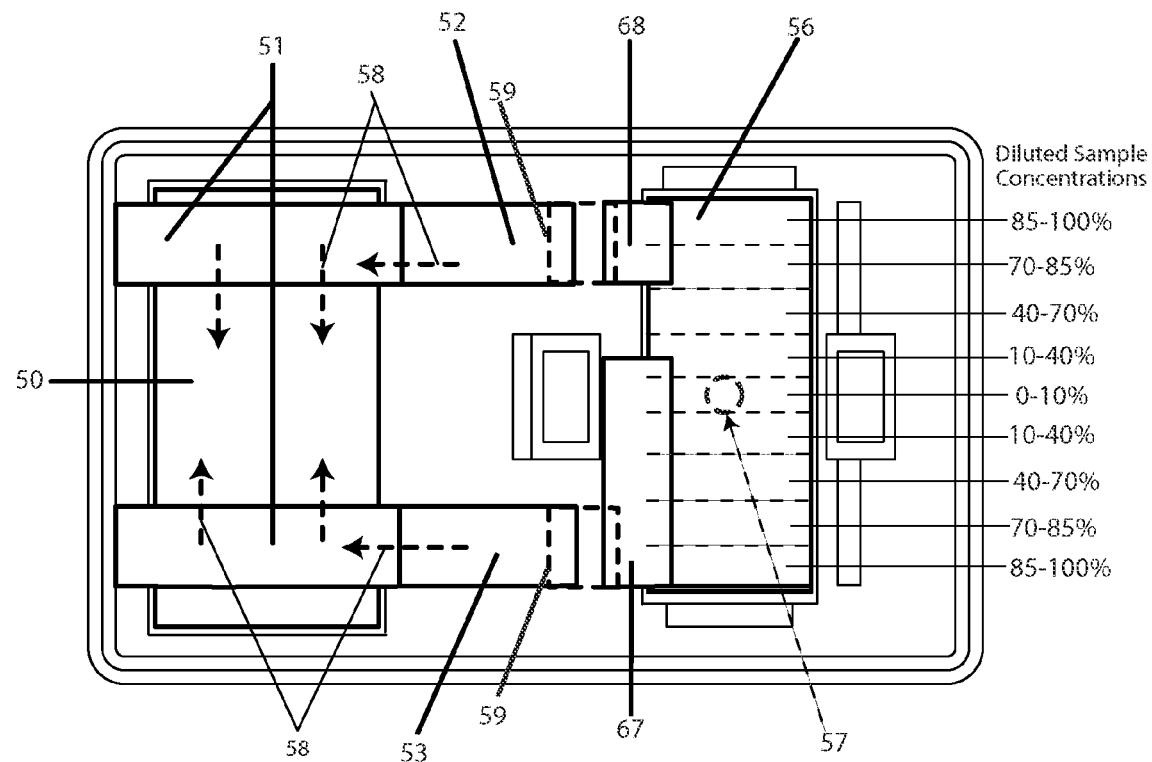

FIG. 16F illustrates how particulate marker pads of the invention (67, FIG. 16F), are oriented to the diluted sample membrane (56, FIG. 16F) with a slight overlap. The diluted sample concentrations obtained by the devices of the invention are preserved within the membrane in a range from highest concentrations near the ends of the membrane to lowest concentrations near the entry point to the membrane from the midpiece isolated sample (57, FIGS. 16B, D, E, and F, and Example 10). This overlap provides a relatively constant amount of particulate marker to interact with sample dilutions ranging from as low as 0-10% to as high as 85-100%. During test development with the invention, the first marker-sample interactions to enter the downstream flow path are those with highest concentrations of sample (FIG. 16F). Next, sample concentrations 40-70% of those that initially entered the downstream path, that have been incubating with particulate marker in a higher ratio of marker to sample arrive at the upper end of the specific antibody flow path and migrate downstream (FIG. 16F). Finally, combinations with the highest ratios of marker to sample (constant marker combined with sample at 10-40% of most concentrated, see Example 10) reach the entry to the specific antibody flow path and flow over its downstream components.

Figure 11:
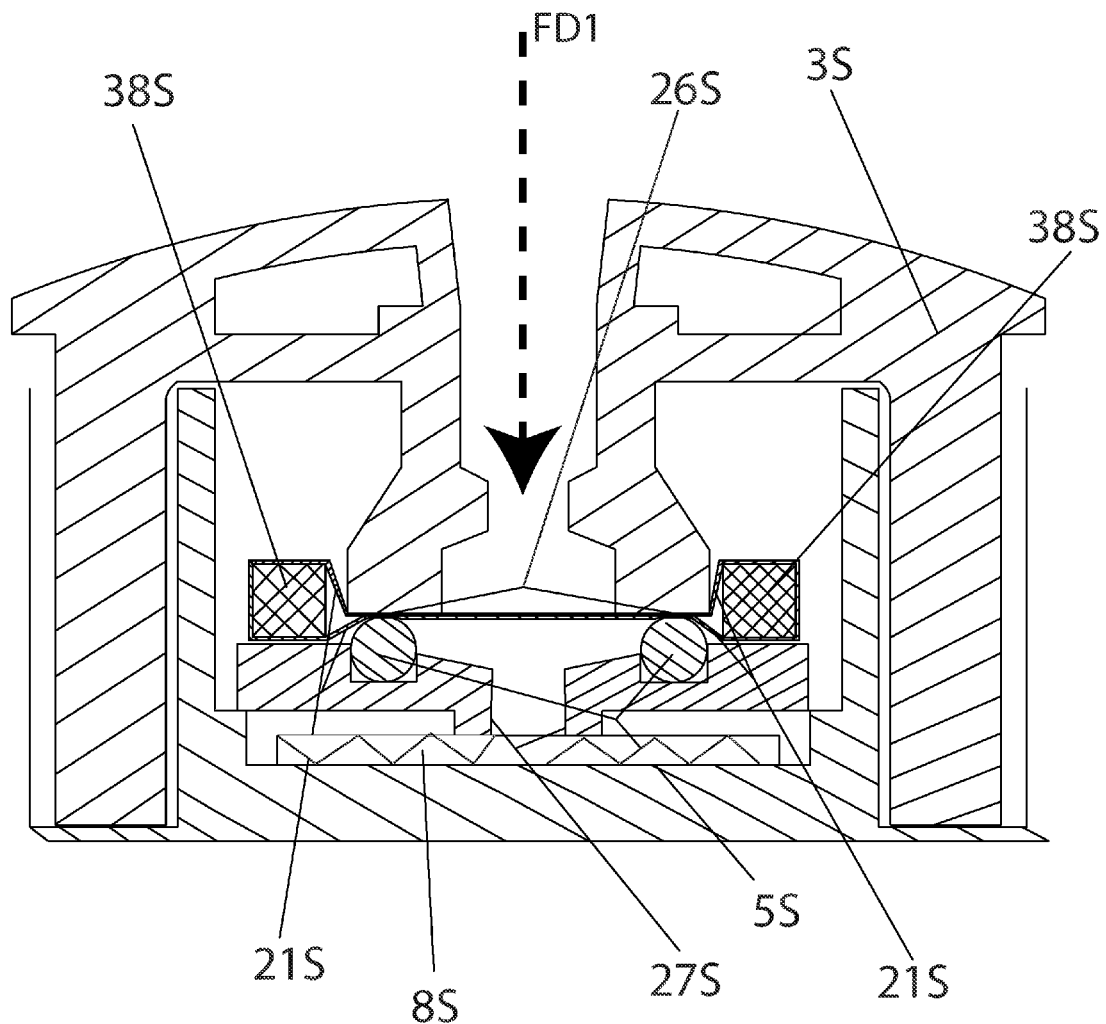
FIG. 11 is an enlargement of FIG. 10C. It shows cross sectional area of compression of the swab membrane, and also illustrates the location of the diluted sample membrane (8S) relative to the midpiece.

In contrast to the varied concentrations of sample to marker tested with the invention, the particulate marker pad of conventional design (68, FIG. 11F) interacts only with the highest concentrations of diluted sample in the range of 70-100% of highest concentrations, and thereafter no particulate marker is available to interact with diluted sample as it migrates down the flow pathway (pathway 52, FIG. 16F).

When conventional particulate marker pads (68, FIG. 11F) were compared to the particulate marker pads of the invention (67, FIG. 11F), it was found that particulate marker was delivered to the assay 3 times longer with the new design and orientation than with conventional in-line particulate marker pads (Example 10). The new designs and orientations of particulate marker pads in this invention provided a 5 to 10 fold increase in sensitivity for detection of specific antibody when compared to conventional lateral flow immunoassays employing in-line marker pads (Example 11).

Figure 17A:
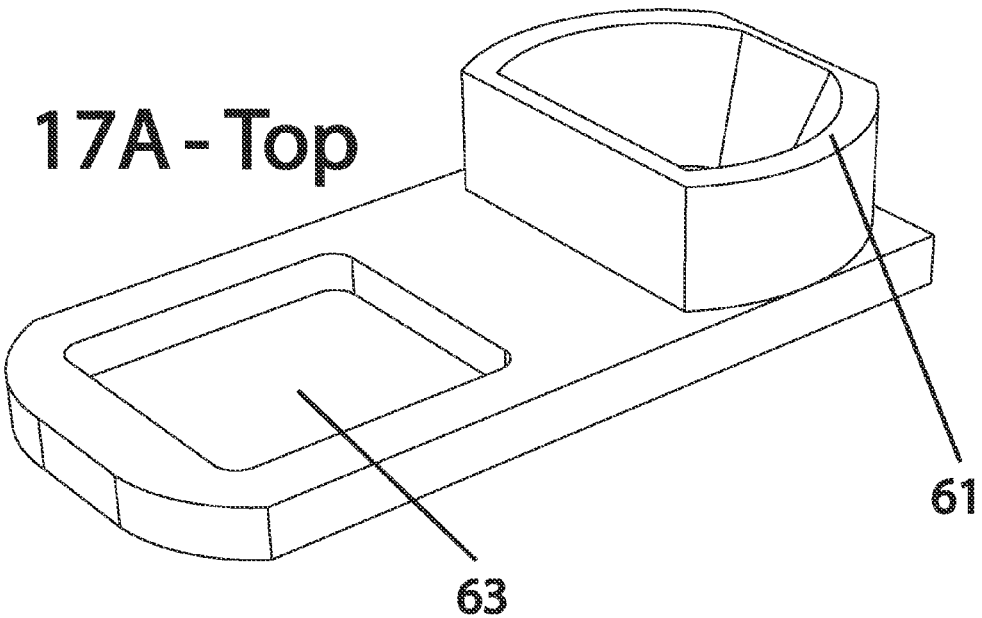
Figure 17B:
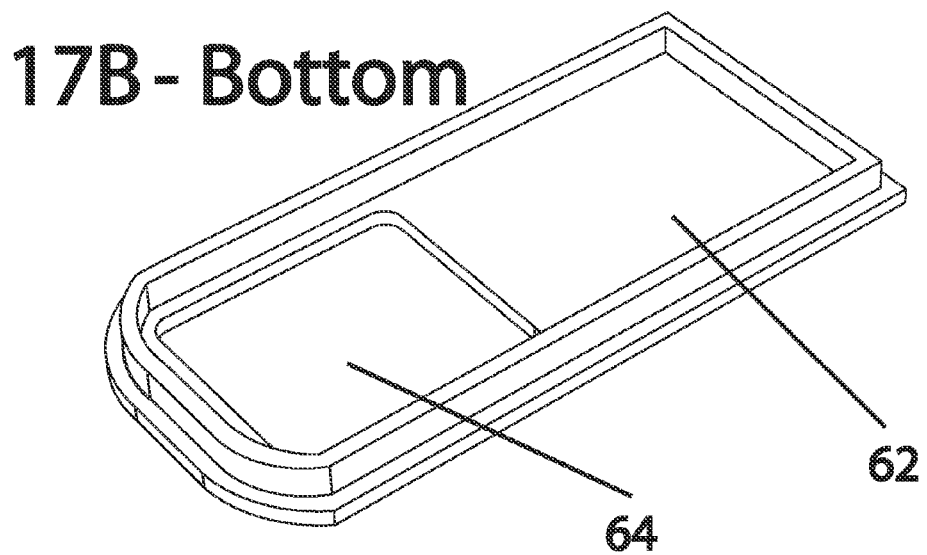

FIG. 17A is a 2D perspective view of the top portion of the insert, and FIG. 17B is a 2D perspective view of the bottom portion of the insert. A membrane such as LF1 (GE Whatman, Florham Park, N.J., USA), cut to the precise size of the inner margin of the insert bottom, sits on platform 62 and is held in place within the insert by compression between the top and bottom portions of the insert. When 2 drops of fingerstick or venipuncture whole blood are placed directly into funnel-like portion 61 (FIG. 17A) of the test device insert, the blood flows onto the LF1 membrane and then over a 4 minute period migrates to the opposite end of the membrane with acellular serum or plasma components preceding the more slowly migrating cellular components. A portion (66, FIG. 18) of the LF1 membrane saturated with acellular components of the whole blood sample may then be isolated and diluted by the method of Buchanan (U.S. Pat. No. 7,364,914 B2).

Figure 10:
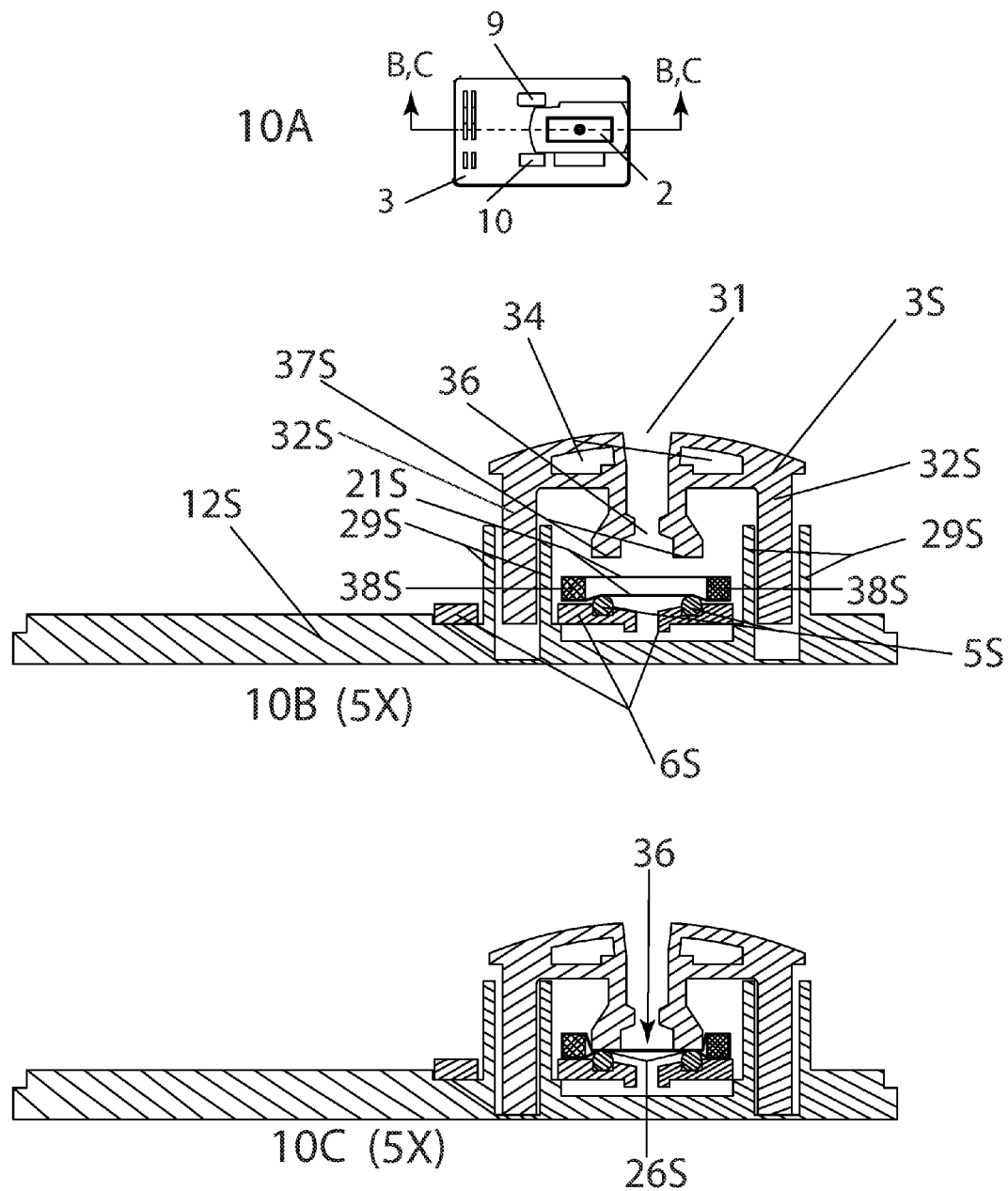
FIG. 10 illustrates how an area of swab fabric once saturated with oral gingival crevice fluid is isolated and used to produce the diluted sample analyzed by the test device.
Figure 18:
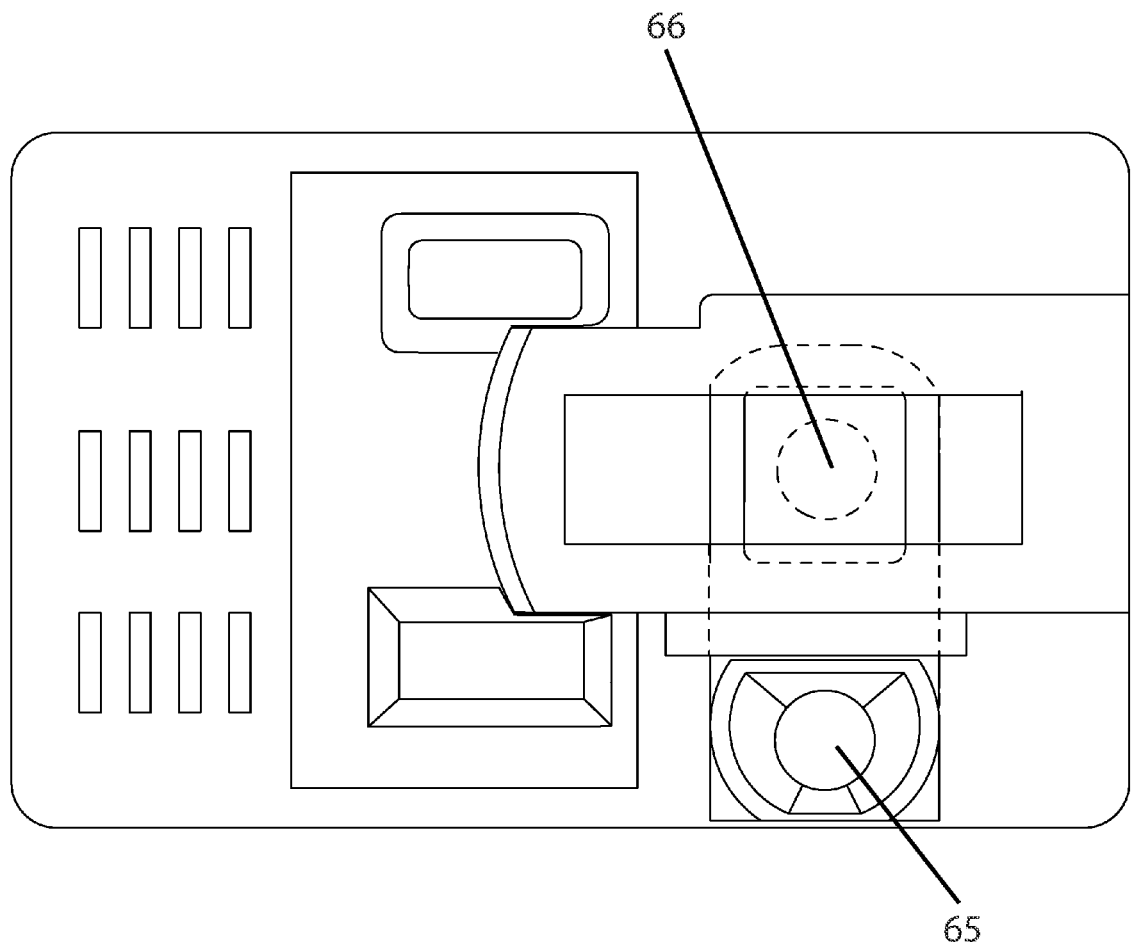

FIG. 18 shows the assembled whole blood insert in place within the revised cover. When two drops of whole blood are introduced onto the LF1 membrane at position 65, the acellular portion of blood migrates to and beyond position 66 within 4 minutes. When the dilution port is pushed down and locked into place, the area of LF1 membrane saturated with acellular-enriched whole blood is then isolated between the bottom surface of the dilution port and the o-ring in the upper surface of the midpiece (FIG. 10C). When running buffer is then applied through the dilution port opening under pressure, the acellular-enriched whole blood is simultaneously removed from the isolated portion of saturated LF1 membrane and diluted and delivered to the diluted sample membrane (56, FIG. 16C and from there flows downstream from one end into the absorbent pad over the reagent positive control and sample adequacy pathway, and from the other end into the specific antibody pathway, as illustrated by dashed lines 58 of FIG. 16C.

DETAILED DESCRIPTION OF THE INVENTION

A specific description of how the methods and devices of this application allow determination of sample adequacy is provided in Example 3 and Table 1 below. The basic approach was to discover conditions of a rapid lateral flow immunoassay capable of providing a qualitative indication of the presence of immunoglobulin in the liquid sample being tested, the absence of which indicates that the sample is inadequate for detecting antibodies specific to a given antigen, since the specific antibodies of interest would be a sub-fraction of the immunoglobulins detected by the sample adequacy test.

There are many potential user errors that might contribute to testing a sample that contained inadequate amounts of immunoglobulin, and the absence of a built-in control to detect this type of error might lead the user to falsely conclude that the test result was negative, rather than realizing that the collected sample was inadequate. For example, in the oral fluid test, instead of collecting oral fluid from the gingival crevice at the teeth-gum line, the user might simply collect saliva onto the swab, or collect moisture from the mucosal lining of the cheeks. Alternatively, the location of collection might be correct but the time insufficient, such as collecting the sample in 3 seconds rather than 30 seconds each over the teeth-gum line junction. These errors would produce a fluid with far less immunoglobulin on the swab fabric than is present in a properly collected sample. For the whole blood test using finger-stick or venipuncture blood, the first portion of the assay is migration of the blood along a membrane that slows migration of the cellular components and leaves an area of serum or plasma at the leading edge of the saturated membrane that is then sampled by the dilution port to o-ring perimeter compression method to isolate a non-compressed portion of membrane saturated with serum or plasma for testing (see Ahlstrom CytoSep or GE-Whatman LF1 membranes, and U.S. Pat. No. 7,364,914 B2). This initial migration along the blood sample collecting membrane requires 4 minutes to provide a leading edge of serum or plasma containing depleted cellular components that is ready for dilution and testing. If the user decides to depress the dilution port into the locked position and pass running buffer through the locked dilution port to perform the test after waiting for only 3 minutes or less, insufficient migration will have occurred to provide an adequate sample. This will be detected by the sample adequacy control methods described in Example 3 allowing the correct interpretation that the test is invalid. The absence of such a control means that this type of user error would not be detected and that the test result might be falsely interpreted as negative, rather as an invalid test that requires repeating to obtain an answer.

In theory, many of the combinations presented in Table 1 would reasonably be expected to work for confirming the presence of immunoglobulin in the test samples. In practice however, under the conditions described herein and with membranes in common use in many lateral-flow immunoassays, it was observed that only one of the 13 different combinations evaluated produced a line when immunoglobulin was present in the test sample, and no line when only the sample diluent without immunoglobulin was tested. Each of the 12 other combinations produced a line at the most downstream end of the test strip where the IgG binding reagent was immobilized on nitrocellulose even when no IgG was present in test sample. This non-specific line was nearly equivalent to the line resulting from test samples that contained immunoglobulin.

The observation from these experiments was that non-specific binding occurs between most Ig binding reagents bound to colloidal gold when exposed to other Ig binding reagents immobilized on nitrocellulose downstream (12 examples). In contrast, when recombinant protein A (Repligen Corporation, Waltham, Mass.) was immobilized on nitrocellulose it retained its ability to recognize IgG in samples containing IgG bound to protein L colloidal gold and protein G colloidal gold (BioAssay Works, Ijamsville, Md.) when both of these colloidal gold reagents migrated past it from upstream to downstream, but failed to non-specifically bind to a mixture of protein L colloidal gold and protein G colloidal gold when they were migrated past the rPA in running buffer containing no IgG (Ig binding reagent line 26 of Table 1). When either protein G or protein L colloidal gold preparations were migrated alone, in running buffer without IgG, past downstream immobilized rPA, they each bound non-specifically to the downstream immobilized rPA. Only the combination of BOTH protein L colloidal gold and protein G colloidal gold failed to bind non-specifically to low concentrations of recombinant protein A to produce a visibly detectable line. The assumption from these results is that colloidal gold preparations of protein G and protein L together block some or most of the non-specific binding sites recognized by immobilized rPA when either colloidal gold protein G or colloidal gold protein L are migrated individually past the immobilized rPA.

Rapid diagnostic tests may also fail to produce an accurate test result if the critical reagents required to produce detection of antibodies to specific antigens have deteriorated due to storage under adverse conditions or past the shelf-life expiration date. Reagent failure can result in false negative results. Current tests do not have built-in controls to test for this possibility. The two most critical components that may fail are (a) antigens immobilized on nitrocellulose that must contain intact antigenic sites that are recognized by antibodies specific to those antigens as they migrate past and (b) Ig binding reagents bound to particulate markers. If the immobilized antigen being used to test for specific antibodies has deteriorated, antibodies specific to this antigen will simply migrate past it in the rapid assay. Without a control for antigen integrity, the lack of a line at the site of immobilized antigen may be falsely interpreted as a negative test. Similarly, no line will result to indicate the presence of specific antibodies if the Ig binding reagents bound to particulate markers are not immunoreactive. These particulate markers will fail to recognize specific antibody in the test sample bound to immunoreactive immobilized antigen, and migrate past. Again, this potentially may result in the false interpretation that no specific antibodies to the antigen being tested are present in the test sample.

This invention provides built-in controls to confirm immunoreactivity of the critical immobilized antigen and of the particulate marker-Ig binding complexes, as well as the immunoreactivity of a third critical reagent, a monoclonal antibody or polyclonal antibodies that specifically recognize the immobilized antigen for which specific antibodies are being detected. This is accomplished by having a pathway dedicated to testing immunoreactivity of the tests critical reagents that is separate from the pathway used to detect antibodies specific to a given antigen, and by using the same antigen or antigens immobilized identically on the downstream portion of both the specific antibody and critical reagent pathways, and by using the same particulate marker-Ig binding reagent complexes dried down identically in mobilizable form onto the particulate marker pads on the upstream portion of both pathways. In addition, the critical reagent pathway contains a mobilizable reagent or reagents, dried onto the upstream portion of the pathway that bind(s) to the specific antigen or antigens immobilized downstream. This or these reagents may be monoclonal or polyclonal antibodies or other molecules that specifically recognize the antigen to which specific antibodies are being detected in the separate specific antibody and sample adequacy pathway, and are also recognizable by the Ig binding reagents bound to particulate markers. Preferentially, this positive control antibody must be stable for as long or longer than the immobilized antigen and the particulate markers bound to Ig binding reagents must also preferentially be stable for as long or longer than the immobilized antigen, when dried in mobilizable form onto the upstream portion the critical reagent pathway. More preferentially the monoclonal antibody or polyclonal antibodies will recognize the same specific antigenic determinants of the immobilized antigen that are recognized by antibodies in the test samples being evaluated. The advantage of having the critical reagent pathway separated from the pathway to detect antibodies to specific antigens is that the antigen recognizing control antibodies could interfere with detection of immobilized antigen by antibodies in the diluted test samples if they were in the same pathway. With two separate pathways, the flow directions of the rapid test (FIG. 13) prevent contamination of the specific antibody pathway reagents with positive control antibodies from the critical reagent pathway.

Example 1 provides specifics of the preparation and use of potent and stable peptide-BSA conjugate antigen that is useful to detect antibodies to HIV.

Example 2 provides specifics of how two monoclonal antibodies, one to a linear epitope and the other to a conformational epitope in the same region of gp41 of HIV-1, have been used in the critical reagent positive control pathway to confirm immunoreactivity of immobilized peptide-BSA conjugate antigen used to detect human antibodies to HIV (U.S. Pat. No. 5,260,189, (Formoso, Olsen, and Buchanan). It also provides a specific example of the use of polyclonal serum antibodies as a positive control for the methods and devices used in this invention, for rapid lateral flow immunoassay of antibodies to human CRP.

Example 3 presents specifics and summary data on the evaluation of 12 combinations of reagents that did not prove useful for confirming the presence or absence of immunoglobulin in test samples. It also describes the discovery of a single binding reagent combination that was able to distinguish samples that contained human immunoglobulin from those that did not under the conditions used in the methods and devices of this invention.

Example 4 provides specific conditions used to identify a suitable fabric for the collection of gingival crevice oral fluid samples, to release fluid from the fabric and to identify HIV specific antibodies within the diluted gingival crevice fluid using the test strips and reagents of this invention.

Example 5 provides specific details of the use of the oral fluid rapid test device as described in the figures to detect antibodies to HIV in human oral gingival crevice fluid.

Example 6 provides specific details of the use of one whole blood rapid test device of this invention for detection of antibodies to HIV in fingerstick or venipuncture whole blood.

Example 7 and FIG. 14 provide illustrations of results obtained with use of the rapid test platform of this invention. Shown are a True Positive, a True Negative, and two Invalid tests. One invalid was falsely Negative due to inactive critical reagents, and the other Invalid test was falsely Negative due to insufficient immunoglobulins in the test sample.

Example 8 describes a study demonstrating that monoclonal antibody F240 is sufficiently potent that very small quantities are required to bind enough of the monoclonal to allow recognition by particulate marker protein G+L colloidal gold and produce a line of particulate binding to the immobilized HIV-1 antigen, leaving insufficient monoclonal antibodies to migrate past the immobilized antigen to be recognized by downstream immobilized recombinant protein A and cause a line of particulate marker at the downstream location. This allows all controls (both reagent reactivity and sample adequacy) to be placed on the same pathway and simplifies interpretation of the test results.

Example 9 and FIGS. 16C-16E provide specific details of a test design wicking system and large absorbent pad sink located at the downstream end of the test device that allow capture of all of the liquid added to the test device after it has passed through test and control strips, while simultaneously preventing backflow of test reagents from absorbent pad to test and control strips. Currently available lateral flow tests have limited reading windows during which test results may be reliably evaluated, due at least in part to backflow of reagents from the absorbent pad into the area where the test result is evaluated. Backflow prevention is accomplished in this invention by both the size of the absorbent pad which is capable of absorbing the total liquid added to the test device, and the location of evaporation vents in the test device that are oriented over the absorbent pad and the outflow wicks that move liquid from the downstream end of test and control strips into the absorbent pad. After all liquid added to the test device has flowed into the absorbent pad, evaporation first results in drying of the surface of the absorbent pad and the overlying wick that connects the downstream end of the test and control strips and absorbent pad. Any liquid remaining in the partially evaporated absorbent pad remains in the inferior aspect of the pad, unable to complete backflow into test and control strips due to evaporation while traversing the dried surface of the absorbent pad and downstream end of the dried wick. Using this design, no backflow of reagents from absorbent pad to test or control strips occurred during more than one week of observation.

Example 10 explains the details of methods and design innovations in (a) the size and orientation of particulate marker pad membranes of this invention, that when combined with (b) methods and designs that permit interaction of a range of sample concentrations with marker during the test, as illustrated in FIGS. 16B, C, E, and F.

Example 11 provides details of experiments that demonstrate that the innovations described in Example 10 together provide increased sensitivity for the detection of known quantities of monoclonal antibody specific to HIV-1 antigen as described in Examples 1 and 2 (Table 2, Example 11), and for detection of seroconversion from HIV negativity to positivity, as compared to conventional lateral flow immunoassays (Table 3, Example 11). These changes suggest an approximate 5 to 10 fold increase in sensitivity using the methods and design innovations of this invention.

Example 12 confirms the importance of importance of diluting the test sample sufficiently to not overwhelm the amount of particulate marker available to combine with immunoglobulin.

Dilutions of 1:200 or greater of human serum appear to be optimal for the amount of particulate marker available in rapid tests using the methods and designs of this invention (Table 4, Example 12). FIG. 11F illustrates how the methods and designs of this invention allow immunoglobulin interaction with particulate marker not only in the same concentrations as conventional lateral flow immunoassays, but also in amounts 10 to 100 fold lower. This 10 to 100 fold range of available concentrations of immunoglobulin that interact with a constant amount of particulate marker with the methods and designs of this invention, increase chances for optimal ratios that allow maximum sensitivity. When time periods were compared for delivery of particulate marker to the developing immunoassay with conventional particulate marker pads (68, FIG. 16F) as compared to the newly designed and oriented particulate marker pads of this invention (67, FIG. 16F), particulate marker was delivered to the developing assay over a three times longer period than with conventional lateral flow immunoassays (Table 5, Example 12).

Example 13 and FIGS. 17A, 17B, and FIG. 18 describe the use and design of an insert that fits precisely with correct orientation into the opening in the cover of the test devices of this invention, where the swab would otherwise be placed when testing oral samples, the may be used to evaluate whole blood. It contains a funnel like portion in its top that is designed to receive two free-falling drops of whole blood, that then migrate along the membrane of the insert to enrich the downstream component of the whole blood for acellular components. After 4 minutes, the dilution port of the test device (2, FIG. 1) is pushed down into the locked position to isolate an area of membrane saturated with acellular enriched whole blood which is then removed and diluted by diluent applied under pressure according to U.S. Pat. No. 7,364,914 B2) and diluted sample is delivered through the opening on the underside of the midpiece (FIG. 12) into the diluted sample membrane at area 57 (FIGS. 16B, C, E, and F) to flow to the pathways illustrated in FIG. 13 and FIGS. 16 C, E, and F where the results are read through the window of the cover as illustrated in FIGS. 15B-15E.

FIGS. 15B-15E illustrate INVALID, TRUE POSITIVE and TRUE NEGATIVE test results viewed through the test result windows of the revised cover of FIG. 15, with tests performed as in Examples 5-7 in which the sample adequacy recombinant protein A control is immobilized downstream on the same nitrocellulose strip as the reagent positive control pathway.

Use of a Method and Device for Collection and Testing of Oral Fluid Samples

The oral fluid collection device of this invention, as illustrated in FIGS. 1-16, is used as follows:

Using the swab provided (4, FIG. 4; and FIGS. 6A and 6B) the user rubs one side of the swab up and down along the entire upper and lower tooth-gum lines.

Figure 5:
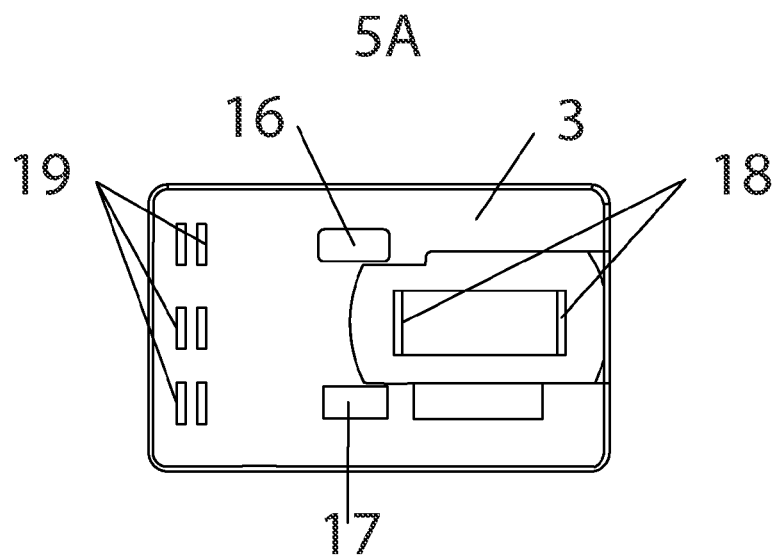
FIG. 5A is a top plan view of the cover (3) for the oral fluid rapid test device. It illustrates windows to view test (16) and control (17) results, evaporation ports (19) for test and control strips, and an opening to receive the sample dilution port, two edges of which contain projecting ridges (18) which mate with corresponding projecting ridges (35, FIG. 2B) of the sample dilution port when it is in the depressed and locked position (see FIGS. 9A and 9E).
FIGS. 5B and 5C are front and perspective views of the cover respectively, that illustrate the opening (20) for the oral fluid swab that contains the oral fluid to be sampled during performance of the oral fluid rapid test.
Figure 5:
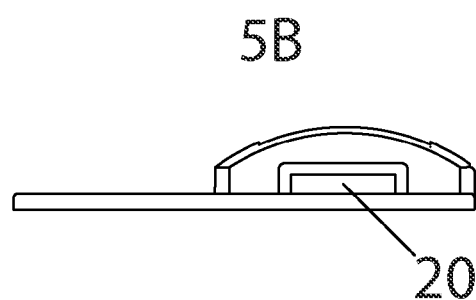
Figure 5:
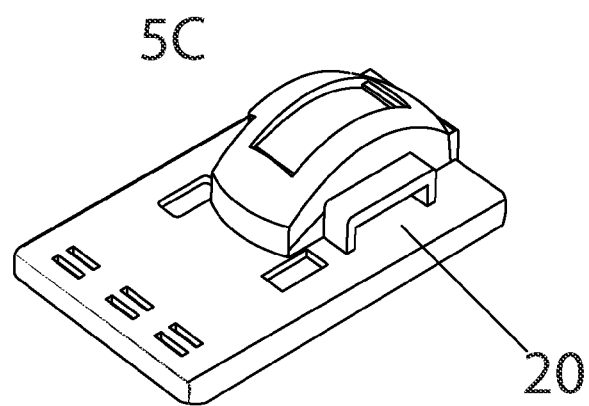

The swab is then inserted into opening 20 of the test device (FIG. 5). The dilution port 2 (FIGS. 1, 2 and 3) is then pushed down into the locked position (FIGS. 9E, 10C and 11) after first removing the yoke (1, FIG. 1) that prevents premature depressing and locking. This locking is accomplished by 4 separate contact points, two on each of two hook arms of the dilution port (32, FIG. 2B) that snap out into window 30 of the base receptacles 29 for the dilution port hook arms (FIGS. 8A-C) and abut against the upper edge 33 of each window (FIG. 8B, and 33S, FIG. 9E) thereby preventing the hook arms from being withdrawn from the device once depressed and locked. This locked position of the dilution port isolates a portion of the swab fabric which has been saturated with oral gingival crevice fluid, by a perimeter of compression around the isolated fabric caused by an o-ring (5, FIGS. 1, 7B and 7C, and 5S, FIG. 11) on the undersurface of the fabric and an opposing pressure from a mating inferior surface of the dilution port (37, FIGS. 2C and 37S, FIGS. 11 and 12). Also, once the dilution port is depressed in to the locked position, the cover of the test device cannot be removed because the swab (FIG. 6) locked in place by the dilution port (FIG. 2B) which is locked into the base prevents removal of the cover to access the dilution port in order to unlock it. This design prevents attempts to re-use the test device.

A vial or syringe provided with a known quantity of running buffer is inserted into opening 31 (FIG. 9A) of the dilution port to form a leak-proof friction fit, and the buffer is pushed out of the vial or syringe under pressure and down through central channel 36 of the dilution port (FIG. 10C) through the isolated saturated membrane thereby removing sample which travels through channel 25 of the midpiece (FIG. 7A) to exit through the channel 27 on the bottom surface of the midpiece (FIG. 7C) providing a diluted sample to the diluted sample membrane (8, FIGS. 12B-12D and FIG. 13). No more than 15 seconds are required for this entire process after insertion of the oral swab into the device and depression of the dilution port until completion of delivery of running buffer from the provided vial or syringe.

The diluted sample travels through the diluted sample membrane in flow direction 2 (FD2, FIG. 13), and from there in flow direction 3 (FD3, FIG. 13) through upstream and downstream portions of the two or more pathways of the test, to provide readable results in ordinary circumstances within 10 minutes.

The upstream portion of the reagent positive control and sample adequacy pathway contains dried mobilizable monoclonal or polyclonal antibodies to the antigen being used to detect specific antibodies, located on the bridging membrane between it and the particulate marker pad, and further upstream mobilizable particulate markers such as colloidal gold or magnetic spheres bound to protein L and protein G, that recognize both the mobilized monoclonal or polyclonal antibodies and human immunoglobulins. As the monoclonal or polyclonal antibodies are mobilized by sample diluted with running buffer and containing mobilized particulate markers, some migrate ahead of the particulate marker and bind to downstream immobilized antigen prior to interacting with particulate marker and others interact with particulate marker as they migrate toward immobilized antigen. A line is formed at the site of antigen immobilized on nitrocellulose or other suitable membrane located downstream (on membrane 10, FIG. 13). The formation of this line confirms particulate markers bound to protein L and protein G are reactive, that the monoclonal or polyclonal antibodies directed at the immobilized antigen are reactive and that the immobilized antigen in this positive reagent control flow pathway is also immunoreactive. This line may be observed through window 40 in the cover of the device (FIG. 15A) at location 45 of FIG. 15D. Absence of this particulate marker line at the immobilized antigen can result from failure of any of the three critical positive control pathway reagents. This result of no particulate marker binding to antigen means that the test must be interpreted as invalid by the user, thereby preventing potentially reporting a false negative result due to failure of any one or more of the three critical test reagents. Further down this same pathway immunoglobulins within the diluted sample that have complexed with particulate marker are recognized and bound by recombinant protein A (Repligen Corp., Waltham, Mass., USA, 44, FIG. 15D). Absence of a line at this location means that the sample being tested does not contain sufficient immunoglobulin to allow detection of antibodies to specific immobilized antigens if they are present in the diluted sample.

The upstream portion of the pathway for detection of specific antibodies contains the same dried mobilizable particulate markers complexed with protein G and protein L as found in the positive control reagent pathway. The downstream portion of this pathway contains identical antigen immobilized with identical positioning on nitrocellulose or other suitable membrane under conditions identical to those used for this antigen to coat on identical downstream membranes in the positive control reagent and sample adequacy pathway. Observation of no line of particulate marker binding to the immobilized antigen in this pathway through window 41 of the cover (FIG. 15A) at position 46 (FIG. 15E), but definite lines of identical particulate marker bound to antigen and recombinant protein A in the reagent positive control and sample adequacy pathway, allows the conclusion that the diluted test sample is truly negative for antibodies specific to the immobilized antigen. The presence of a line of particulate marker bound to immobilized antigen in the specific antibody pathway, along with a line over immobilized identical antigen and a line over immobilized recombinant protein A in the reagent positive control and sample adequacy pathway, allows the conclusion that the diluted oral fluid sample is truly positive for antibodies specific to the immobilized antigen.

Use of a Method and Device for Collection and Testing of Whole Blood Samples

The principles of the methods of this invention, as described above in the section on use of the oral fluid testing device, are identical for testing both whole blood and oral samples. The differences are found in the test device.

In the newly designed device for testing whole blood from fingersticks or venipuncture, instead of inserting a swab containing oral fluid into opening (20) in the cover an insert for receiving whole blood (FIGS. 17A, 17B, and 18) is placed into the opening. This insert contains a funnel-like component in its top section (FIG. 17A). The top portion of this funnel is wide and permits the user to easily place the finger stuck by the fingerstick lancet into the upper portion of the funnel so that two drops of free-falling whole blood be collected into the funnel to contact the blood receiving membrane at location 65 (FIG. 18) held between top and bottom portions of the insert (FIGS. 17A and 17B). The special blood receiving membrane (e.g. LF1, GE-Whatman, Florham Park, N.J., USA) separates serum or plasma portions of the whole blood in the leading front of wicking down the membrane from cellular components of whole blood that migrate more slowly. The whole blood flows by capillary action from location 65 (FIG. 18) toward the other end of the membrane to saturate location 66 (FIG. 18) of the membrane with acellular serum or plasma. This method of collecting the whole blood into the test device helps to eliminate test failures due to improper transfer of blood drops from the portion of the finger penetrated by the lancet to the medical device.

The migration of the whole blood sample along the membrane to separate cellular from acellular components takes 4 minutes before an area of membrane saturated with serum or plasma from the sample overlies the o-ring of the device, that in combination with the dilution port when depressed and locked in place, isolates an area of serum saturated membrane for testing. The o-ring in the midpiece for the whole blood collection device is of smaller dimensions (43, FIG. 16D) than the o-ring used for the oral fluid rapid test and combines with a dilution port to isolate an area of saturated membrane that approximates half the surface area of saturated membrane than is used in the oral fluid test. This partially adjusts for the approximately four to six-fold lower concentrations in gingival crevice fluid as compared to serum or plasma. The opening in the top of the dilution port that accommodates the vial or syringe containing running buffer is the same size in the dilution port used for testing whole blood as in the dilution port for oral fluid. The base of the whole blood test device is identical to the base of the oral fluid test device. The time to a readable test result for each test is 10 minutes. For the oral fluid test, this time is taken up completely by migration following addition of diluent buffer. For the whole blood test, four minutes is required for initial migration that separates acellular from acellular components, and the migration following addition of diluent running buffer requires an additional six minutes to achieve a readable result. Both tests do not lose their readability for several days to weeks following test completion.

The following examples are intended to illustrate but not limit the scope of this invention.

EXAMPLES

Example 1

Immunoreactivity of HIV Peptide-BSA Protein Conjugate Antigen

Peptide-BSA protein covalent conjugates containing peptides with the sequences found in the immunodominant portion of HIV-1, sequence region 597-610 of gp41, as described in U.S. Pat. No. 5,260,189, (Formoso, Olsen, and Buchanan) and by Dorn et al (J. Clin Microbiology 38:2, pp. 773-780, February 2000) were striped at approximately 1.5 ul/cm of a 250 ug/ml concentration of total protein in 0.1N PBS, pH 8.0 containing 0.05% sodium azide, onto nitrocellulose (Hi-Flow Plus HF-120, Millipore Corporation, Bedford, Mass., USA) at approximately 1.5 ul/cm, and dried for 10 minutes at 35 degrees C. under vacuum, followed by further drying and storage at room temperature in the presence of anhydrous calcium sulfate desiccant (Drierite Company, Xenia, Ohio, USA). These striped nitrocellulose strips were then laminated, with overlapping to permit capillary flow, to an absorbent pad (CF-4, GE-Whatman, Florham Park, N.J., USA) on the downstream end, and to a wicking glass membrane on the upstream end (Grade 142, Ahlstrom Filtration, LLC, Mount Holly Springs, Pa., USA) using a single-sided polyester-adhesive tape (ARcare 8160, Adhesives Research, Inc., Glen Rock, Pa., USA). Approximately 0.25 OD units of particulate conjugate of Protein A bound to 40 nm colloidal gold (BA.PAG40, British Biocell International, Cardiff, UK) were mixed with 1 ml of normal human serum diluted 1:100 with running buffer consisting of 50 mM PO4 (Spectrum Chemical Manufacturing Corp., Gardena, Calif., USA), pH 7.4 with 0.1N NaCl (Spectrum), 0.05% Na azide (Spectrum), 0.1% Bovine Serum Albumin (IgG-free, protease-free, Jackson Immunoresearch Labs, West Grove, Pa., USA) and 2% Tween 20 (SigmaUltra, Sigma-Aldrich, Inc., St. Louis, Mo., USA). As described by Rosenstein et al. in U.S. Pat. No. 4,855,240, in addition to the BSA, a sugar such as sucrose or trehalose was added to provide concentrations of 2% to 15% to minimize agglutinations of the particulate conjugate in the presence of the diluted serum and to decrease undesired interactions between particulate conjugate and the laminated membranes of the flow path.

Diluted human serum containing antibodies to HIV produced a visible reddish-purple line against a white background at the site of the HIV peptide-BSA protein antigen immobilized on the nitrocellulose portion of the laminated test strips and no such line developed with similar diluted human serum that did not contain antibodies to HIV.

Immunoreactivity of the HIV peptide-BSA conjugate antigen was further evaluated using monoclonal antibodies. Monoclonal antibodies proven to recognize the immunodominant antigenic domain of HIV, specifically the amino-acid sequence regions 597-617 or 592-606 of gp41 of HIV-1, monoclonal antibodies T32 and F240 respectively, were each obtained through the NIH AIDS Research and Reference Reagent Program, Division of AIDS, NIAID, NIH: T32 Monoclonal Antibody (Cat. No. 11391) from Dr. Patricia Earl, NIAID; HIV-1 gp41 Monoclonal Antibody (F240) from Dr. Marshall Posner and Dr. Lisa Cavacini. The published references for each of these monoclonal antibodies are T32—Earl et al., J. Virol. 71 (1997): 2674-2684, and Cavacini et al., AIDS Res Hum Retroviruses 14:1271-1280, 1998. The overlapping region of these two monoclonal antibodies is sequence region 597-606. This region contains a sequence CSGKLIC that is relatively preserved among widely variant geographic isolates of HIV, and this sequence is contained within the peptides described in U.S. Pat. No. 5,260,189, (Formoso, Olsen, and Buchanan). Monoclonal antibody T32 recognizes a linear epitope within this region (see Earl et al., J. Virol. 71 (1997): 2674-2684) and monoclonal antibody F240 recognizes a conformational epitope (see Cavacini et al., AIDS Res Hum Retroviruses 14:1271-1280, 1998), presumably formed by an S—S bond between the two cysteines in the peptide sequence CSGKLIC.

HIV-1 peptides containing the sequence CSGKLIC were conjugated to BSA as described in U.S. Pat. No. 5,260,189 and this peptide-BSA conjugate was custom bound to 40 nm colloidal gold by British Biocell International (BBI, Cardiff, UK). Monoclonal antibodies F240 and T32 were immobilized on nitrocellulose HF 120 (Millipore Corp., Bedford, Mass., USA) by striping at various concentrations monoclonal antibody in 0.1N PBS, pH 7.4 with 0.05% Na azide, followed by drying at 35 degrees C. under vacuum for 15 min followed by room temperature desiccation in the presence of anhydrous calcium sulfate desiccant (Drierite Company, Xenia, Ohio, USA). The custom bound HIV peptide-BSA conjugates were diluted to 2.5 OD concentration in 2 mM borate pH 7.1 with 0.0025% Na azide and 15% trehalose and coated onto S-14 conjugate pads (GE-Whatman, Florham Park, N.J., USA) that had been pre-blocked with 0.0025% Na azide (Spectrum Chemical, Gardena, Calif.), 0.1% bovine serum albumin (Probumin, Diagnostic Grade, Celliance, Serologicals Corporation, Kankakee, Ill., USA) and the coated S-14 conjugate pads were dried at 37 degrees C. under vacuum for 30 min followed by room temperature drying in the presence of anhydrous calcium sulfate desiccant (Drierite Company, Xenia, Ohio, USA). Evaluation strips were laminated using ARcare 8160 (Adhesives Research, Inc., Glen Rock, Pa., USA) with monoclonal antibody-bound nitrocellulose connecting to an absorbent pad downstream, and upstream to the conjugate pads containing BBI-prepared 40 nm colloidal gold HIV peptide-BSA conjugate antigen, which overlapped further upstream to a wick upstream (Grade 142, Ahlstrom Filtration, LLC, Mount Holly Springs, Pa., USA). These test strips were evaluated by applying running buffer PBSAAT consisting of 50 mM PO4 (Spectrum Chemical Manufacturing Corp., Gardena, Calif., USA), pH 7.4 with 0.1N NaCl (Spectrum), 0.05% Na azide (Spectrum), 0.1% bovine serum albumin (IgG-free, protease-free, Jackson Immunoresearch Labs, West Grove, Pa., USA) and 2% Tween 20 (SigmaUltra, Sigma-Aldrich, Inc., St. Louis, Mo., USA).

Monoclonal antibodies T32 and F240 were immobilized on nitrocellulose (HF 120) at various concentrations in 0.1 N PBS, pH 7.4 with 0.05% Na azide and dried as described above. Monoclonal antibody T32 produced a faint line of binding of the HIV peptide-BSA conjugate antigen bound to 40 nM colloidal gold when striped at 400 ug/ml concentration. A comparable line of binding of the same HIV Peptide-BSA conjugate antigen was achieved with F240 monoclonal antibody striped at 100 ug/ml. The disadvantages of this type of a positive control for a rapid test are (a) the HIV peptide-BSA antigen is not identical to the same antigen used in the flow path to detect antibodies specific to HIV, since it has been modified through the procedures of binding it to colloidal gold and (b) this type of positive control does not simultaneously evaluate the reactivity of the particulate markers used in the flow path to detect antibodies specific to HIV. These disadvantages may be overcome by instead coating the same native HIV peptide-BSA conjugate antigen to nitrocellulose in both flow paths, providing the monoclonal antibodies can be recognized by the particulate marker.

Monoclonal antibody T32, which recognizes a linear epitope, produced a lightly visible line at the site of immobilized HIV peptide-BSA protein antigen on the nitrocellulose laminated strips when 15 micrograms of antibody was reacted with 0.20 O.D. units of 40 nm colloidal gold protein G (BioAssay Works, LLC, Ijamsville, Md., USA) and migrated with running buffer PBSAAT (described above) downstream over the test strip. In contrast, the F240 monoclonal antibody produced a significantly stronger visible line of binding to the immobilized HIV peptide-BSA protein antigen when only 10 picograms was reacted with the same colloidal gold protein G and migrated over identically striped laminated nitrocellulose strips. This 1500-fold or greater potency of the F240 monoclonal antibody suggests that the HIV peptide-BSA protein antigen is in cyclized form, and the reactivity of this antigen with human antibodies is consistent with previous reports that the dominant epitope for the human immune response to HIV infection is a conformational epitope, presumably the S-S loop epitope contained within the HIV peptide-BSA protein antigen used in this example.

Example 2

Evaluation of Stability of HIV Peptide-BSA Conjugate Antigen and Monoclonal or Polyclonal Antibody in Dried State for Use in Rapid Diagnostic Tests to Prove Antigen Integrity in the Reagent Positive Control Flow Path Nitrocellulose striped with HIV peptide-BSA conjugate antigen as in Example 1 was stored at room temperature at 10-30% humidity levels and tested over time against both F240 monoclonal antibody and human serum containing antibodies to HIV. The antigen retained its reactivity for more than one year under these conditions.

2 ug of F240 monoclonal antibody was spotted onto a 0.7 cm×1 cm membrane strip of protein G 40 nm colloidal gold coated at 0.25 OD units/square cm (BioAssay Works, LLC, Ijamsville, Md.), allowed to dry at room temperature and then stored at room temperature for 13 days without desiccant. The contents of this membrane strip were then migrated over the HIV peptide-BSA conjugate dried onto nitrocellulose, using running buffer as described in Example 1. The F240 monoclonal antibody and protein G colloidal gold produced a strong line of immunoreactivity with the HIV peptide-BSA conjugate antigen, confirming a degree of stability of the F240 monoclonal antibody when dried in the presence of the stabilizers present in the coated colloidal gold membrane strip.

F240 monoclonal antibody was then diluted to a concentration of 7.5 ug/ml in a solution of 0.1N PBSAA (0.1 N PO4, pH 7.4 with 0.1 N NaCl, 0.01% BSA (Jackson Immunoresearch Labs, protease and IgG free), 0.03% Na azide and 10% Trehalose (FlukaBiochemika, Sigma-Aldrich Corp., St. Louis, Mo., USA) and coated to three different membranes S14 (GE-Whatman, Florham Park, N.J., USA), 8964 (Ahlstrom, LLC, Mount Holly Springs, Pa., USA) and G041 (Millipore Corporation, Bedford, Mass., USA) and dried at 45 degrees C. with vacuum for 10 minutes, followed by room temperature drying and subsequent storage in the presence of anhydrous calcium sulfate desiccant (Drierite Company, Xenia, Ohio, USA). These stabilized & dried F240 monoclonal was stable and showed no evidence of decreased potency at recognizing the peptide-BSA HIV antigen coated to nitrocellulose when repeatedly tested during two month period, and again one year later.

Polyclonal antibody was also evaluated for use in the positive control pathway. Human CRP, goat anti-human CRP and rabbit anti-human CRP were obtained from CalBioreagents Inc. (San Mateo, Calif., USA). The human CRP was coated to nitrocellulose at 100 ug/ml in 20 mM Tris buffered saline pH 8.2 containing 0.005% BSA and 20 mM sodium azide. Test strips were assembled to allow running buffer alone, normal human serum diluted 1:100 in running buffer, or running buffer containing 55 ug/ml of goat anti-human CRP or 30 ug/ml rabbit anti-human CRP to run past mobilizable protein G 40 nm gold (BioAssay Works) and then past the immobilized human CRP. Strong lines of binding were observed between the particulate marker and the solutions containing goat or rabbit anti-human CRP, but no binding occurred with normal diluted normal human serum or running buffer alone. This demonstrated that polyclonal antibodies can also be used to recognize known antigens downstream in rapid flow test positive controls. Conditions similar to those used for the F240 MAb would be expected to permit these polyclonal antibodies to be dried in stabilized mobilizable condition with adequate shelf life for incorporation in to rapid lateral flow tests for use as a positive control.

Example 3

Development of a Method to Determine Whether an Adequate Amount of Immunoglobulin is Present in the Diluted Sample to Allow Detection of Specific Antibodies to an Antigen or Analyte of Interest, if Present No currently available rapid tests for antibodies to specific antigens or other ligands contain controls to determine if an adequate amount of immunoglobulin is being evaluated to allow detection of specific antibody if present. This is an important omission because tests of fingerstick or venipuncture whole blood may be falsely negative if insufficient blood is introduced into the test, and samples of oral gingival crevice fluid may lack sufficient immunoglobulin to allow accurate detection of specific anti-HIV antibodies if the oral swab fluid sample is collected improperly.

Experiments were conducted using different immunoglobulin detection reagents, one or more being bound to a particulate marker, and another immobilized at the downstream end of the test window of the flow path for detection of specific antibodies, to determine whether a set of immunoglobulin binding agents could be identified that in correct concentrations would demonstrate binding of particulate markers by the most downstream immobilized immunoglobulin detection reagent only if immunoglobulin concentrations in the diluted sample are sufficient to allow detection of antibodies to specific antigens, if present. The combinations evaluated are presented in Table 1.

Surprisingly, of the 13 combinations tested, only the combination of both Protein L and Protein G colloidal gold when reacted with samples containing or not containing immunoglobulin, was able to correctly discriminate the presence of immunoglobulin. This combination, when reacted with monoclonal antibody F240 or with human sera diluted with running buffer, produced binding to rPAdownsteam, but did not bind to the immobilized rPA downstream when simply diluted with running buffer in the absence of immunoglobulin (Table 1). The conditions for coating the recombinant protein A to nitrocellulose were 0.1N PBS, pH 7.4 containing 0.01% BSA (Jackson ImmunoresearchIgG and protease free) and 0.05% Na azide. Optimal concentrations for rPA coating under the conditions of these assays were 1 to 5 micrograms/ml. Under these conditions, the rapid assay could correctly discriminate whether the test sample contained sufficient quantities of immunoglobulin to be likely to demonstrate a line of binding of particulate marker to immobilized antigen, if specific antibodies to that antigen are present, and to detect those samples that were inadequate in terms of containing sufficient immunoglobulin. This combination was used in subsequent experiments in the devices described herein to determine adequacy of the test samples.

TABLE 1

Combinations of Ig Binding Reagents to Evaluate Sample Ig Adequacy

| Ig Binding Reagent Immobilized on Nitrocellulose | Ig Binding Reagents Bound to Particulate Markers | Ig Present (+) or Absent (−) | Binding of Particulate Marker to Immobilized IgG Binding Reagent |
|---|---|---|---|
| Protein A - Sigma-Aldrich | Protein A 40 nm Gold - BBI | + | + |
| Protein A - Sigma-Aldrich | Protein A 40 nm Gold - BBI | − | + |
| rProtein A - Repligen | Protein A 40 nm Gold - BBI | + | + |
| rProtein A - Repligen | Protein A 40 nm Gold - BBI | − | + |

TABLE 1-continued Combinations of Ig Binding Reagents to Evaluate Sample Ig Adequacy

| Ig Binding Reagent Immobilized on Nitrocellulose | Ig Binding Reagents Bound to Particulate Markers | Ig Present (+) or Absent (−) | Binding of Particulate Marker to Immobilized IgG Binding Reagent |
|---|---|---|---|
| Goat anti-human IgG - Equitech | Protein A 40 nm Gold - BBI | + | + |
| Goat anti-human IgG - Equitech | Protein A 40 nm Gold - BBI | − | + |
| Goat anti-human IgG Fc - Equitech | Protein A 40 nm Gold - BBI | + | + |
| Goat anti-human IgG Fc - Equitech | Protein A 40 nm Gold - BBI | − | + |
| Goat anti-human F(ab')2 - Jackson | Protein A 40 nm Gold - BAW | + | + |
| Goat anti-human F(ab')2 - Jackson | Protein A 40 nm Gold - BAW | − | + |
| Goat anti-human F(ab')2 - Jackson | Protein G 40 nm Gold - BAW | + | + |
| Goat anti-human F(ab')2 - Jackson | Protein G 40 nm Gold - BAW | − | + |
| Chicken IgY anti-human IgG - Aves | Protein A 40 nm Gold - BAW | + | + |
| Chicken IgY anti-human IgG - Aves | Protein A 40 nm Gold - BAW | − | + |
| Chicken IgY anti-human IgG - Aves | Protein G 40 nm Gold - BAW | + | + |
| Chicken IgY anti-human IgG - Aves | Protein G 40 nm Gold - BAW | − | + |
| Chicken anti-human IgG - *Gallus* | Protein A 40 nm Gold - BAW | + | + |
| Chicken anti-human IgG - *Gallus* | Protein A 40 nm Gold - BAW | − | + |
| Chicken anti-human IgG - *Gallus* | Protein G 40 nm Gold - BAW | + | + |
| Chicken anti-human IgG - *Gallus* | Protein G 40 nm Gold - BAW | − | + |
| rProtein A - Repligen | Protein G 40 nm Gold - BAW | + | + |
| rProtein A - Repligen | Protein G 40 nm Gold - BAW | − | + |
| rProtein A - Repligen | Protein L 40 nm Gold - BAW | + | + |
| rProtein A - Repligen | Protein L 40 nm Gold - BAW | − | + |
| rProtein A - Repligen | Protein G + L 40 nm Gold - BAW | + | + |
| rProtein A - Repligen | Protein G + Protein L 40 nm Gold | − | − |

Evaluation of Potential Combinations of Immunoglobulin Binding Reagents that might, in the correct concentrations, and only after the particulate marker bound Immunoglobulin Binding Reagent has reacted with Immunoglobulin and migrated downstream to the reagent immobilized on nitrocellulose, demonstrate binding of the particulate marker bound reagent to the reagent immobilized on nitrocellulose. Reagent Sources are Sigma Aldrich Inc. (St. Louis, MO, USA), Repligen Corporation (Waltham, MA, USA), Equitech-Bio Inc.(Kerrville, TX, USA), Jackson ImmunoResearch Laboratories, Inc., (West Grove, PA, USA), Aves Labs, Inc. (Tigard, OR, USA), Gallus Immunotech, Inc. (Fergus, Ontario, Canada), Example 4

Detection of Immunoglobulin in Human Gingival Crevice Oral Fluid Followed by Detection of Antibodies to HIV Peptide-BSA Antigen in Human Gingival Crevice Oral Fluid from HIV Positive Volunteers Human gingival crevice fluid was collected from an HIV negative volunteer onto an LF1 membrane (GE-Whatman, Florham Park, N.J., USA) by rubbing the membrane along the top and bottom tooth-gum lines for 30 seconds. This membrane was then placed onto midpiece (6, FIG. 1) containing size 010 o-ring (5, FIG. 1). This midpiece with membrane saturated with gingival crevice fluid was placed atop a test tube with the bottom exit of the midpiece allowing passage of fluid into the test tube. A dilution port (2, FIG. 1) was then placed atop the membrane so that when downward pressure was applied the compressive force between the bottom surface of the dilution port (37, FIGS. 2B and 2C) and mating top surfaces of the size 010 o-ring positioned beneath provided a perimeter of compression that isolated a region of membrane centripetal to the ring of compression that was saturated with gingival crevice fluid. Running buffer was then applied to opening 31 in the top of dilution port (FIG. 9A) and through the central channel of dilution port (36, FIG. 3A) to pass through the isolated region of LF1 membrane to provide a sample of gingival crevice fluid diluted approximately 1:69 within the test tube. This fluid was then applied to a test strip laminated together to provide upstream to downstream orientation of diluted sample membrane (Ahlstrom 142, Ahlstrom LLC, Mount Holly Springs, Pa., USA)—protein G 40 nm colloidal gold @ 0.25 OD units/cm² on polyester membrane (BioAssay Works, Ijamsville, Md., USA)—nitrocellulose (HF120, Millipore Corporation, Bedford, Mass., USA) coated upstream with peptide-BSA HIV antigen (Example 1 above) followed further downstream by rPA (Repligen)—absorptive pad CF5 (GE-Whatman, Florham Park, N.J., USA). The diluted gingival crevice fluid flowed down the strip and showed no binding to the HIV antigen, but showed definite but weak binding to the rPA, indicating detection of the presence of IgG in the sample. Since IgA is a prominent immunoglobulin in human oral fluids, and since protein L can bind IgA as well as IgG, the combination of both protein L and protein G 40 nm colloidal gold (both from BioAssay Works, LLC) were laminated to the upstream portions of otherwise identical strips and tested with the diluted oral gingival crevice fluid. Again, no binding of the particulate markers occurred to the HIV peptide-BSA antigen. However, further downstream the particulate marker complex produced a significantly stronger line of binding to rPA than with protein G colloidal gold alone. This protein G-Protein L-40 nm colloidal gold complex had also been found to produce the strongest recognition lines for bound Ig by Repligen recombinant Protein A, and the least non-specific binding between this rPA as compared to protein G-gold or protein L gold alone (see Table 1 above), so this combination was used thereafter for tests of immunoglobulin in oral fluid samples.

Figure 1:
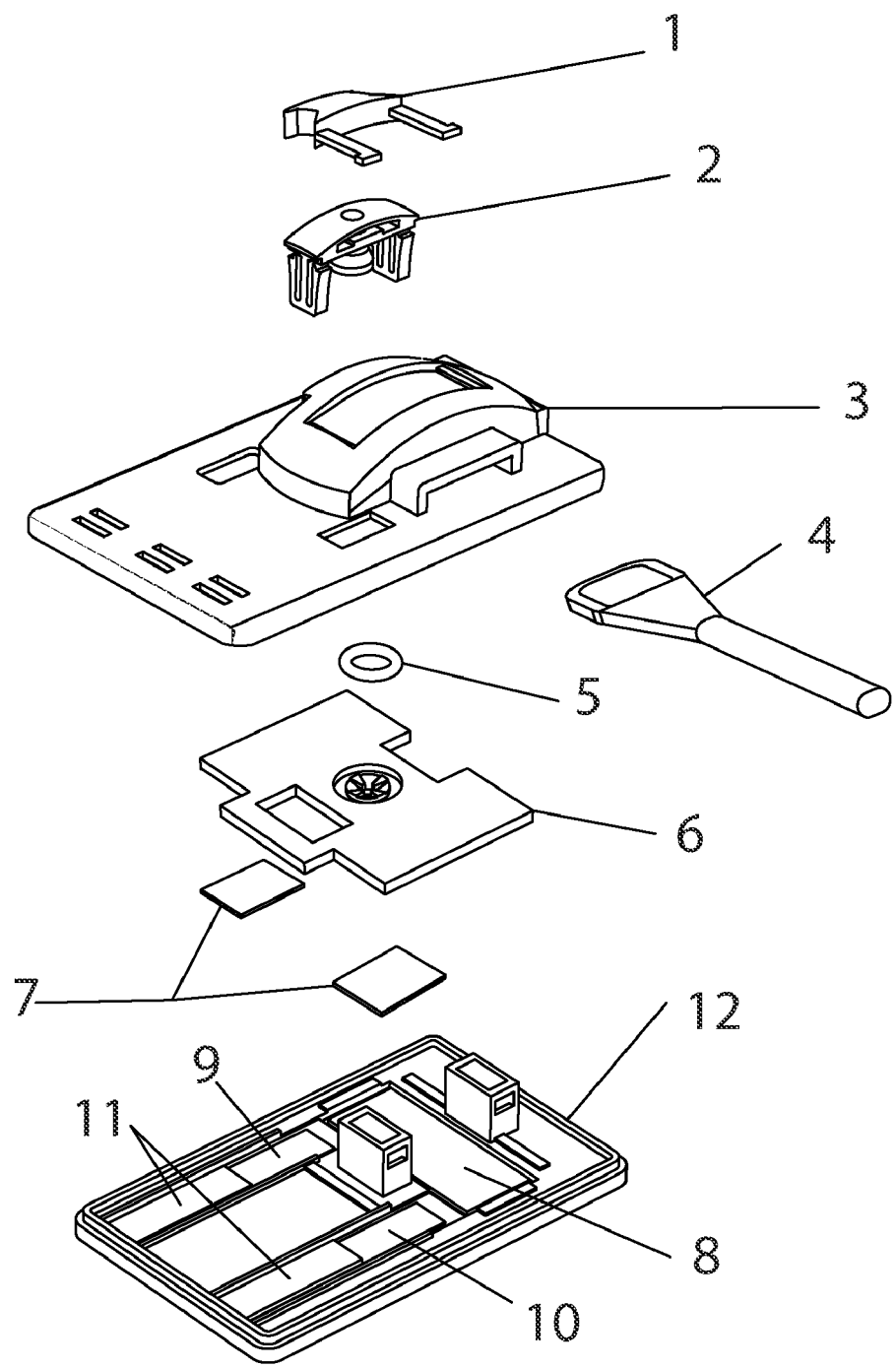
FIG. 1 is an exploded perspective view of a representative device of the invention including a yoke (1), a sample dilution port (2), a cover (3), a swab with suitable absorptive fabric and of correct dimensions for collecting oral fluid and fitting into the device (4), an o-ring (5), a mid-piece (6), a diluted sample membrane (7), two or more membranes containing particulate marker conjugate and in the case of the control lane a reagent that binds to the conjugate and recognizes the downstream antigen or antibody (8), one or more test membranes (9), a control membrane (10), absorbent pad membranes (11) and a base (12).
Figure 4:
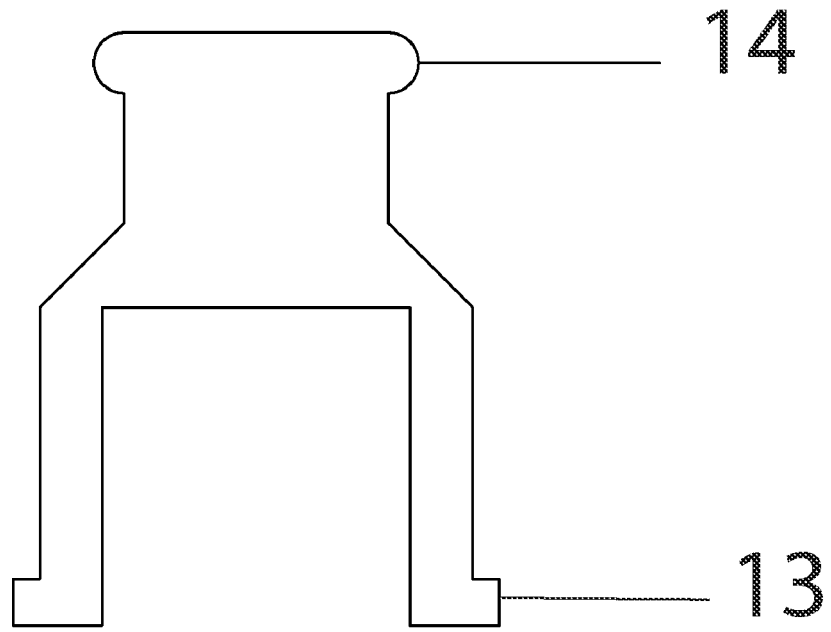
FIG. 4A is a top plan view and FIG. 4B is a front elevation view of yoke (1). Yoke has arm surfaces (13) that hold it within the dilution port and finger tabs (14) which allow it to be withdrawn from the dilution port when the arm surfaces (13) are compressed toward each other.
Figure 4:
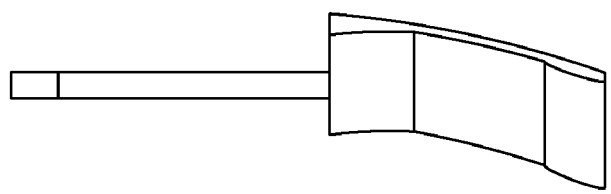

LF1 membranes (GE-Whatman) are fragile, and while useful for separating cellular components from serum or plasma when testing whole blood samples from patients, they would likely fragment if used for collecting oral fluid samples. For this reason, a fabric was sought that is clean, takes up fluid very rapidly within its void spaces, is capable of being ultrasonically welded to hold the fabric around swabs of designs such as that shown in FIG. 6A, and is capable of releasing the fluid with protein components present when tested in the test device (FIG. 1). Vectra AlphaSorb 10, double-knit fabric, used as swabs in clean room environments (ITW Texwipe, Mahwah, N.J., USA) was evaluated for this purpose. The AlphaSorb material was cut into strips that could be taped over a gloved finger, and the gloved finger with fabric strips attached was used to rub the tooth-gum line both top and bottom. The strips were removed from the taped finger, placed between dilution port and o-ring in midpiece over a test tube as described above, and diluted with a known volume of running buffer (see Example 1 above) and the diluted gingival crevice fluid was run over strips laminated with overlaps to allow capillary flow as described above from upstream to downstream as follows: diluted sample membrane—to protein L 40 nm colloidal gold—to protein G 40 nm colloidal gold—to HF 120 nitrocellulose containing immobilized HIV peptide-protein antigen followed downstream by rPA (Repligen)—to absorptive pads of CF5 glass-cellulose (GE-Whatman). The performance of diluted gingival crevice fluid samples collected on the AlphaSorb fabric were compared to oral fluid swabs sold commercially by CalypteBiomedical Corporation (Portland, Oreg., USA). The recognition of Ig in the diluted samples by rPA was strong and equivalent for samples collected from AlphaSorb fabric and the commercial Calypte swabs. Another diluted fluid sample, using the transport buffer provided by Calypte instead of the running buffer described in Example 1, also gave a line of recognition of Ig by rPA that was equal or slightly less strong than running buffer, but the diluted sample migrated more slowly through the membranes and provided a slightly yellow background as compared to the white background resulting from use of running buffer.

It was also observed that if the AlphaSorb fabric was left to remain either at refrigeration temperature or at room temperature for 5 hours before diluting the samples contained therein with running buffer, most of the immunoglobulin within the samples had adhered to the fabric and was not recoverable for testing. In contrast, if the directions from Calypte were followed, and the Calypte Messenger Transfer swabs were immediately immersed and rotated to remove sample into the vial of transport fluid provided, the sample diluted with transport fluid contained sufficient immunoglobulins to detect antibodies to HIV within the transport fluid diluted sample.

To test the ability of the AlphaSorb fabric to absorb and release antibodies reactive with the peptide-BSA HIV antigen, human volunteers that were known to be HIV positive from laboratory tests were recruited. Three volunteers were tested using the method of AlphaSorb fabric strips taped over a gloved finger to collect the gingival crevice oral fluid. After informed consent was obtained the positive volunteers were compared to a known HIV negative volunteer during each test running. The diluted samples from each volunteer, obtained by using running buffer to obtain and dilute an isolated area of fabric using the compressed perimeter method described above, were tested over strips consisting from upstream to downstream of diluted sample membrane-particulate marker pad containing Protein L and Protein G 40 nm colloidal gold—nitrocellulose coated upstream with peptide-BSA HIV antigen, and downstream with recombinant protein A—absorption pad. Volunteer 1 had a viral load of 5950 and a CD4 count of 481. Volunteer 2 had a viral load of 693 and a CD4 count of 508. Volunteer 3 had a viral load of 1150 and a CD4 count of 557. All gingival crevice oral fluid samples from HIV positive and HIV negative volunteers showed strong lines of Ig recognition by rPA, indicating adequate immunoglobulin in the samples tested. Each of the three HIV positive volunteers produced an easily recognizable line of binding of particulate marker to the peptide-BSA antigen in the test strips, whereas no line of particulate marker binding was observed any of the three times the HIV negative volunteer provided an oral gingival crevice fluid.

Example 5

Figure 6:
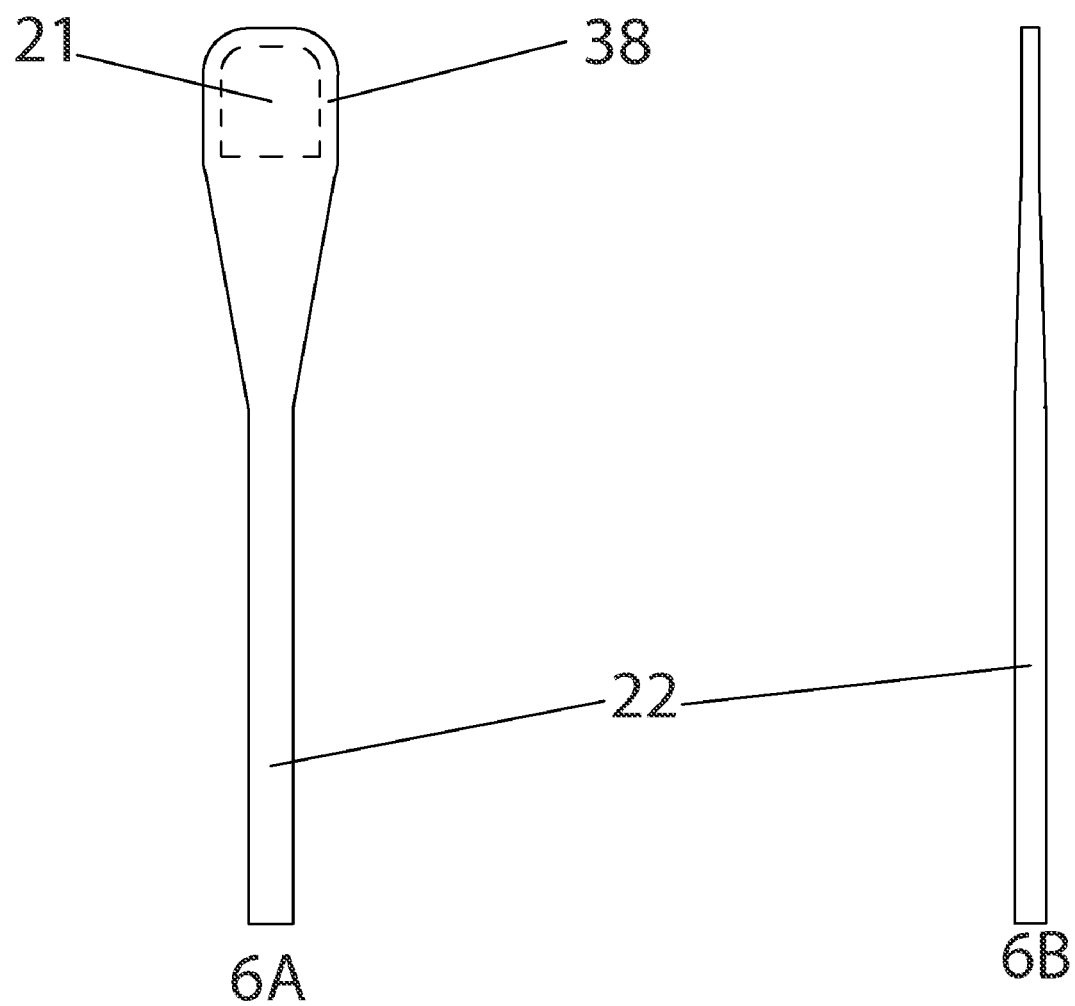
FIG. 6A is a top plan view of the oral fluid swab, with dotted lines to show the area of fabric on the swab to be sampled (21) by the sample dilution port (FIGS. 10B and 10C) when the swab containing collected oral fluid is placed into the device opening for same (FIGS. 5B, 5C, and 20).
FIG. 6B is a right side view of oral fluid swab that illustrates tapering of the swab in the region containing the fabric that collects oral fluid. This tapering provides the correct dimensions to allow compression and isolation of a portion of the fabric on the end of the swab by the dilution port to allow production of a diluted sample of oral fluid to the device during testing.
Figure 7:
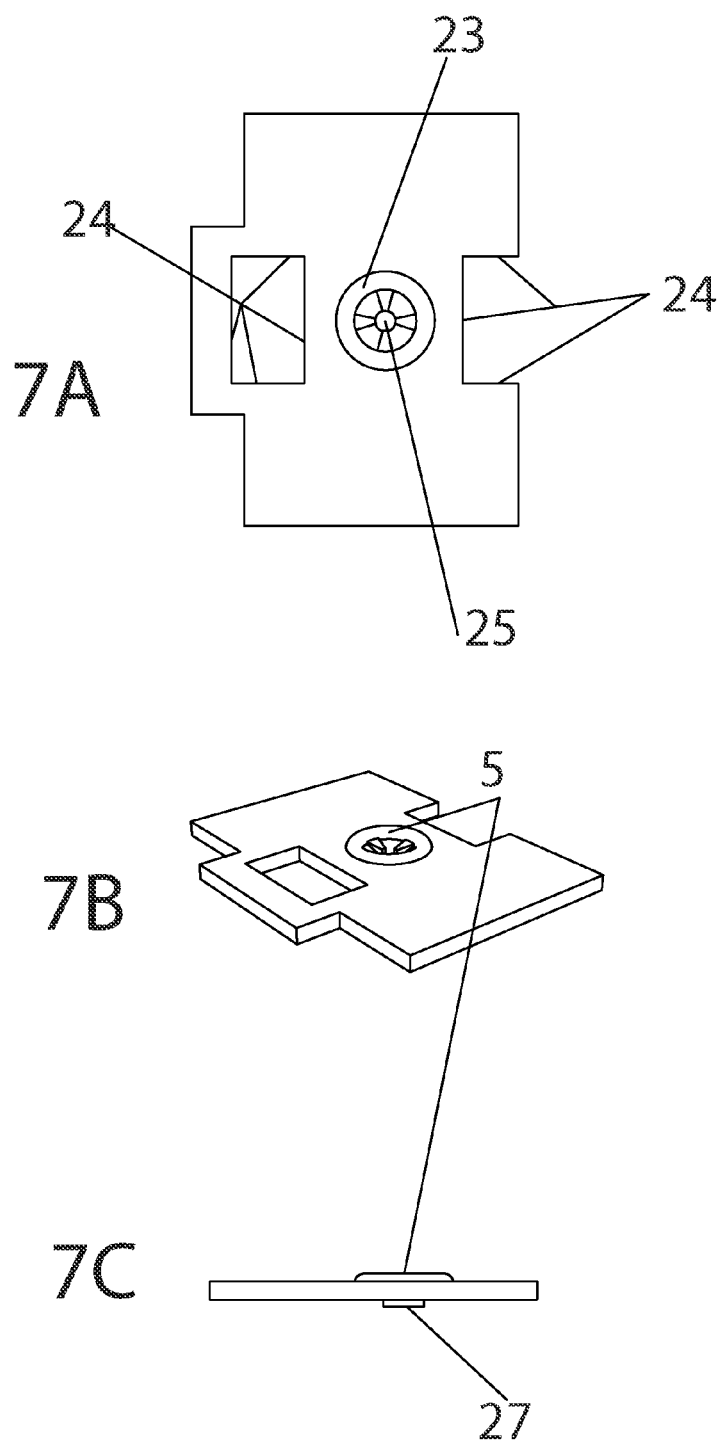
FIGS. 7A, 7B, and 7C are top plan, perspective, and front views of the oral fluid midpiece respectively.

Use of Rapid Test Device to Detect Human Antibodies to HIV Peptide-BSA Conjugate Antigen in Human Gingival Crevice Oral Fluid The membranes pre-coated with test reagents as described above were assembled into the oral fluid rapid test device as illustrated in the figures. The swab illustrated in FIG. 6 that contained AlphaSorb fabric sewed into place around a plastic swab frame designed as shown in FIG. 6 was used by an HIV positive volunteer to obtain an oral fluid sample for testing. The portion of the swab containing the AlphaSorb fabric was used to collect gingival oral fluid by swabbing for 20 seconds each both the upper and lower tooth-gum lines. The swab containing the gingival crevice oral fluid was then placed immediately into the test device through opening 20 (FIGS. 5B and 5C). The yoke (1, FIG. 1) was removed and the dilution port (2, FIG. 1) was depressed into the down and locked position (FIGS. 9D, 9E, 10C, and 11). This isolated an area of fabric saturated with oral gingival crevice fluid to sample for the presence of antibodies to HIV. An 800 microliter volume of running buffer was pushed through central channel 36 (FIGS. 3A and 10C) of the dilution port from a syringe fitted into opening 31 in its top surface (FIG. 9A). This fluid passed through the isolated membrane and out the undersurface of the midpiece onto the diluted sample membrane from which it passed over two separate pathways, the positive reagent control pathway and the pathway to detect antibodies specific for HIV-1 peptide-BSA antigen and further downstream to confirm that the sample contained adequate immunoglobulin. The test device performed smoothly and the test result was readable in less than 10 minutes from the time of adding the running buffer diluent. In the pathway to detect specific antibodies and confirm sample adequacy a positive line appeared over both the immobilized HIV antigen and the rPA. In the positive control reagent pathway a strong line developed over the immobilized HIV antigen. Both the HIV antigen itself and the conditions of coating the antigen to nitrocellulose were identical in both pathways. The control results confirmed that the collected sample was adequate, and that the critical reagents were working at the time of performing the test. These critical reagents included the antigen, the particulate marker reagent, and the dried mobilizable monoclonal antibody used to recognize and bind to antigen in the positive control pathway, regardless of whether or not antibodies to HIV antigen were present in the test sample. With these necessary controls all indicating a working test, it was possible to interpret the line of reaction to the HIV antigen in the specific antibody detection pathway as a TRUE POSITIVE.

Example 6

Use of Rapid Test Device to Detect Human Antibodies to HIV Peptide-BSA Conjugate Antigen in Human Fingerstick or Venipuncture Whole Blood A version of the device for testing whole blood was used to test an HIV positive volunteer that had been under treatment for more than 20 years. He was relatively healthy and had a CD4 count of 600 and an HIV viral load of less than 2500. After lancing the volunteer's finger with a pressure-activated lancet (Becton Dickinson, Franklin Lakes, N.J., USA), three drops of blood were transferred by bulb transfer pipet from the volunteers fingertip to a sample well in the device. Beneath the sample well was one end of a strip of LF1 membrane (GE-Whatman) of dimensions 11 mm wide×39 mm long. Capillary flow of the whole blood over the membrane took approximately 5 minutes, with the acellular components preceding the trailing cellular components, to provide after 5 minutes at the downstream end of the LF1 membrane an area of membrane approximately 12 mm×11 mm that overlay an o-ring size 008 sitting on top of the device midpiece. The yoke was removed, the dilution port depressed and running buffer fluid was introduced into the dilution port opening under pressure which produced a diluted serum sample to the diluted sample membrane below the midpiece as described in Example 5. The diluted sample then flowed over the two paths described in Example 5 as described above. After 5 additional minutes, the test was readable. There were strong easily discernable lines against a white background in both control areas, indicating intact antigen and an adequate sample. In addition, there was an easily readable positive result line on the immobilized HIV antigen in the specific antibody pathway, allowing an interpretation of the results as a TRUE POSITIVE.

Example 7

Use of the Test Devices with Inadequate Samples, with Membranes Striped with Antigen that has Lost Immunoreactivity or with Membranes that Contain Particulate Marker Reagents that are Inactive, as Compared to Other Tests that are Fully Functional In this example, the device test platform is used as described in Examples 2, 3, and 7. The reading window with rounded edges overlies a nitrocellulose test and control strip that contains immobilized antigen upstream that is used to detect specific antibodies in the test, and contains immobilized recombinant protein A downstream as a control to detect the presence of sufficient immunoglobulin in the diluted sample. The rectangular reading window overlies a nitrocellulose control strip of the reagent positive control pathway onto which the same antigen as used in the test strip has been immobilized under the same conditions and in the same location as in the nitrocellulose strip beneath the reading window with rounded edges. Upstream along the reagent positive control pathway Monoclonal Antibody F240 has been added to the bridging membrane (7, FIGS. 1 and 12) containing particulate marker of protein G bound to colloidal gold as described in Example 2. No monoclonal antibody has been added to the particulate marker pad upstream in the specific antibody detection pathway.

FIG. 14A—INVALID test due to failure of critical test reagents. This figure illustrates the results obtained, as viewed through the device cover, after tests are run in which the immobilized antigen has deteriorated, the particulate marker reagent has become inactive, or monoclonal antibody dried onto membranes upstream in the reagent control pathway has deteriorated. No line is present over the immobilized HIV antigen in either path window, and a single easily discernable line is seen through window 16 at the downstream end of the pathway to test for specific antibody and sample adequacy.

Without a positive control path, this test result would have been falsely interpreted as NEGATIVE, not containing antibodies to HIV. However, with the positive control path, the user learns that some critical reagent required for a proper test is not working. Therefore the test must be read as INVALID and not interpretable. This saves the user from falsely deciding that the test indicates that no antibodies to HIV, since this interpretation cannot be made without functioning critical test reagents.

FIG. 14B—INVALID test due to use of an inadequate sample that contains insufficient immunoglobulin. FIG. 14B illustrates a 2D schematic of the results obtained as viewed through the cover of the oral fluid rapid test device after it has been used to test a sample that contained no oral fluid. A dry swab was placed into the test device and the fluid run through the test was only running buffer. A strong line is present over the immobilized HIV antigen in the results window 17 for the positive control reagent path, but no lines are observed to demonstrate binding of particulate marker to either immobilized antigen or to the immobilized rPA Ig binding reagent in window 16 over the results area of the specific antibody and sample adequacy path.

Without a control to evaluate the presence of an adequate amount of immunoglobulin in the sample being tested for antibody to HIV, this test result would have been falsely interpreted as NEGATIVE, not containing antibodies to HIV, and the user would conclude that individual who provided the sample was negative for antibodies to HIV. However, with the control to evaluate sample adequacy, the user learns that the sample tested was inadequate to allow a result interpretation. Therefore the test must be read as INVALID and not interpretable. This saves the user from possibly mistakenly concluding that the person that presented the dry swab for testing had no antibodies to HIV.

FIG. 14 C—VALID true positive test. FIG. 14C illustrates a 2D schematic of the results obtained, as viewed through the cover of the oral fluid rapid test device after it has been used to test an oral fluid sample that contained antibodies to HIV. A strong line is present over the immobilized HIV antigen in the results window 17 for the positive control reagent path. Also, clear lines of particulate marker binding are seen to both immobilized antigen, and to immobilized rPA Ig binding reagent, through window 16 of the specific antibody and sample adequacy path.

This line of particulate marker binding to immobilized antigen in window 16 of the sample adequacy and specific antibody pathway may be interpreted as a TRUE POSITIVE since the control lines indicate that all critical reagents are working, and that the sample tested contained sufficient immunoglobulin for evaluation.

FIG. 14 D—VALID true negative test. FIG. 14D illustrates a 2D schematic of the results obtained, as viewed through the cover of the oral fluid rapid test device after it has been used to test an oral fluid sample that contained no antibodies to HIV. A strong line is present over the immobilized HIV antigen in the results window 17 for the positive control reagent path. Also, a clear lines of particulate marker binding is seen to immobilized rPAIg binding reagent, through window 16 of the specific antibody and sample adequacy path. However, there is no line of particulate marker binding to immobilized antigen as viewed through window 16.

This lack of particulate marker binding to immobilized antigen in window 16 of the sample adequacy and specific antibody pathway may be interpreted as a TRUE NEGATIVE since the control lines indicate that all critical reagents are working, and that the sample tested contained sufficient immunoglobulin for evaluation.

Example 8

Evaluation of Whether Monoclonal Antibody to HIV-1 Peptide BSA Antigen is Sufficient to Produce a Discernable Line of Particulate Marker Binding with Recombinant Protein A, when Used in Concentrations of Example 3

Recombinant Protein A (rPA) was immobilized on nitrocellulose strips at 3.5 micrograms per ml downstream from the HIV-1 peptide BSA antigen under the conditions of Example 3. Monoclonal antibody F240 and colloidal gold particulate marker were run past the antigen and rPA under the conditions of Example 1. A distinct line of colloidal gold particulate marker bound to the immobilized HIV-1 peptide-BSA antigen, but no reactivity was observed where the rPA was immobilized. This indicated that the degree of binding of rPA to the small amount of monoclonal antibody was insufficient to produce a discernable line of binding of colloidal gold particulate marker complexed with Protein L+G.

An identically coated nitrocellulose strip was reacted with the same colloidal gold Protein L+G particulate marker complex under identical conditions to example 3 but an HIV-1 positive serum sample was substituted for the monoclonal antibody. A distinct line of colloidal gold particulate marker binding was observed over both at the immobilized HIV peptide-BSA conjugate antigen and over the immobilized rPA. This indicated recognition of human immunoglobulin in the HIV positive serum by rPA, and that the concentration of rPA used bound sufficient immunoglobulin in the test serum to produce a line of binding of colloidal gold marker complexed with Protein G and Protein L.

Together, these results indicate that controls for the rapid test for both sample adequacy (sufficient immunoglobulin) and reagent reactivity may be run on their own strip that is separate from the strip used to detect specific antibodies to analytes. This control strip may contain both immobilized rPA to indicate that the tested sample contains adequate amounts of immunoglobulin, and one or more binding pairs foranalytes, each consisting of a mobilizable monoclonal antibody and its specific immobilized analyte. Providing the monoclonal antibodies used are of sufficient potency that the amounts used do not result in a discernable line of colloidal gold at the immobilized rPA position, the rPA may be used on the same control strip as the reagent reactivity pathway. Otherwise, sample adequacy for immunoglobulin content can be evaluated by placing the rPA on a pathway that does not receive monoclonal antibodies.

Example 9

Devices that Prevent Backflow from Absorbent Pad to Upstream Areas of Flow Path, Thereby Lengthening the Time Window During which Results May be Reliably Observed The length of time over which the results of a rapid test may be read affect the usefulness of a test in different settings. For example, in a busy emergency room or in a hectic outpatient clinic it may not be practical to read a test result exactly 10 minutes after beginning the test and no later than 12 minutes! Current FDA approved rapid tests for HIV have reading windows of only two minutes (Trinity Unigold—between 10 and 12 minutes) five minutes (Inverness Determine—between 15 and 20 minutes) or twenty minutes (OraSureOraquick Advance—between 20 and 40 minutes).

For designs that use an absorbent pad incapable of retaining all of the liquid introduced into the rapid test, backflow may occur that obscures reliable reading of the test results. For this reason, in one embodiment, the rapid test device includes a large absorbent pad. This embodiment is shown in FIG. 16A. Well 67 measures 20.5 mm wide×39 mm long× 2.45 mm deep. An absorbent pad of this dimension composed of Ahlstrom grade 237 cellulose is capable of retaining approximately 1.1 ml of fluid. FIG. 16C illustrates the same design with test membranes in place in which flow during performance of the rapid test is from upstream areas on the right side of the device to downstream areas on the left side of the test device. All fluid introduced upstream into the test is effectively retained in the downstream absorbent pad with this design and no backflow occurs, and test results are reliably observed without backflow interference for weeks rather than minutes.

Example 10

Device Designs to Prolong Delivery of Particulate Marker, with Resulting in Increased Sensitivity of Rapid Lateral Flow Tests while Still Maintaining the Simplicity of Few Steps for Ease of Use Conventional lateral flow assays for antibodies currently available consist of single test strips containing all components positioned in-line and in fluid communication by capillary action from upstream to downstream consisting of: sample receiving pad, mobilizable marker that detects immunoglobulin in the test sample, immobilized antigen that will bind specific antibodies being detected, and absorbent pad to take up the liquid sample added upstream and maintain the flow direction of the test from upstream to downstream (see Rosenstein, U.S. Pat. No. 5,591,645). With this design, the first portion of the liquid sample to interact with the mobilizable marker consists of a high concentration of mobilizable marker relative to the amount of antibody in the liquid sample. As the test proceeds, the mobilizable marker binds to antibody in the liquid sample and the marker-antibody complexes migrate down the strip past the immobilized antigen. Subsequent amounts of liquid sample find little remaining mobilizable marker with which to interact, and though antibodies in this portion of the sample may bind to immobilized antigen downstream they are not visually recognized since all mobilizable marker has already migrated downstream from the immobilized antigen.

Rosenstein and Bloomster first described the advantages of first applying sample to immobilized analyte in lateral flow assays prior to passing tracer over the same immobilized analyte (U.S. Pat. No. 4,855,240). These advantages were further expounded by Bernstein et al. (U.S. Pat. No. 5,824, 268) and subsequently by Esfandiari (U.S. Pat. No. 7,387,890 B2). Esfandiari (Dual Path Platform Lateral Flow) and vertical flow assays that provide interaction of immobilized antigen with liquid sample containing antibodies prior to interaction with visual marker have claimed greater sensitivity (see Chan, U.S. Pat. No. 7,531,362 B2).

Experiments were conducted to determine whether design modifications to the test device might allow more antibody (analytes) in the liquid sample to bind to downstream immobilized antigen (antibody binding ligand) prior to interaction with mobilizable marker.

To determine the probable distribution of antibodies within the diluted sample produced by the test device of FIG. 1 and the method of U.S. Pat. No. 7,364,914 B2 (Buchanan), a concentrated solution of red food coloring (McCormick & Co. Inc., Hunt Valley, Md.) with a peak wavelength absorption at 535 nm, was used to saturate 2 layers of Alpha Lite Fabric (ITWTexwipe, Inc., TX 1008B) placed over the midpiece (6) with o-ring (5) of the test device (FIG. 1) containing a diluted sample membrane (8) but no test or control strips. The dilution port (2, FIGS. 1 and 10) was pushed down into locked position to compress a perimeter of the isolated area of saturated alpha lite fabric (FIGS. 10B and 10C) and 1 ml of running buffer (sample diluent, Example 1) was passed through the isolated area of alpha lite fabric saturated with a concentrated solution of red food coloring which removed it from the alpha lite and simultaneously passed the diluted solution down into the diluted sample membrane lying beneath the midpiece. The device was opened and the diluted sample membrane was visually inspected. Dividing the diluted sample membrane into quarters, the peripheral 25% ends of the diluted sample membrane were dark red, and the inner 25% portions outside of a central white circular area corresponding to the exit flow path from the midpiece were a lighter red. These observations indicate that the highest concentration of diluted sample migrate from the center of the diluted sample membrane to the outside edges, and subsequent running buffer contacts less sample within the alpha lite fabric and these lower dilutions distribute closer to the exit point from the midpiece.

The diluted sample membrane (DSM) was cut into fourths consisting of two outer and two inner portions. Each was placed into a test tube and 1 ml of DI water was added, and each test tube was then mixed for 20 seconds on a vibratory shaker. Aliquots of each tube were then read in a spectrophotometer for absorbance at 535 nm wavelength. The two outer 25% portions produced readings of 1.201 and 1.303 for an average absorbance of 1.252. The two inner 25% portions produced readings of 0.665 and 0.785 for an average absorbance of 0.725 confirming the visual observation that higher concentrations of diluted sample were found in the peripheral portions of the DSM membrane as compared to portions near to the exit well from the midpiece.

To estimate the approximate differences in concentration of diluted sample between peripheral and inner portions of diluted sample membrane when liquid samples are diluted according to U.S. Pat. No. 7,364,914 B2 (Buchanan), a standard curve of dilutions on concentrated red food coloring was performed, beginning with 535 nm absorbance of 1.255 and diluting therefrom. The standard curve indicated that the average concentration of diluted sample in the inner two 25% portions of the DSM was approximately 50% of the average concentration of the red food coloring in the outer two 25% portions of the DSM. Thus, during performance of the rapid test using the method and rapid test device design described herein, concentrations of diluted sample to migrate over the two pathways, the pathway to evaluate reagent reactivity and the separate pathway to detect antibodies (analytes) to specific antigens (antibody binding ligands) are at their highest level initially, and then the concentrations of diluted sample decrease to approximately half of the initial levels on average during delivery of the second half of the diluted sample through the reagent reactivity and specific analyte detection pathways.

FIG. 16A illustrates a design modification for the rapid test device to allow a portion of the particulate marker to be delivered throughout most of the period of fluid flow from diluted sample membrane to absorbent pad. In FIG. 16A, the more central of the two dilution port receptacles (29, FIG. 8B) in the base has been moved centrally, which allows room for a long strip containing mobilizable colloidal gold protein G+L particulate marker (55, FIG. 16B) to overlap partially along its upstream long edge with the diluted sample membrane and to rest predominantly upon a plastic surface of the base (49, FIG. 16A) adjacent the well for the diluted sample membrane. Only its ends are directly in line with upstream portions of the test and control flow paths (FIG. 16C). The portion of particulate marker strip that is directly in line with the separate reagent reactivity and specific analyte detection flow paths interacts with the initial higher concentrations of diluted sample and flows downstream in line with the leading edge of fluid flowing through the test, as is typical for conventional lateral flow diagnostic tests. However, for the particulate marker in the more central regions of the long particulate marker strip to reach the reagent reactivity and separate specific analyte detection flow paths, it must interact with diluted fluid from the central regions of the diluted sample membrane. These more central regions contain lower concentrations of diluted sample (FIG. 16F).

As shown in FIGS. 16E and 16F, the methods and devices of this invention allow particulate marker from pad 67 to interact with diluted sample membrane (56) over a variety of diluted sample concentrations ranging from 0% to 100% of the most concentrated dilution produced by the test device. This is in contrast to conventional particulate marker pads, such as pad 68, FIGS. 16E and 16F, that are in-line and the same width as the downstream membranes of the pathway, and interact only with the leading edge of a sample dilution, which is generally of higher concentration than subsequent sample to migrate over the test device. In FIG. 16F, conventional particulate marker pad 68 interacts only with sample dilutions ranging from 70-100% of full strength dilution. In contrast, particulate marker pad 67 presents the same amount of particulate marker to sample dilutions of 0-10% of full strength at the center of the diluted sample pad, as it does to sample dilutions of 10-40% one step from the center, and to sample dilutions of 40-70% next further from the center, and to 70-100% of full strength sample dilutions near the point where it joins with the specific antibody pathway 53 (FIG. 16F). This provides more opportunity than with conventional lateral flow immunoassays to achieve optimal complexes of marker to immunoglobulin molecules such that the complexes contain fully functional immunoglobulin molecules to recognize and bind to downstream immobilized antigen (analyte binding ligands) yet also form large enough clumps of bound marker to provide optimal detection of specific antibodies (analytes) bound to immobilized antigen.

Another advantage of the use of a membrane for collecting diluted sample (FIGS. 16B, 16C, 16E, and 16F) instead of a well as used in U.S. Pat. No. 7,364,914 is that there is less likelihood of spillage of diluted sample if the test device is bumped or used in a non-level surface. The membrane holds the diluted sample within its void spaces, available for flow by capillarity into downstream membranes, but this ability to hold the diluted sample on varying concentrations is not overcome by bumping the test while it is running or performing the rapid test on a less than level surface.

When this design was compared to the more conventional use of particulate marker in lateral flow assays, particulate marker with the modified design was delivered to the test and control strips in more intense amounts approximately 50% longer than with conventional lateral flow designs, and lower amounts of particulate marker continued to be delivered to the test and control strips for approximately three times longer. When the test was disassembled after completion, the particulate marker strip was consistently noted to be white, indicating near complete removal from all particulate marker from the longer strip and its delivery to the specific analyte detection flow path (FIGS. 16E and 16F) or to both the reagent reactivity and specific analyte detection flow paths (FIG. 16A) membranes. This longer delivery period of particulate marker provides an opportunity for more antibodies within the diluted test sample to reach and bind to immobilized antigens downstream prior to the last available particulate marker that might recognize this binding exiting the flow paths into the absorbent pad.

In another experiment, the time period during which colloidal gold particulate marker was delivered to the end of the viewing window for this modified design was 3 times longer than with the conventional lateral flow immunoassay design (Table 5, Example 12). In conventional lateral flow immunoassays all of the mobilizable particulate marker is contained on an in-line strip between sample pad upstream and nitrocellulose membrane downstream and all of the particulate marker from the strip enters the lateral flow immunoassay with the initial diluted sample flowing from the sample pad. After this initial interaction between sample and particulate marker, sample continues to flow over the lateral flow immunoassay but there is little particulate marker, if any, with which to interact.

With this modified design, diluted sample and particulate marker migrate laterally together into the downstream specific antibody (analyte) detection zones containing immobilized antigen (analyte binding ligands) where reactivity is observed through the test device windows. This is in contrast to the methods and devices of Rosenstein (U.S. Pat. No. 4,855,240), Bernstein (U.S. Pat. No. 5,824,268) and Esfandiari (U.S. Pat. No. 7,189,522 B2—Dual Path Platform) where sample collection and preparation and delivery to the test device are via a different pathway than the pathway used for particulate marker and the two pathways meet at the detection zone of immobilized antigen, with sample preferably reaching the detection zone before marker. With this invention, there is no need to use separate application points for sample and buffer, thus retaining the simplicity and ease of use desired for point-of-care and at-home testing sites.

adjacent the exit port of the midpiece on the undersurface of the midpiece. This action produced diluted F240 antibody dilutions that averaged 1:200-1:250 dilutions of the concentration of F240 delivered to the LF1 membrane, but contained higher concentrations of F240 near the ends of the diluted sample membrane and lower concentrations than 1:250 in the more central regions of the diluted sample membrane. These dilutions were then run over the two pathways of the FIG. 16C device, the reagent reactivity pathway, and the specific analyte (antibody) detection pathway. In one case the particulate marker was provided with a strictly in line upstream particulate marker pad as is typical for conventional lateral flow immunoassays (membrane 68, FIG. 16C). In another embodiment, the device of the invention provides a longer and thinner pad of particulate marker positioned as illustrated by pad 67 (FIG. 16 C). Observable line intensity over the immobilized HIV-1 antigen was evaluated at 10, 15, and 20 minutes for each test design and the results are summarized in Table 2.

TABLE 2

Sensitivity of new and conventional lateral flow immunoassay Methods and device designs for detection of monoclonal antibody to hiv-1

| New Lateral Flow Design | | | | Conventional Lateral Flow Design | | | |
|---|---|---|---|---|---|---|---|
| Line Intensity | 10 min | 15 min | 20 min | Line Intensity | 10 min | 15 min | 20 min |
| | Picograms F240 | | | | Picograms F240 | | |
| 7500 | 5 | 5 | 5 | 7500 | 4 | 4 | 4 |
| 750 | 4 | 4 | 4 | 750 | 2.0 | 3 | 3 |
| 75 | 2.5 | 3 | 3 | 75 | 0 | 0.5 | 1 |
| 7.5 | 0 | 0.5 | 0.75 | | | | |

Example 11

Evaluation of Relative Sensitivity of Rapid Lateral Flow Tests that Employ Prolonged Delivery of Particulate Marker During the Reaction as Compared to Conventional Rapid Lateral Flow Tests The rapid test device using the base of FIG. 16A and cover of FIG. 15A and whole blood insert of FIG. 17 was used to detect antibodies to HIV-1 peptide-BSA antigen in dilutions of monoclonal antibody F240 that recognizes the immobilized HIV-1 peptide-BSA antigen as described in Examples 1 and 2. Dilutions of the F240 monoclonal antibody in test running buffer (Example 1) such that 40 microliters of running buffer that produced saturation of an LF1 membrane (Example 6) overlying the o-ring of the test device (FIG. 16D) contained 7500 pg, 750 pg, 75 pg or 7.5 pg of monoclonal antibody. Once the LF1 membrane received the designated quantity of monoclonal antibody F240, the dilution port of the test device was pushed down into the locked position to isolate a circle of saturated membrane centripetal to the o-ring and 1 ml of running buffer was delivered with pressure through the opening in the top of the dilution port (2, FIG. 1) to remove and simultaneously dilute the monoclonal antibody and deliver it to the diluted sample membrane located These results suggest a five to ten-fold improvement in sensitivity with the New Generation Modified Design of this invention as compared to conventional lateral flow techniques for this embodiment.

Sensitivity differences between conventional lateral flow test device designs and the new generation design of FIG. 16C were evaluated using seroconversion panel PRB 945, obtained from SeraCare Life Sciences Corporation, Milford, Mass., USA. This panel contained 6 members collected at 0, 3, 7, 13, 15, and 20 days from the date of the first bleed. HIV RNA by Roche PCR was detectable in all 6 members beginning with 300 copies/ml in sample 1, 700/ml in sample 2, 9000 in sample 3 and greater than 80,000 in samples 4-6. No antibodies were detectable by any tests, including 2010 instrument based tests, in samples 1-3, and none of the six samples gave uniformly positive Western Blot tests. Sample 6 gave a positive Western Blot result in one of three confirmatory Western Blot tests, and the other two were indeterminate. Detection of antibodies to HIV in sample 4 was possible with six of six 2010 instrument based tests, with five of twelve 1997 instrument based tests, and with no rapid non-instrument based tests. Sample 5, taken 2 days after sample 4, contained antibody to HIV detectable by all six 2010 instrument based HIV antibody tests, nine of twelve 1997 instrument-based tests, and a single vertical flow-through rapid non-instrument based 1997 test. Sample 6, taken 5 days after sample 5 and 20 days after sample 1, contained antibodies to HIV-1 in all 2010 instrument based tests, in 10 of 12 1997 instrument based tests, and in a single rapid vertical flow through rapid test.

Sample 6 was tested in the rapid test device of this invention (FIGS. 15-18) with particulate marker delivered both in conventional lateral flow format, or in the new generation modified format designed to deliver particulate marker over a longer period during test development. The results are shown in Table 3.

TABLE 3

Sensitivity for Detection of Seroconversion by Conventional as Compared to New Device Designs and Methods incorporating New Size and Orientation of Particulate Marker Pads and Multiple Ratios and Extended Duration of Marker to Immunoglobulin Interactions

| New Lateral Flow Design | | | | Conventional Lateral Flow Design | | | |
|---|---|---|---|---|---|---|---|
| Line Intensity | 10 min | 15 min | 20 min | Line Intensity | 10 min | 15 min | 20 min |
| Sample 6 of SeraCare Corporation PRB 945 SeroConversion Panel tested by | | | | | | | |
|  | 1 | 1.5 | 2 |  | 0 | 0 | 0 |
| Sample 5 of SeraCare Corporation PRB 945 SeroConversion Panel tested by | | | | | | | |
|  | 0 | 0.5 | 1.0 |  | 0 | 0 | 0 |

These results indicate that sensitivity is increased using the new generation lateral flow design of this invention that delivers particulate marker over longer periods of antigen antibody interactions and allows test development with a greater range of immunoglobulin concentrations relative to particulate marker than occurs with tests employing conventional designs for rapid lateral flow immunoassays.

Example 12

Studies of the Effect of Sample Immunoglobulin Concentration on the Intensity of Observable Binding of Particulate Marker to Immobilized Antigen and Recombinant Protein A, and Comparisons of Particulate Marker Delivery Times with Conventional Rapid Lateral Flow Designs as Compared to New Generation Lateral Flow Designs of this Invention The test device particulate marker design of FIG. 16C was used to evaluate reactivity of F240 with HIV-1 BSA-peptide antigen as influenced by the concentration of normal human serum in the test sample diluted with running buffer. The monoclonal antibody was coated in mobilizable form onto Millipore GFCP203000 (Bedford, Mass., USA) under the conditions of Example 2, and was mobilized by the sample migrating from the diluted sample membrane (56, FIG. 16C) downstream past mobilized antigen, then recombinant protein A, and into the absorbent pad (50, FIG. 16C). The intensity of binding of particulate marker to nitrocellulose immobilized HIV-1 peptide-BSA antigen, and downstream to recombinant protein A, is shown in Table 4.

TABLE 4

Effect of Serum Concentration Tested on Intensity of Reaction Observed

| Serum Concentration of Diluted Sample | Observed Intensity of Particulate Marker Binding to | |
|---|---|---|
|  | Immobilized Antigen | Recombinant Protein A |
| 1:25 Diluted Serum | 0.75 | 0.75 |
| 1:80 Diluted Serum | 2 | 2 |
| 1:200 Diluted Serum | 3 | 4 |

These results indicate that the amount of particulate marker available in rapid lateral flow immunoassays is insufficient to bind all of the immunoglobulin in serum specimens more concentrated than 1:80, and that these immunoassays is more likely to produce reliable results at serum concentrations more dilute than 1:150.

In the rapid lateral flow immunoassays of this invention, the design shown in FIG. 16C may be expected to detect specific antibodies with higher sensitivity than conventional lateral flow immunoassays for several reasons. One of these reasons is that particulate marker is delivered over longer time periods of the assay with the new generation design than with conventional configurations, as that shown in FIG. 16E [conventional design pathway 52 (the reagent reactivity pathway)] with particulate marker pad 68, versus new generation design pathway 53 (the specific analyte detection pathway) with particulate marker pad 67)]. This longer delivery of particulate marker allows recognition of analyte (antibody) in the diluted sample not previously bound to particulate marker, or only sparsely bound, that has migrated to and bound to immobilized analyte binding ligands (antigen) downstream and is then recognized by particulate marker when it later migrates by as it is released later by the new generation design (pad 67 and pathway 53, FIG. 16C). Another potential reason for increased sensitivity is that analyte (immunoglobulin) concentrations are lower in the eluent from the diluted sample membrane onto each downstream pathway during the latter half of fluid flow from diluted sample membrane to absorbent pad, as further described in Example 10 above. These lower concentrations of immunoglobulin may interact more favorably with particulate marker eluting from the new generation pad designs (pad 67, FIG. 16C), during the second half of diluted sample migration during the test than with the higher immunoglobulin concentrations present in the diluted that migrate past the particulate marker pad during the first half of sample migration.

To directly compare the duration of particulate marker delivery to downstream test components from conventional and new generation particulate marker pads a test with the particulate marker configuration shown in FIG. 16E was performed. In FIG. 16E, particulate marker pad 68 is of conventional configuration and delivers its colloidal gold particulate marker to pathway 52 (the reagent reactivity flow pathway). For comparison, particulate marker 67 is of new generation configuration and delivers is colloidal gold particulate marker to pathway 53 (the specific analyte detection flow pathway). The flow patterns of diluted sample delivered to area 57 of the diluted sample membrane, and spreading from there to saturate the membrane, are shown by four dashed lines 58 leading to pathway 52, and by six dashed lines 58 leading to pathway 53 (FIG. 16E). In both pathways, initial flow from diluted sample membrane into colloidal gold particulate marker pads is from diluted sample in the saturated ends of the membrane through the particulate marker pads at the upstream end of each pathway through the bridging membranes (59, dashed lines) into the nitrocellulose strip (membrane containing immobilized analyte binding ligands) of each pathway, and then down each flow pathway into the absorbent pad (50, FIG. 16E). However, later portions of the diluted fluid sample do not carry any particulate marker into pathway 52 since all of the marker was removed with the initial diluted sample that migrated through pad 68. In contrast, after all particulate marker has been removed from the portion of particulate marker pad 67 that is adjacent the upstream end of pathway 53, there is still opportunity for continued flow of particulate marker from the portions of pad 67 that are not immediately adjacent to the upstream end of pathway 53, as shown by dashed lines 58 of FIG. 16E. Diluted sample migrates into particulate marker pad 67 from its overlap along one edge with the diluted sample membrane, and continues migration down pad 67 until marker can enter the upstream portions of pathway 53 via the bridging membrane 59 (dashed lines) connecting pad 67 to the upstream end of the nitrocellulose membrane (immobilized analyte binding ligand membrane) portion of pathway 53 (the specific analyte detection flow pathway). When the duration of flow of visible particulate marker colloidal gold-protein G+L was observed for pathways 52 and 53 with the test design of FIG. 16E, the results shown in Table 5 were obtained.

TABLE 5

Time periods observed for colloidal gold marker to reach and leave reading windows of rapid lateral flow assay with conventional as compared to new design and orientation of particulate marker pads

|  | Conventional | New |
| --- | --- | --- |
| Time period for leading edge of visually observable colloidal gold visual marker to reach downstream end of viewing window of test device | 40 seconds | 40 seconds |
| Time period for last of visible colloidal gold marker to reach downstream end of viewing window | 3 min 30 sec. | 10 min 30 sec. |

The results of Table 5 demonstrate that a particulate marker pad of the new design of this invention, such as pad 67 of FIG. 16E, can deliver colloidal gold marker to rapid lateral flow immunoassays for a time period approximately 3 times longer than the time period during which this marker can be delivered from pads of conventional lateral flow configuration, such as pad 68 of FIG. 16E. This prolonged availability of particulate marker capable of recognizing downstream analytes (antibodies) bound specifically to immobilized analyte binding ligands (antigens) throughout the rapid test performance, allows recognition of analytes (antibodies) specific to immobilized analyte binding ligands (antigens) that may have bound to those analyte binding ligands (antigens) during minutes 4 through 9 of the test performance, which is not possible with the conventional lateral flow designs for particulate marker delivery to test strips. This increased recognition of antibodies bound during 4-9 minutes of the test, in this example, may explain, at least in part, the observed higher sensitivity of the new generation particulate marker pad delivery method of this invention observed in Tables 2 and 3 of Example 11.

Example 13

Use of a Specifically Designed Whole Blood Insert for Testing Whole Blood Samples within the Rapid Test Device LF1 membrane (GE-Whatman, Florham Park, N.J.) was cut precisely to the inner dimensions over the platform and its open space of the whole blood insert (FIG. 17B, 62 and 64, respectively) and the top portion of this insert (FIG. 17A) was fitted to it to hold the membrane in place. The whole blood insert containing the L1 membrane was placed into position in the rapid test device with the device design cover of FIG. 18 and the device design base of FIG. 16A, that contained a midpiece (6, FIG. 1) that contained size 008 o-ring within its top surface (23, FIG. 7). A contact-activated lancet from Becton Dickinson (Becton Dickinson, Franklin Lakes, N.J., USA) was used to lance a volunteers fingertip and two free-falling drops of whole blood from the fingertip were allowed to drop onto the area of the LF1 membrane located beneath the opening in the top piece of the whole blood insert (65, FIG. 18). After 4 minutes, this whole blood had migrated to the opposite end of the LF1 membrane and the area defined by the 008 membrane (66, FIG. 18) was enriched for acellular as compared to cellular components of the whole blood. At this time, the yoke (1, FIG. 1) was removed from the dilution port (2, FIG. 1) and pressed down into the base receptacles (29, FIG. 8B) where its hook arms (32, FIG. 9C) locked into position within the base receptacle windows (30, 8C) of the dilution port hook arms (32S and 33S, FIG. 9C). In this locked position the bottom surface of the central channel opening of the dilution port (37, FIGS. 2B and 2C) applies compressive force on the top surface of the membrane that overlies the o-ring within the top surface of the midpiece (5, FIGS. 7B and 7C). This force is met by a corresponding opposing force from the o-ring on the undersurface of the membrane and together these forces compress and collapse the LF1 membrane void spaces that are saturated with the acellular-enriched sample of whole blood, thereby isolating an area of saturated membrane centripetal to the ring of compression, in accordance with U.S. Pat. No. 7,364,914. Thereafter, one ml of running buffer for the rapid test was expressed under pressure via a vial or syringed that formed friction leak-proof fit between the neck of the vial or exit of the syringe and the opening in the top surface of the dilution port (FIG. 2A). This running buffer traveled through channel 36 (FIG. 3A) to exit the dilution port overlying the isolated membrane, and continued through the membrane removing the acellular-enriched blood sample and simultaneously diluting it and delivering it through channel 25 of the midpiece (FIG. 7A) and exiting at 27 in the undersurface of the midpiece (FIG. 7C) onto the diluted sample membrane 56 at area 57 (FIG. 16B) and from there flowed over the pathways of the rapid test as illustrated by example in FIGS. 13, 16C, and 16E.

While illustrative embodiments have been illustrated and described, it will be appreciated that various changes can be made therein without departing from the spirit and scope of the invention.

The invention claimed is:

1. A method for detecting an analyte in a liquid sample and checking the reactivity of the method reagents comprising:
    (a) isolating a portion of a compressible membrane containing at least a portion of a liquid sample to be analyzed by applying compressive force on top and bottom surfaces of the membrane along a perimeter of an area to be isolated thereby defining a non-compressed area of the membrane centripetal to the compressed perimeter;

(b) delivering a pre-determined amount of liquid diluent under pressure to the isolated portion of the membrane to release at least a portion of the liquid sample from the isolated portion of the membrane to provide a diluted sample;

(c) contacting the diluted sample with a second porous membrane having a first and second end, wherein the diluted sample flows toward the first and second ends;

(d) conducting the diluted sample from one portion of the second porous membrane into a first flow path that provides flow from the second porous membrane upstream to an absorbent pad downstream, wherein the flow path comprises porous membranes and reagents to evaluate reagent reactivity comprising in flow order: (i) a membrane containing mobilizable marker for the class of analytes being detected, (ii) a bridging membrane containing mobilizable binding partners specific to downstream immobilized ligands being used to detect the analytes of interest in the diluted sample, the mobilized binding partners capable of being recognized by the mobilizable marker, (iii) a membrane containing immobilized ligands for the analytes of interest, and (iv) an absorbent pad either in direct fluid communication with the membrane for immobilized ligands or connected thereto via an outflow wick membrane;

(e) conducting the diluted sample from different portions of the second porous membrane into a second flow path that provides flow from the second porous membrane upstream to an absorbent pad downstream and comprises porous membranes and reagents to detect specific analytes of interest comprising in flow order: (i) a membrane containing the mobilizable marker, (ii) a bridging membrane connecting the mobilizable marker membrane to a membrane containing immobilized ligands for detecting specific analytes of interest, and (iii) an absorbent pad either in direct fluid communication with the membrane for immobilized ligands or connected to it via an outflow wick membrane;

(f) observing the results of migration of the liquid sample through the first flow path comprising observable marker bound to immobilized ligand or ligands for the analyte or analytes of interest, which allows confirmation that the marker was reactive and capable of binding to the class of analytes being detected, that the immobilized ligand or ligands were reactive and capable of binding the specific analytes being detected by the test, and that the mobilizable binding partners specific for the immobilized ligand or ligands were also reactive, thereby indicating that the test is capable of detecting the analytes of interest in the diluted sample;

(g) observing the results of migration of the liquid sample through the second flow path comprising observable marker bound to immobilized ligand or ligands for the analyte or analytes of interest, which allows confirmation that analytes of interest are present in the diluted sample, or comprising no observable marker bound to immobilized ligand in the second flow path if no analytes of interest are present in the diluted sample; and (h) observing that no valid interpretation can be reached for the test method if no marker lines are present in immobilized ligand portion of the first flow path.

2. The method of claim 1, wherein immobilized recombinant protein A is immobilized downstream from immobilized antigen on one of the flow paths, and used to evaluate whether sufficient immunoglobulin is present in the diluted test sample to allow detection of antibodies specific to that antigen in the diluted test sample.

3. The method of claim 1, wherein the mobilizable marker is selected from the group consisting of protein G, protein L and protein A, each bound to one or more observable components selected from the group consisting of colloidal gold, magnetic spheres and fluorescent markers.

4. The method of claim 1, wherein the mobilizable marker is protein G and protein L bound to colloidal gold.

5. The method of claim 1, wherein the membrane containing mobilizable marker delivers marker to the second flow path during 50% or more of the total time period for assay completion.

6. The method of claim 1, wherein the membrane containing mobilizable marker delivers marker to the second flow path during more than 75% of the total time period for assay completion.

7. The method of claim 1, wherein the diluted sample second porous membrane is aligned with the mobilizable marker membrane containing mobilizable marker in the second flow path to provide marker mixing with a range of dilutions of diluted sample, from highest concentration of diluted sample to dilutions containing only 20 percent or less of the highest concentration of diluted sample.

8. The method of claim 1, wherein the liquid sample is a biologic sample from a mammal.

9. The method of claim 1, wherein the liquid sample is a biologic sample from a non-mammal.

10. The method of claim 1, wherein the liquid sample is whole blood or a fraction thereof.

11. The method of claim 1, wherein the liquid sample is gingival crevice oral fluid.

12. The method of claim 1, wherein the analyte binding ligand is the antigen and the analyte is the antibody.

13. The method of claim 1, wherein the analyte binding ligand is the antibody and the analyte is the antigen.

14. The method of claim 1, wherein the analytes are the antibodies to HIV and the analyte binding ligands are HIV antigens.

15. The method of claim 1, wherein the sample diluent comprises a fluid that provides favorable pH and ionic conditions for effective reactions between analytes and their binding partners, and contains added protein and detergent to promote migration of reagents without non-specific adherence of components along the separate flow paths.

16. The method of claim 1, wherein the absorbent pad has a capacity to receive and hold the total liquid volume added to the test device.

17. A device for detecting an analyte in a liquid sample and checking the reactivity of the reagents used to detect the analyte, comprising:

(a) a compressible porous membrane for receiving a liquid sample;

(b) first and second members adjacent opposing major surfaces of the compressible porous membrane, wherein the first and second members are engageable to apply compressive force on top and bottom surfaces of the membrane along a perimeter of the area to be isolated, thereby defining a non-compressed area of membrane centripetal to the compressed perimeter containing at least a portion of a liquid sample to be analyzed;

(c) a port to receive delivery of a second fluid, wherein the port is delivers the second fluid to the top surface of the isolated portion of the membrane to force the removal of at least a portion of the liquid sample from the isolated portion of the porous sample receiving membrane;

(d) a channel to collect the diluted liquid sample from the bottom surface of the isolated portion of membrane;

(e) a second porous membrane for receiving the diluted sample from the isolated compressible sample membrane, the second porous membrane having first and second ends, and where the diluted sample migrates from point of application to each end of the second porous membrane;

(f) a first flow path for evaluating reagent reactivity that delivers diluted sample from one portion of the second porous membrane to an absorbent pad downstream and comprises porous membranes and reagents to evaluate reagent reactivity comprising in flow order: (i) a membrane containing mobilizable marker for the class of analytes being detected, (ii) a bridging membrane containing mobilizable binding partners specific to downstream immobilized ligands being used to detect the analytes of interest in the diluted sample, the mobilized binding partners capable of being recognized by the mobilizable marker, (iii) a membrane containing immobilized ligands for the analytes of interest, and (iv) absorbent pad positioned at a pre-defined location in the device; and (g) a second flow path for detecting specific analytes that delivers diluted sample from other portions of the second porous membrane to an absorbent pad downstream and comprises porous membranes and reagents to detect specific analytes of interest comprising in flow order: (i) a membrane containing the mobilizable marker, (ii) a bridging membrane connecting the mobilizable marker membrane to a membrane containing immobilized ligands for detecting specific analytes of interest, and (iii) an absorbent pad held within a defined location of the device.

18. The device of claim 17, wherein the compressible porous membrane is a hydrophilic glass membrane with low protein binding that retards cellular components from noncellular components of whole blood during lateral migration through the membrane.

19. The device of claim 18, wherein the compressible porous membrane positioned to collect whole blood on one end, allow free migration along the membrane to an opening provided at the opposing end of the insert, and that allows isolation, removal and delivery of the acellular enriched components of whole blood to the test device.

20. The device of claim 17, wherein the compressible porous membrane for use with gingival crevice or other oral fluid is a hydrophilic membrane that saturates with oral fluid, is sonically welded to a close fit around a swab for collecting oral fluid, and releases the oral fluid sample into the device with minimal protein loss.

21. The device of claim 17, wherein a swab surrounded on its oral fluid collection end by the membrane fits into an opening of the device that allows isolation, removal and delivery of diluted oral fluid into the test device.

22. The device of claim 17, wherein the porous diluted sample membrane comprises a hydrophilic large pore glass membrane with sufficient binder to prevent migration of small glass particles from the membrane into the reagent reactivity and specific antibody flow paths that originate from it.

23. The device of claim 17, wherein the membrane containing the mobilizable marker of both flow paths comprises a hydrophilic large pore glass or polyester membrane modified to be hydrophilic, such that adherence of marker complex to the membrane and restriction of flow of the mobilizable marker complex from the membrane is minimized when marker complex is dried onto the membrane in the presence of sucrose or other sugars, and mobilized from the dried state with liquid sample diluent that promotes migration with minimal adherence of reagents along the flow paths.

24. The device of claim 17, wherein the bridging membrane of both flow paths comprises a large pore glass with minimal protein binding.

25. The device of claim 17, wherein the bridging membrane in the first flow path comprises binding partners specific to downstream immobilized ligands dried in a mobilizable state.

26. The device of claim 17, wherein the bridging membrane in the second flow path does not comprise analytes specific to downstream immobilized ligands.

27. The device of claim 17, wherein the absorbent pad has a capacity to receive and hold the total liquid volume added to the device.

28. The device of claim 17, further comprising apertures, through which one may observe the results of binding or no binding of marker to ligands immobilized on the ligand binding membrane of both flow paths.

29. A kit for detecting antibodies to HIV in whole blood or components thereof, comprising:
(a) a lancet for obtaining fingerstick blood;
(b) an insert for collecting blood drops and for inserting into the device of claim 16;
(c) the device of claim 17; and
(d) a vial or syringe to deliver a predetermined amount of sample diluent under pressure through a port of the device.

30. A kit for detecting antibodies to HIV in gingival crevice oral fluid, comprising:
(a) a swab for collecting oral fluid and for inserting into the device of claim 16;
(b) the device of claim 17; and
(c) a vial or syringe to deliver a predetermined amount of sample diluent through a port of the device.

* * * * *

UNITED STATES PATENT AND TRADEMARK OFFICE
CERTIFICATE OF CORRECTION

PATENT NO. : 8,105,843 B2
APPLICATION NO. : 12/939982
DATED : January 31, 2012
INVENTOR(S) : T. M. Buchanan It is certified that error appears in the above-identified patent and that said Letters Patent is hereby corrected as shown below:

In the Claims

| COLUMN | LINE | | |
|---|---|---|---|
| 48 (Claim 17, | line 15) | 62 | After "port" delete "is" |
| 50 (Claim 29, | line 5) | 40 | "claim 16" should read --claim 17-- |
| 50 (Claim 30, | line 4) | 48 | "claim 16" should read --claim 17-- |

Signed and Sealed this
Twenty-seventh Day of May, 2014

Michelle K. Lee
*Deputy Director of the United States Patent and Trademark Office*